(12) United States Patent
Kodali et al.

(10) Patent No.: US 8,873,038 B2
(45) Date of Patent: Oct. 28, 2014

(54) TAILORED RAMAN SPECTROCOPIC PROBES FOR ULTRASENSITIVE AND HIGHLY MULTIPLEXED ASSAYS

(75) Inventors: Anil K. Kodali, Beaverton, OR (US);
Xavier Llora, Mountain View, CA (US);
Rohit Bhargava, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 157 days.

(21) Appl. No.: 13/277,674

(22) Filed: Oct. 20, 2011

(65) Prior Publication Data

US 2012/0212733 A1    Aug. 23, 2012

Related U.S. Application Data

(60) Provisional application No. 61/407,233, filed on Oct. 27, 2010.

(51) Int. Cl.
| | | |
|---|---|---|
| G01J 3/04 | (2006.01) | |
| G01N 21/65 | (2006.01) | |
| C09B 67/08 | (2006.01) | |
| B01J 13/22 | (2006.01) | |
| C09B 67/02 | (2006.01) | |
| B82Y 40/00 | (2011.01) | |
| B82Y 15/00 | (2011.01) | |

(52) U.S. Cl.
CPC B01J 13/22 (2013.01); *B82Y 40/00* (2013.01); G01N 21/658 (2013.01); C09B 67/0007 (2013.01); *B82Y 15/00* (2013.01); C09B 67/0097 (2013.01)
USPC .......................................................... 356/301

(58) Field of Classification Search
USPC ..................... 356/301, 445; 75/343; 324/214; 428/403
See application file for complete search history.

(56) References Cited

U.S. PATENT DOCUMENTS

| | | | | |
|---|---|---|---|---|
| 7,147,687 | B2 * | 12/2006 | Mirkin et al. ................... | 75/343 |
| 7,271,896 | B2 * | 9/2007 | Chan et al. ..................... | 356/301 |
| 2002/0187347 | A1 * | 12/2002 | Halas et al. .................... | 428/403 |
| 2010/0253940 | A1 * | 10/2010 | Xia et al. ....................... | 356/301 |
| 2011/0025315 | A1 * | 2/2011 | Ohtsuka ......................... | 324/214 |
| 2012/0057165 | A1 * | 3/2012 | Natan et al. ................... | 356/445 |

OTHER PUBLICATIONS

Caruso et al., "Multilayer Assemblies of Silica-Encapsulated Gold Nanoparticles on Decomposable Colloid Templates," *Advanced Materials*, 13(14):1090-1094, (2001).

Chithrani et al., "Determining the Size and Shape Dependence of Gold Nanoparticle Uptake into Mammalian Cells," *Nano Letters*, 6(4):662-668, (2006).

(Continued)

*Primary Examiner* — Tarifur Chowdhury
*Assistant Examiner* — Jamil Ahmed
(74) *Attorney, Agent, or Firm* — Klarquist Sparkman, LLP

(57) ABSTRACT

Embodiments of nanostructured, multilayered metal-dielectric particles suitable for use as Raman spectroscopic probes are disclosed, as well as methods of designing, making and using such multilayered nanoparticles, and kits including the multilayered nanoparticles. The multilayered nanoparticles include alternating metal and dielectric layers and an outer dielectric shell. One or more of the dielectric layers may include a plurality of reporter molecules. Embodiments of the multilayered nanoparticles are suitable for detecting target analytes in a sample. Some embodiments of the multilayered nanoparticles are suitable for use in multiplexed assays, including assays for multiple target analytes having differing concentrations.

12 Claims, 23 Drawing Sheets
(21 of 23 Drawing Sheet(s) Filed in Color)

(56) References Cited

OTHER PUBLICATIONS

Deb and Agrawal, "Simulated Binary Crossover for Continuous Search Space," *Convenor, Technical Reports, Department of Mechanical Engineering, Indian Institute of Technology*, pp. 1-33, (1994).

Deb and Kumar, "Real-coded Genetic Algorithms with Simulated Binary Crossover: Studies on Multimodal and Multiobjective Problems," *Complex Systems*, 9:431-454, (1995).

Draine and Flatau, "Discrete-dipole approximation for scattering calculations," *Journal of the Optical Society of America A*, 11(4):1491-1499, (1994).

Ghosh, "Dispersion-equation coefficients for the refractive index and birefringence of calcite and quartz crystals," *Optics Communications*, 163:95-102, (1999).

Hu et al., "Optical properties of gold-silica-gold multilayer nanoshells," *Optics Express*, 16(24): 19579-19591, (2008).

Johnson, "Light scattering by a multilayer sphere," *Applied Optics*, 35(18):3286-3296, (1996).

Johnson and Christy, "Optical Constants of the Noble Metals," *Physical Review B* 6(12):4370-4379, (1972).

Kelly et al., "The Optical Properties of Metal Nanoparticles: The Influence of Size, Shape, and Dielectric Environment," *The Journal of Physical Chemistry B*, 107:668-677, (2003).

Khlebtsov and Khlebtsov, "Ultrasharp light-scattering resonances of structured nanospheres: effects of size-dependent dielectric functions," *Journal of Biomedical Optics*, 11(4):1-5, (2006).

Kodali and Bhargava, "Tunable multilayered nanospheres as probes for surface enhanced Raman spectroscopy," *Proc. of SPIE*, 7032:1-10, (2008).

Kodali et al., "Optimized nanospherical layered alternating metal-dielectric probes for optical sensing," *Optics Express*, 18(22):23302-23313, (2010).

Kodali et al., "Optimally designed nanolayered metal-dielectric particles as probes for massively multiplexed and ultrasensitive molecular assays," *PNAS*, 107(3):13620-13625, (2010).

Leupacher and Penzkofer, "Refractive-index measurement of absorbing condensed media," *Applied Optics*, 23(10):1554-1557, (1984).

Natan, "Concluding Remarks Surface enhanced Raman scattering," *Faraday Discussions*, 132:321-328, (2006).

Sastry and Goldberg, "Modeling Tournament Selection With Replacement Using Apparent Added Noise," *Illinois Genetic Algorithms Laboratory Report No. 2001014*, pp. 1-8, (2001).

See et al., "A reactive core-shell nanoparticle approach to prepare hybrid nanocomposites: effects of processing variables," *Nanotechnology*, 16:1950-1959, (2005).

Wiscombe, "Improved Mie scattering algorithms," *Applied Optics*, 19(9):1505-1509, (1980).

Xia et al., "Engineering sub-100 nm multi-layer nanoshells," *Nanotechnology*, 17:5435-5440, (2006).

Xu, et al., "Unified Treatment of Fluorescence and Raman Scattering Processes near Metal Surfaces," *Physician Review Letters*, 93:1-4, (2004).

E. Prodan, et al., "A Hybridization Model for the Plasmon Response of Complex Nanostructures," *Science*, 302:419-422 (Oct. 17, 2003).

* cited by examiner

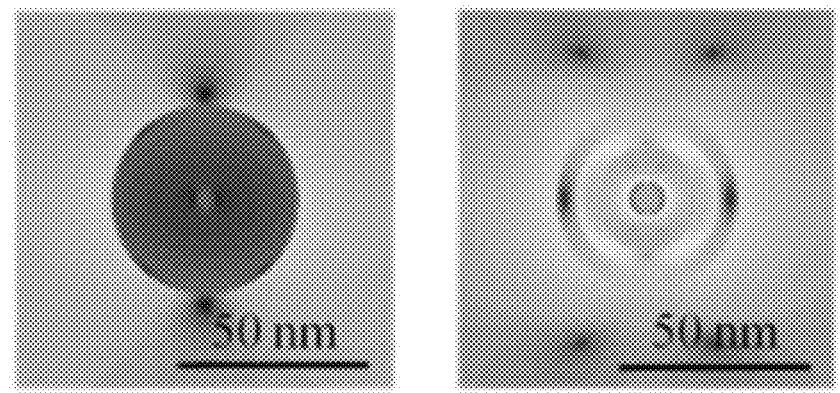
Log(Enhancement)
FIG. 10
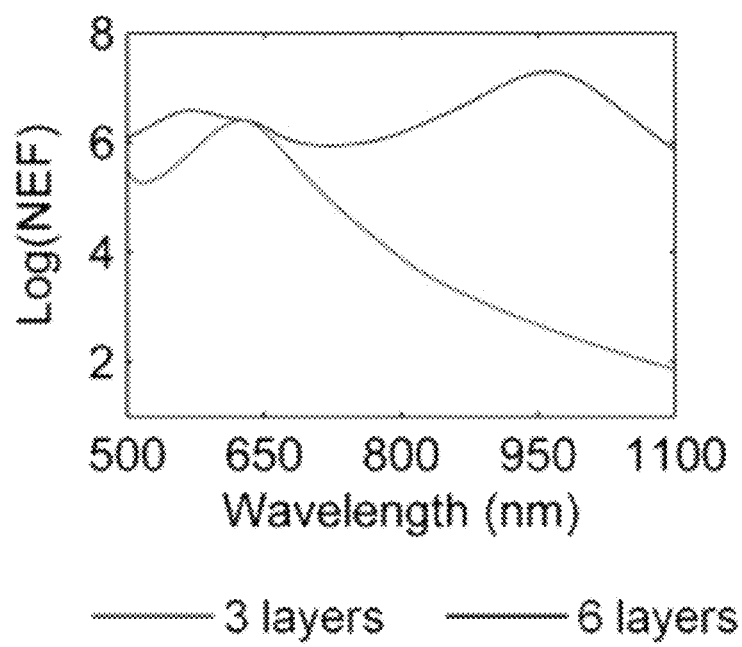
FIG. 11

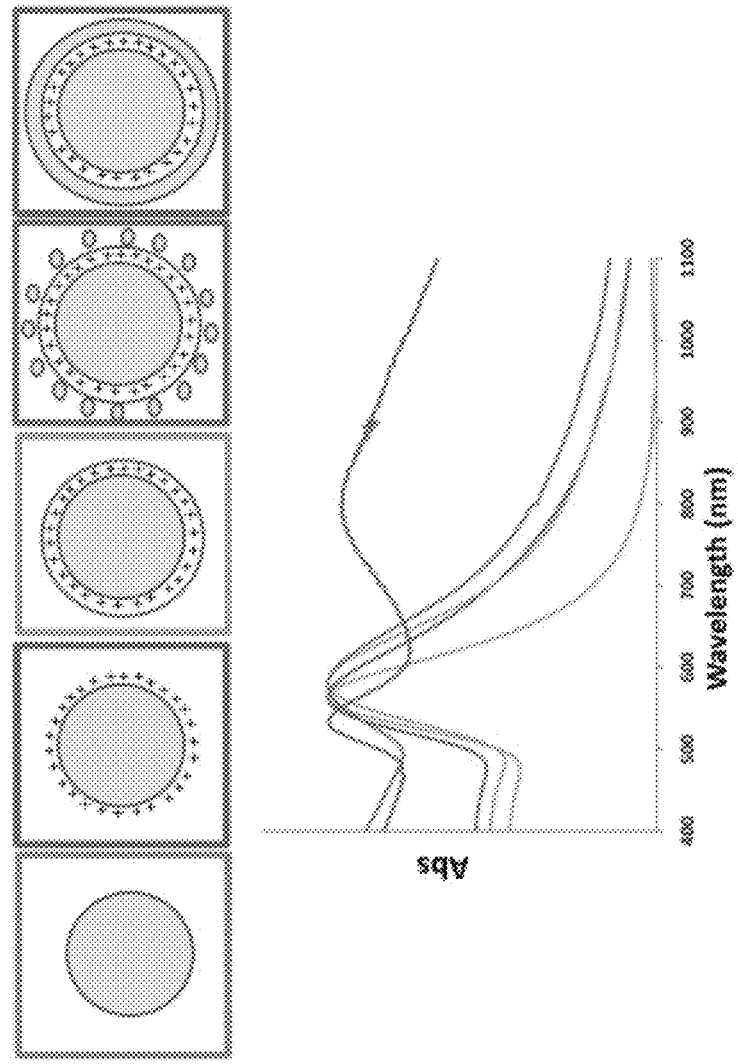

TAILORED RAMAN SPECTROCOPIC PROBES FOR ULTRASENSITIVE AND HIGHLY MULTIPLEXED ASSAYS

CROSS REFERENCE TO RELATED APPLICATION

This application claims the benefit of the earlier filing date of U.S. provisional application No. 61/407,233, filed Oct. 27, 2010, which is incorporated in its entirety herein by reference.

ACKNOWLEDGMENT OF GOVERNMENT SUPPORT

This invention was made with government support under Grant No. CHE 0957849 awarded by National Science Foundation. The government has certain rights in the invention.

FIELD

Embodiments of nanostructured, multilayered metal-dielectric particles suitable for use as Raman spectroscopic probes are disclosed, as well as methods of designing, making and using such nanoparticles.

BACKGROUND

Surface-enhanced, Raman-scattering (SERS)-based probes, consisting of nano-structured particles, are emerging for biomedical applications. The SERS effect is typically prominent in nanoscale metal-dielectric environments in which the signal of a proximal organic molecule can be rationally tailored and enhanced to the extent that single molecules may be detected. Hence, SERS probes typically contain nanoscale metallic structures and organic molecules that act as quantitative reporters for the presence of the probe.

The achieved enhancement depends on the reporters' molecular characteristics as well as nanoscale size, shape, geometry, local aggregation state and surface characteristics of the metal. These parameters can potentially be controlled to tune the reporter's signal, especially to maximize sensitivity of detection. Controlling and tuning the enhancement of the reporter's signal, however, is an ongoing challenge. Given the large number of factors influencing enhancement, designing particles for specific enhancement levels remains an active theoretical challenge while simultaneously controlling variability in their response remains a practical hurdle. Variability in SERS signal arises due to the synergistic effects of the metal's atomic mobility, surface reorganization and the reporter's molecular mobility. The net result is an unpredictable variation in enhancement, including blinking or "hotspots." The intractability of controlling enhancement has led to theorization of a "SERS-uncertainty principle"[1] and a practical choice between (a) unstructured colloids providing an exceptionally large but uncontrolled enhancement and uncertain spatial localization or (b) well-defined and controlled probes using self-assembling monolayer reporters but of substantially lower enhancement and limited reported diversity. While the utility of controlled nanostructures on making the SERS effect usable is not disputed, a rational framework to design SERS probes for a desired enhancement level, spectral selectivity, and size is lacking.

SUMMARY

Embodiments of nanostructured, multilayered metal-dielectric particles suitable for use as Raman spectroscopic probes are disclosed, as well as methods of designing, making and using such multilayered nanoparticles. Embodiments of kits including the multilayered nanoparticles also are disclosed.

In one embodiment, a method of designing a multilayered nanoparticle having alternating metal and dielectric layers and an outer dielectric shell includes (a) selecting parameters for the multilayered nanoparticle, the parameters comprising an overall diameter, a core diameter, a number of layers, a metal, a dielectric, thickness ranges for metal layers, thickness ranges for dielectric layers, and, optionally, a reporter molecule and a reporter molecule concentration; (b) storing the selected parameters in a database; (c) estimating, using a computer and based upon the selected parameters, field strengths for each layer; (d) comparing, using the computer, estimated field strengths with prior estimated field strengths to provide a comparison; (e) storing, using the computer, expansion coefficients; (f) selecting, using the computer, a weighting function from a database, wherein the weighting function is based on a power of an electric field strength; (g) applying, using the computer, the weighting function; (h) selecting, using the computer, at least one nanoshell structure; and (i) generating an output comprising a multilayered nanoparticle design based upon steps (a)-(h). In one embodiment, the metal is a transition metal. In another embodiment, the dielectric is silica. In one embodiment, the core diameter is at least 10 nm, each metal layer thickness is at least 2 nm, and each dielectric layer thickness is at least 1 nm.

In one embodiment, the nanoshell structure is selected based at least in part on its ability to produce Raman signal enhancement in a region proximal to the multilayered nanoparticle, e.g., a region extending up to 500 nm from an outer surface of the multilayered nanoparticle, when illuminated with an excitation wavelength. In another embodiment, the nanoshell structure is selected based at least in part on its ability to produce a region of Raman signal enhancement within the multilayered nanoparticle, such as within at least one dielectric layer other than the outer dielectric shell, when illuminated with an excitation wavelength. In one embodiment, the nanoshell structure is selected based at least in part on its ability to exhibit a net enhancement factor of from $10^{-3}$ to $10^{15}$.

In one embodiment, the nanoshell structure is selected based at least in part on its ability to produce a region of Raman signal quenching within the multilayered nanoparticle when illuminated with a first excitation wavelength. In another embodiment, the nanoshell structure is selected based at least in part on its further ability to produce a region of Raman signal enhancement within the multilayered nanoparticle when illuminated with a second excitation wavelength, wherein the first and second excitation wavelengths are not the same.

In one embodiment, a method for making a multilayered nanoparticle includes (1) providing a multilayered nanoparticle design; (2) providing a metal or dielectric core; (3) depositing a first layer onto the core by depositing a plurality of metal or dielectric seeds onto the core, wherein the seeds are (a) metal if the core is dielectric or (b) dielectric if the core is metal; (4) growing the plurality of metal or dielectric seeds into a continuous metal layer or dielectric layer, respectively; (5) depositing a plurality of alternating metal and dielectric layers onto the first layer by depositing a plurality of metal or dielectric seeds onto the first layer or a subsequent layer, and growing the plurality of metal or dielectric seeds into a continuous metal layer or dielectric layer, respectively; (6) repeating step (5) to produce a number of layers determined by the multilayered nanoparticle design. In one embodiment, the layers terminate with an outer metal layer, and the method further includes depositing a plurality of dielectric seeds onto the outer metal layer and growing the plurality of dielectric seeds into an outer dielectric shell. In one embodiment, the outer dielectric shell is silica.

In one embodiment, the method further includes functionalizing an outer surface of a dielectric core or a dielectric layer with a molecular linker comprising a first functional group capable of binding to the dielectric and a second functional group capable of binding to the metal before depositing the plurality of metal seeds. In some embodiments, the metal is a transition metal. In one embodiment, metal is gold, the dielectric is silica, and the molecular linker comprises an alkoxy silane group and a thiol or amino group, e.g., aminopropyl trimethoxysilane.

In one embodiment, the dielectric is silica and the dielectric seeds are methoxy-polyethylene glycol-thiol. In one embodiment, at least one dielectric layer further includes a plurality of reporter molecules. The reporter molecules may be added concurrently with the dielectric seeds.

In one embodiment, the multilayered nanoparticle includes 2-5 alternating metal and dielectric layers and terminates with an outer dielectric shell. In one embodiment, each metal layer has a thickness of at least 2 nm and each dielectric layer has a thickness of at least 1 nm.

In some embodiments, the multilayered nanoparticle further includes a plurality of reporter molecules embedded in at least one dielectric layer other than the outer dielectric shell. In one embodiment, the reporter molecules are present in a concentration of 1% by volume within the at least one dielectric layer. In another embodiment, reporter molecules are embedded in a plurality of dielectric layers other than the outer dielectric shell. The reporter molecules in each of the dielectric layers may have the same chemical composition, or the reporter molecules in a first dielectric layer may have a different chemical composition than reporter molecules in a subsequent dielectric layer.

The multilayered nanoparticle may have a region of signal enhancement localized to a dielectric layer or to a region proximal to the multilayered nanoparticle and extending up to 500 nm from an outer surface of the multilayered nanoparticle, or a region of signal quenching localized to a dielectric layer or to a region proximal to the multilayered nanoparticle and extending up to 500 nm from an outer surface of the multilayered nanoparticle, or a combination thereof.

Embodiments of the disclosed multilayered nanoparticles can be used to detect analytes in a sample. In one embodiment, a method for detecting analytes in a sample includes providing a first multilayered nanoparticle, combining a sample and the first multilayered nanoparticle under conditions sufficient to detect the first analyte, illuminating the sample with a first excitation wavelength capable of producing a Raman scattering peak at a wavelength characteristic of the first multilayered nanoparticle or the first analyte, and detecting the Raman scattering peak characteristic of the first multilayered nanoparticle or the first analyte, wherein the presence of the Raman scattering peak characteristic of the first multilayered nanoparticle or the first analyte indicates that the first analyte is present in the sample. In another embodiment, combining the sample and the first multilayered nanoparticle includes preparing a first probe by conjugating the first multilayered nanoparticle to a specific binding moiety capable of recognizing and binding to the first analyte, and combining the sample and the first probe under conditions sufficient to detect the first analyte.

In one embodiment, the first analyte has a first concentration, and the first multilayered nanoparticle has a structure that has a first unique Raman scattering peak and a first net enhancement factor when illuminated with a first excitation wavelength and has a subsequent unique Raman scattering peak and a subsequent net enhancement factor when illuminated with a subsequent excitation wavelength, and the method further includes 1) preparing a subsequent probe by conjugating the first multilayered nanoparticle to a subsequent specific binding moiety capable of recognizing and binding to a subsequent analyte, 2) combining the sample and the first probe under conditions sufficient to detect the first analyte, 3) illuminating the sample with the first excitation wavelength to produce the first unique Raman scattering peak, 4) detecting the first unique Raman scattering peak, wherein the presence of the first unique Raman scattering peak indicates that the first analyte is present in the sample, 5) combining the subsequent probe with the sample and the first probe under conditions sufficient to detect the subsequent analyte, 6) illuminating the sample with the subsequent excitation wavelength to produce the subsequent unique Raman scattering peak, and 7) detecting the subsequent unique Raman scattering peak, wherein the presence of the subsequent unique Raman scattering peak indicates that the subsequent analyte is present in the sample. In one embodiment, the first multilayered nanoparticle is selected based at least in part on a comparison of a ratio of the first and subsequent concentrations to a ratio of the first and subsequent net enhancement factors.

In another embodiment, the first multilayered nanoparticle includes a plurality of first reporter molecules embedded in a first dielectric layer and a plurality of subsequent reporter molecules embedded in a subsequent dielectric layer, wherein the first and subsequent reporter molecules have different chemical compositions, and the method further includes 1) preparing a subsequent probe by conjugating the first multilayered nanoparticle to a subsequent specific binding moiety capable of recognizing and binding to a subsequent analyte, 2) combining the sample, the first probe, and the subsequent probe under conditions sufficient to detect the first analyte and the subsequent analyte, 3) illuminating the sample with the first excitation wavelength thereby producing a first unique Raman scattering peak at a wavelength characteristic of the first reporter molecules and a subsequent unique Raman scattering peak at a wavelength characteristic of the subsequent reporter molecules, 4) detecting the first unique Raman scattering peak, wherein the presence of the first unique Raman scattering peak indicates that the first analyte is present in the sample, and 5) detecting the subsequent unique Raman scattering peak, wherein the presence of the subsequent unique Raman scattering peak indicates that the subsequent analyte is present in the sample.

In one embodiment, the method further includes 1) providing a subsequent multilayered nanoparticle for detecting a subsequent analyte, preparing a subsequent probe by conjugating the subsequent multilayered nanoparticle to a subsequent specific binding moiety capable of recognizing and binding to the subsequent analyte, 2) combining the sample, the probe, and the subsequent probe under conditions sufficient to detect the first analyte and the subsequent analyte, 3) illuminating the sample with an excitation wavelength capable of producing a first Raman scattering peak at a first wavelength characteristic of the first multilayered nanoparticle and a subsequent Raman scattering peak at a subsequent wavelength characteristic of the subsequent multilayered nanoparticle, wherein the first wavelength and the subsequent wavelength are at least 5 nm apart, 4) detecting the first Raman scattering peak, wherein the presence of the first Raman scattering peak indicates that the first analyte is present in the sample, and 5) detecting the subsequent Raman scattering peak, wherein the presence of the subsequent Raman scattering peak indicates that the subsequent analyte is present in the sample.

In one embodiment, the first multilayered nanoparticle has a plurality of first reporter molecules embedded in at least one dielectric layer other than the outer dielectric layer, the subsequent multilayered nanoparticle has a plurality of subsequent reporter molecules embedded in at least one dielectric layer other than the outer dielectric layer, and the first reporter molecules and the subsequent reporter molecules have different chemical compositions. In another embodiment, the first multilayered nanoparticle and the subsequent multilayered nanoparticle are substantially the same size. In yet another embodiment, the first multilayered nanoparticle and the subsequent multilayered nanoparticle have the same metal composition and the same dielectric composition. In another embodiment, the first multilayered nanoparticle and the subsequent multilayered nanoparticle are substantially the same size, have the same metal composition and the same dielectric composition, but differ in the number of layers. In another embodiment, the first multilayered nanoparticle and the subsequent multilayered nanoparticle are substantially the same size, have the same metal composition and the same dielectric composition, have the same number of layers, but differ in the thicknesses of the individual layers.

In another embodiment, the first analyte has a first concentration, the subsequent analyte has a subsequent concentration, the first multilayered nanoparticle has a first net enhancement factor when illuminated with the excitation wavelength, and providing the subsequent multilayered nanoparticle includes determining a ratio of the first concentration to the subsequent concentration, and selecting the subsequent multilayered nanoparticle based at least in part on a comparison of (a) the ratio of the first concentration to the subsequent concentration to (b) a ratio of the first net enhancement factor to a subsequent net enhancement factor of the subsequent multilayered nanoparticle when illuminated with the excitation wavelength.

In one embodiment, a kit includes one or more of the disclosed multilayered nanoparticles and instructions for using the multilayered nanoparticles to detect an analyte. In another embodiment, the multilayered nanoparticles are conjugated to a specific binding moiety capable of recognizing and binding to the analyte.

In one embodiment, a computer-readable medium includes instructions, which, when executed by a computer, cause the computer to (a) receive and store in a database input from a user, the input comprising parameters for a multilayered nanoparticle, the parameters comprising an overall diameter, a core diameter, a number of layers, a metal, a dielectric, thickness ranges for metal layers, thickness ranges for dielectric layers, and, optionally, a reporter molecule and a reporter molecule concentration, (b) estimate, based upon the parameters, field strengths for each layer, (c) compare estimated field strengths with prior estimated field strengths to provide a comparison, (d) store in the database expansion coefficients, (e) select a weighting function from a database, wherein the weighting function is based on a power of an electric field strength, (f) apply the weighting function, (g) select at least one nanoshell structure, and (h) generate an output comprising a multilayered nanoparticle design based upon steps (a)-(g).

The foregoing and other objects and features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 10 is a pair of images illustrating that a quenched, 3-layer nano-LAMP (left image) has a minimal NEF and an enhanced, 6-layer nano-LAMP (right image) has a maximal NEF; both nano-LAMPs have a 100-nm diameter.

FIG. 11 is a graph of log (NEF) versus wavelength, illustrating that a six-layered nano-LAMP (50 nm diameter) provides spectrally flat response, i.e., a similar signal at multiple frequencies, while maintaining a high level of enhancement compared to a three-layered nano-LAMP of the same size.

FIG. 38 is a series of UV-visible absorbance spectra obtained at each stage during the synthesis of a gold-silica nano-LAMP including a gold core with a silica layer containing embedded DTTC molecules and an outer gold layer.

DETAILED DESCRIPTION

Figures 1A, 1B, 1C, 1D, 1E:
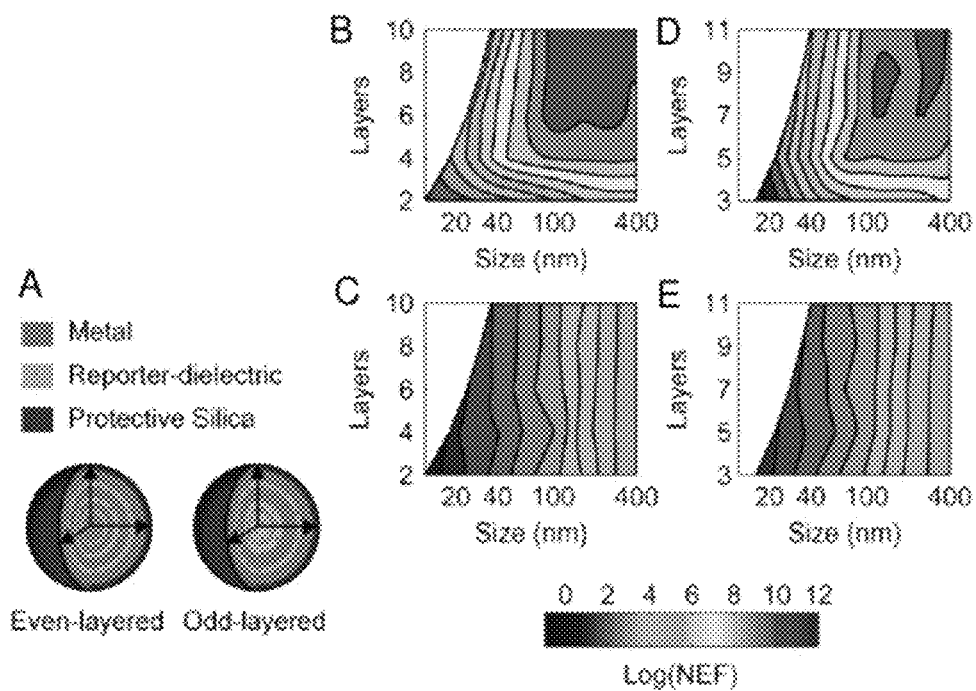
FIG. 1A illustrates the layer configurations for two embodiments of the disclosed nano-layered alternating metal-dielectric probes (nano-LAMPs) having an even number or an odd number of alternating metal and dielectric layers with an outer protective silica layer.
FIG. 1B is a graph illustrating the net enhancement factor (NEF) for embodiments of the disclosed nano-LAMPs having an even number of layers and varying diameters.
FIG. 1C is a graph illustrating the numerical enhancement for embodiments of the disclosed nano-LAMPs having an even number of layers and varying diameters.
FIG. 1D is a graph illustrating the net enhancement factor (NEF) for embodiments of the disclosed nano-LAMPs having an odd number of layers and varying diameters.
FIG. 1E is a graph illustrating the numerical enhancement for embodiments of the disclosed nano-LAMPs having an odd number of layers and varying diameters.

Disclosed herein are embodiments of surface-enhanced Raman scattering (SERS) probes with designed enhancement that can be tuned over a permissible range, wavelength-tuning capability, and/or potential for multi-wavelength excitation. Embodiments of the disclosed probes produce signals with reduced variability compared to conventional SERS probes. The disclosed probes also offer unlimited multiplexing capability using simple embedded reporter molecules. The use of virtually any desired reporter, tailored enhancement, and reproducible signal response will facilitate measuring multiple molecular species in complex samples. Certain embodiments of the disclosed probes enable a large dynamic range and/or suppression of the signal from the surrounding medium, both of which are limiting factors with conventional SERS probes.

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means "including A" or "including B" or "including A and B."

Suitable methods and materials for the practice and/or testing of embodiments of the disclosure are described below. Such methods and materials are illustrative only and are not intended to be limiting. Other methods and materials similar or equivalent to those described herein can be used. All publications, patent applications, patents, and other references mentioned herein are incorporated by reference in their entirety for all purposes, to the extent permissible by applicable rules and/or law.

In order to facilitate review of the various embodiments of the disclosure, the following explanations of specific terms are provided.

I. DEFINITIONS AND ABBREVIATIONS

Analyte: A molecule for which the presence, location and/or concentration is to be determined. Analytes include, but are not limited to, proteins (e.g., peptides, enzymes, antibodies, receptors, lectins, avidins such as streptavidins, protein A, receptors, peptide and protein hormones (e.g., insulin, gonadotropin, somatotropin)), nucleic acids (e.g., DNA sequences (including cDNA), RNA sequences, oligonucleotides, synthetic oligonucleotides, modified oligonucleotides, catalytic nucleic acids (e.g., a DNAzyme or RNAzyme), carbohydrates, polysaccharides, lipids, lipopolysaccharides, glycoproteins, lipoproteins, aminoglycans, phospholipids, nucleoproteins, non-peptide hormones, amino acids, toxins, metals, haptens, vitamins, small organic molecules (e.g., digoxin, heroin, cocaine, morphine, mesaline, lysergic acid, tetrahydrocannabinol, cannabinal, steroids, pentamindine, biotin), bacteria, and viruses. Exemplary analytes include proteins expressed by tumors, e.g., FGFR1 (GenBank Accession No. M34185), FGFR2 (GenBank Accession No. AK026508), FGFR3 (GenBank Accession No. M64347), FGFR4 (GenBank Accession No. AF202063), VEGFR-1 (GenBank Accession No. AF063657), VEGFR-2 (GenBank Accession No. AF035121), RET (GenBank Accession No. BC004257), EPHA1 (GenBank Accession No. M18391), EPHA2 (GenBank Accession No. BC037166), EPHA3 ((GenBank Accession No. M83941), EPHA4 (GenBank Accession No. L36645), EPHA5 (GenBank Accession No. L36644), EPHA6 (GenBank Accession No. AK092565), EPHA7 (GenBank Accession No. L36642), EPHA8 (GenBank Accession No. BC038796), EPHB (GenBank Accession No. L40636), EPHB2 (GenBank Accession No. AF025304), EPHB3 (GenBank Accession No. X75208), EPHB4 (GenBank Accession No. AY056047), EPHB6 (GenBank Accession No. D83492), INSR (GenBank Accession No. M10051), PDGFRA (GenBank Accession No. D50001), PDGFRB (GenBank Accession No. M21616), HGFR (GenBank Accession No. M35073), TrkA (GenBank Accession No. Y09028), TrkB (GenBank Accession No. AF410902), TrkC (GenBank Accession No. U05012), AXLr (GenBank Accession No. M76125), LTK (GenBank Accession No. D16105), TIE-1 (GenBank Accession No. BC038239), TIE-2 (GenBank Accession No. L06139), ROR1 (GenBank Accession No. M97675), ROR2 (GenBank Accession No. M97639), DDR1 (GenBank Accession No. X99031), PTK7 (GenBank Accession No. AF447176), RYK (GenBank Accession No. S59184), and MUSK (GenBank Accession No. AF006464). Exemplary mRNA analytes related to breast cancer risk and assessment include proliferation targets (e.g., Ki-67, STK15, Survivin, Cyclin B1, MYBL2), invasion targets (e.g., Stromelysin 3, Cathepsin L2), HER2 targets (e.g., HER2 (GenBank Accession No. NC_000017, nucleotides 35097919-35138441), GRB7), estrogen targets (e.g., ER, PGR, Bcl2, SCUBE2), and other targets (e.g., GSTM1, CD68, BAG1).

In some examples, an analyte is a protein from a virus or other microorganism associated with a disease or condition. A non-limiting, and far from exhaustive, list of viruses includes Adeno-associated virus, Adenovirus, Avian infectious bronchitis virus, Baculovirus, Chicken pox, Corona virus, Cytomegalovirus, Distemper, Enterovirus, Epstein Barr virus, Feline leukemia virus, Flavivirus, Foot and mouth disease virus, Hepatitis A, Hepatitis B, Hepatitis C, Hepatitis E, Herpes species, Herpes simplex, Influenza virus, HIV-1, HIV-2, HTLV 1, Influenza A and B, Kunjin virus, Lassa fever virus, LCMV (lymphocytic choriomeningitis virus), lentivirus, Measles, Mengo virus, Morbillivirus, Myxovirus, Papilloma virus, Parovirus, Parainfluenza virus, Paramyxovirus, Parvovirus, Poko virus, Polio virus, Polyoma tumour virus, pseudorabies, Rabies virus, Reovirus, Respiratory syncytial virus, retrovirus, rhinovirus, Rinderpest, Rotavirus, Semliki forest virus, Sendai virus, Simian Virus 40, Sindbis virus, SVS, Tick borne encephalitis virus, Togavirus (rubella, yellow fever, dengue fever), Vaccinia virus, Venezuelan equine encephalomyelitis, Vesicular stomatis virus, metapneumovirus, norovirus, SARS virus, smallpox virus, picornaviruses, varicella zoster, and West Nile virus.

Alternatively, the analyte may be a bacterial protein. Exemplary bacterial proteins include those of *Achromobacter xylosoxidans*, *Acinetobacter calcoaceticus*, preferably *A. anitratus*, *A. haemolyticus*, *A. alcaligenes*, and *A. lwoffii*, *Actinomyces israelii*, *Aeromonas hydrophilia*, *Alcaligenes* species, preferably *A. faecalis*, *A. odorans* and *A. denitrificans*, *Arizona hinshawii*, *Bacillus anthracis*, *Bacillus cereus*, *Bacteroides fragilis*, *Bacteroides melaminogenicus*, *Bordetella pertussis*, *Borrelia burgdorferi*, *Borrelia recurrentis*, *Brucella* species, preferably *B. abortus*, *B. suis*, *B. melitensis* and *B. canis*, *Calymmatobacterium granulomatis*, *Campylobacter coli* (e.g., the CjaA polypeptide), *Campylobacter fetus* ssp. intestinalis, *Campylobacter fetus* ssp. jejuni, *Chlamydia* species, preferably *C. psittaci* and *C. trachomatis*, *Chromobacterium violaceum*, *Citrobacter* species, preferably *C. freundii* and *C. diversus*, *Clostridium botulinum*, *Clostridium perfringens*, *Clostridium difficile*, *Clostridium tetani*, *Corynebacterium diphtheriae*, *Corynebacterium*, preferably *C. ulcerans*, *C. haemolyticum* and *C. pseudotuberculosis*, *Coxiella burnetii*, *Edwardsiella tarda*, *Eikenella corrodens*, *Enterobacter*, preferably *E. cloacae*, *E. aerogenes*, *E. hafniae* (also named *Hafnia alvei*) and *E. agglomerans*, *Erysipelothrix rhusiopathiae*, *Escherichia coli*, *Flavobacterium meningosepticum*, *Francisella tularensis*, *Fusobacterium nucleatum*, *Gardnerella vaginalis*, *Haemophilus ducreyi*, *Haemophilus influenzae*, *Helicobacter* species (e.g., the UreB polypeptide of *H. pylori*), *Klebsiella* species, preferably *K. pneumoniae*, *K. ozaenae og K. rhinoscleromatis*, *Legionella* species, *Leptospira interrogans*, *Listeria monocytogenes*, *Moraxella* species, preferably *M. lacunata and M. osloensis*, *Mycobacterium bovis*, *Mycobacterium leprae*, *Mycobacterium tuberculosis* (e.g., the CFP10 polypeptide), *Mycoplasma* species, preferably *M. pneumoniae*, *Neisseria gonorrhoeae*, *Neisseria meningitidis*, *Nocardia* species, preferably *N. asteroides* and *N. brasiliensis*, *Pasteurella haemolytica*, *Pasteurella multocida*, *Peptococcus magnus*, *Plesiomonas shigelloides*, *Pneumococci*, *Proteus* species (such as *P. mirabilis*, *P. vulgaris*, *P. rettgeri* and *P. morganii* (also named *Providencia rettgeri* and *Morganella morganii* respectively), *Providencia* species (e.g., *P. alcalifaciens*, *P. stuartii* and *P. rettgeri* (also named *Proteus rettgeri*)), *Pseudomonas aeruginosa*, *Pseudomonas mallei*, *Pseudomonas pseudomallei*, *Rickettsia*, *Rochalimaia henselae*, *Salmonella* species (such as *S. enteridis*, *S. typhi* and *S. derby*, and *Salmonella* DT104), *Serratia* species (e.g., *S. marcescens*), *Shigella dysenteriae*, *S. flexneri*, *S. boydii* and *S. sonnei*, *Spirillum minor*, *Staphylococcus aureus*, *Staphylococcus epidermidis*, *Staphylococcus saprophyticus*, *Streptobacillus moniliformis*, *Streptococcus* (e.g., *S. faecalis*, *S. faecium*, *S. durans*, *S. agalactiae*, *S. pneumoniae*, *S. pyogenes* (e.g., the Sfb1 polypeptide)), *Treponema carateum*, *Treponema pallidum*, *Treponema pertenue*, *Ureaplasma urealyticum*, *Vibrio cholerae*, *Vibrio parahaemolyticus*, *Yersinia enterocolitica*, and *Yersinia pestis*.

Parasitic proteins may be from Malaria (*Plasmodium falciparum*, *P. vivax*, *P. malariae*), Schistosomes, Trypanosomes, Leishmania, Filarial nematodes, Trichomoniasis, Sarcosporidiasis, Taenia (*T. saginata*, *T. solium*), Leishmania, Toxoplasma gondii, Trichinelosis (*Trichinella spiralis*) or Coccidiosis (Eimeria species).

Illustrative fungal proteins may be from *Cryptococcus neoformans*, *Candida albicans*, *Aspergillus fumigatus* or *Coccidioidomycosis*.

Antibody: Collectively refers to immunoglobulins or immunoglobulin-like molecules [including by way of example and without limitation, IgA, IgD, IgE, IgG and IgM, combinations thereof, and similar molecules produced during an immune response in any chordate such as a vertebrate, for example, in mammals such as humans, goats, rabbits and mice] and fragments thereof that specifically bind to a molecule of interest (or a group of highly similar molecules of interest) to the substantial exclusion of binding to other molecules. An "antibody" typically comprises a polypeptide ligand having at least a light chain or heavy chain immunoglobulin variable region that specifically recognizes and binds an epitope of an antigen. Immunoglobulins are composed of a heavy and a light chain, each of which has a variable region, termed the variable heavy ($V_H$) region and the variable light ($V_L$) region. Together, the $V_H$ region and the $V_L$ region are responsible for binding the antigen recognized by the immunoglobulin. Exemplary immunoglobulin fragments include, without limitation, proteolytic immunoglobulin fragments [such as F(ab')$_2$ fragments, Fab' fragments, Fab'-SH fragments and Fab fragments as are known in the art], recombinant immunoglobulin fragments (such as sFv fragments, dsFv fragments, bispecific sFv fragments, bispecific dsFv fragments, F(ab)'$_2$ fragments, single chain Fv proteins ("scFv"), and disulfide stabilized Fv proteins ("dsFv").

Other examples of antibodies include diabodies, and triabodies (as are known in the art), and camelid antibodies. "Antibody" also includes genetically engineered molecules, such as chimeric antibodies (for example, humanized murine antibodies), and heteroconjugate antibodies (such as, bispecific antibodies). See also, *Pierce Catalog and Handbook,* 1994-1995 (Pierce Chemical Co., Rockford, Ill.); Kuby, J., *Immunology,* 3$^{rd}$ Ed., W.H. Freeman & Co., New York, 1997.

Binding: An association between two substances or molecules, such as the hybridization of one nucleic acid molecule to another (or itself), the binding of an antibody to its antigen, or the binding of an enzyme to its substrate. One molecule is said to "specifically bind" to another molecule when a particular agent, i.e., a specific binding agent or specific binding moiety, can specifically interact with a particular analyte. The binding is a non-random binding reaction, for example between an oligonucleotide (such as a functional nucleic acid) and its complementary sequence. In particular examples, two compounds are said to specifically bind when the binding constant for complex formation between the components exceeds about $10^4$ L/mol, for example, exceeds about $10^6$ L/mol, exceeds about $10^8$ L/mol, or exceeds about $10^{10}$ L/mol. The binding constant for two components can be determined using methods that are well known in the art.

Exemplary specific binding moieties include, by way of example and without limitation, antibodies, antibody fragments, proteins (including lectins, receptors, effectors, enzymes), peptides, amino acids, enzyme co-factors, enzyme inhibitors, nucleosides, nucleotides, nucleotide chains, nucleic acids, DNA, cDNA, RNA, mRNA, peptide nucleic acids, and aptamers.

Conditions sufficient to detect: Any environment that permits the desired activity, for example, an environment that brings a nano-LAMP and an analyte into proximity or that permits a probe to bind an analyte and the interaction to be detected. For example, such conditions include appropriate temperatures, buffer solutions, and detection means such as a Raman spectroscope and/or digital imaging equipment.

Conjugate: As used herein, a conjugate is a compound that includes a nanoparticle, such as a nano-LAMP, and one or more specific binding moieties effectively coupled to the nanoparticle, either directly or indirectly, by any suitable means. For example, the specific binding moiety can be covalently or noncovalently (e.g., electrostatically) coupled to the nanoparticle.

Detect: To determine if an analyte (such as an antigen, protein or nucleic acid) is present or absent, for example, in a sample. In some examples, this can further include quantification. "Detecting" refers to any method of determining if something exists, or does not exist, such as determining if an analyte is present in a sample, such as a biological sample. In certain examples, detection refers to observing and/or quantifying a signal observable using Raman spectroscopy.

Dielectric: Refers to a substance with very low electrical conductivity, e.g., an electrical conductivity of less than $10^{-6}$ mho/cm, but high polarizability. Dielectric materials are electrical insulators that can be polarized by an applied electric field. Electric charges do not flow through the material, but only shift slightly from their equilibrium positions, resulting in polarization and creation of an internal electric field. Exemplary solid dielectrics include silica, porcelain, mica, most polymers, and some metal oxides (e.g., transition metal and lanthanide metal oxides, such as iron oxide, copper oxide, or titanium dioxide).

Electromagnetic radiation: A series of electromagnetic waves that are propagated by simultaneous periodic variations of electric and magnetic field intensity, and that includes radio waves, infrared, visible light, ultraviolet light, X-rays and gamma rays.

Excitation or excitation signal: The light of a particular wavelength necessary and/or sufficient to excite an electron transition to a higher energy level. In particular examples, an excitation signal is the light of a particular wavelength necessary and/or sufficient to light induces waves of surface-confined collective electron oscillations in a nanoparticle, e.g., a nano-LAMP.

LAMP: Layered alternating metal-dielectric probe.

Multiplex, -ed, -ing: Detection of multiple analytes in a sample substantially simultaneously, or sequentially, as desired. Multiplexing can include identifying and/or quantifying nucleic acids generally (e.g., DNA or RNA), peptides, proteins, both individually and in any and all combinations.

nano-LAMP: A layered alternating metal-dielectric probe having a diameter of less than 1 micron, e.g., 10 nm to 500 nm, such as from 20 nm to 400 nm, 20 nm to 100 nm, 50 nm to 100 nm, 50 nm, 100 nm, or less than or equal to 100 nm.

Nanoparticle: A nanoscale particle with a size that is measured in nanometers, for example, a nanoscopic particle that has at least one dimension of less than 1 micron, such as less than 500 nm, less than 250 nm, or less than or equal to 100 nm.

Plasmon: A quasiparticle resulting from the quantization of plasma oscillations. Surface plasmons are plasmons confined to a surface. They can occur at the interface of a material with a positive dielectric constant, and a negative dielectric constant.

Plasmon resonance: The excitation of plasmons by light.

Probe: As used herein, a probe includes a specific binding moiety conjugated to a nano-LAMP. The specific binding moiety allows the probe to recognize and bind to an analyte of interest.

Proximal: As used herein, proximal means "in the vicinity of," e.g., in the vicinity of a nano-LAMP. In one example, proximal means within 500 nm of the nano-LAMP's outer surface, such as within 250 nm, within 100 nm within 50 nm, within 10 nm, or within 5 nm of nano-LAMP.

Quantum dot: A nanoscale particle that exhibits size-dependent electronic and optical properties due to quantum confinement. Quantum dots have, for example, been constructed of semiconductor materials (e.g., cadmium selenide and lead sulfide) and from crystallites (grown via molecular beam epitaxy), etc. A variety of quantum dots having various surface chemistries and fluorescence characteristics are commercially available from Invitrogen Corporation, Eugene, Oreg. Quantum dots are also commercially available from Evident Technologies (Troy, N.Y.). Other quantum dots include alloy quantum dots such as ZnSSe, ZnSeTe, ZnSTe, CdSSe, CdSeTe, ScSTe, HgSSe, HgSeTe, HgSTe, ZnCdS, ZnCdSe, ZnCdTe, ZnHgS, ZnHgSe, ZnHgTe, CdHgS, CdHgSe, CdHgTe, ZnCdSSe, ZnHgSSe, ZnCdSeTe, ZnHgSeTe, CdHgSSe, CdHgSeTe, InGaAs, GaAlAs, and InGaN quantum dots.

Quenching: A decrease in intensity or elimination of a detectable signal, e.g., a signal detectable by Raman spectroscopy.

Reporter molecule: As used herein, a reporter molecule is a molecule that exhibits detectable Raman signals. Typically, reporter molecules are organic compounds and quantum dots. Suitable organic compounds may include olefin or alkyne moieties. Exemplary reporter molecules include, but are not limited to, organic dyes, e.g., isothiocyanate dyes, thiacyanine dyes, dithiacyanine dyes, thiacarbocyanine dyes, dithiacarbocyanine dyes, multi-sulfur organic dyes, multi-heterosulfur organic dyes, benzotriazole dyes. Exemplary reporter molecules include rhodamine 6G, rhodamine-5-isothiocyanate, X-rhodamine-6-isothiocyanate, tetramethylrhodamine-5-isothiocyanate, DTDC (3,3'-diethylthiadicarbocyanine iodide), DTTC (3,3' diethylthiatricarbocyanine iodide), DTC (3,3'-diethylthiacyanine iodide), DTCC (3,3' diethylthiacarbocyanine iodide), 3,3'-diethyl-9-methylthiacarbocyanine iodide, 1,1'-diethyl-2,2'-quinotricarbocyanine iodide, eosin-5-isothiocyanate, erythrosin-5-isothiocyanate, FITC (fluorescein isothiocyanate), 488 isothiocyanate, malachite green isothiocyanate, Oregon Green®, 4,4'-diiothiocyanatodihydrostilbene-2,2'-disulfonic acid, disodium salt, 4,4'-diisothiocyanatostilbene-2,2'-disulfonic acid, disodium salt, N-(4-(6-dimethylamino-2-benzofuranyl)phenylisothiocyanate, 7-dimethylamino-4-methylcoumarin-3-isothiocyanate, (S)-1-p-isothiocyanatobenzyldiethylene-triaminepentaacetic acid, azobenzotriazoyl-3,5-dimethoxyphenylamine, dimethoxy-4-(6'-azobenzotriazolyl)phenol, 4-mercaptopyridine, dithiobisbenzonic acid (DBA), 4-mercaptobenzoic acid (MBA), 2-naphthalenethiol (NT), thiophenol (TP), direct red 81, Chicago sky blue, 4,4'-dithiobis(succinimidylbenzoate) (DSB), p-dimethylaminoazobenzene, 1,5-difluoro-2,4-dinitrobenzene, 4-(4-aminophenylazo)phenylarsonic acid monosodium salt, arsenazo I, basic fuchsin, disperse orange 3, HABA (2-(4-hydroxyphenylazo)-benzoic acid, erythrosine B, trypan blue, ponceau S, ponceau SS, 5,5'-dithiobis(2-nitrobenzoic acid), metal complexes and polymeric particles.

Sample: The term "sample" refers to any liquid, semi-solid or solid substance (or material) in or on which an analyte can be present. In some examples, a sample can be a biological sample or a sample obtained from a biological material. A biological sample is any solid or fluid sample obtained from, excreted by or secreted by any living organism, including without limitation, single celled organisms, such as bacteria, yeast, protozoans, and amoebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease). A biological sample can also be a sample obtained from any organ or tissue (including a biopsy or autopsy specimen, such as a tumor biopsy) or can include a cell (whether a primary cell or cultured cell) or medium conditioned by any cell, tissue or organ. In another example, the sample is an environmental sample, such as air, water, or soil, or a sample obtained by contacting a surface (e.g., by swabbing a surface). In yet another example, the sample is a food sample.

SERS: Surface-enhanced Raman scattering or surface-enhanced Raman spectroscopy. SERS is a form of Raman spectroscopy that involves Raman-active molecules adsorbed to or interacting in some manner with metal surfaces. Conventional SERS techniques may produce spectral enhancements of $10^5$-$10^6$ orders of magnitude compared to normal Raman scattering.

II. NANO-LAYERED ALTERNATING METAL-DIELECTRIC PROBES

A. General Structure

Disclosed herein are surface-enhanced Raman scattering (SERS) probes. The disclosed SERS probes are multishell spheres comprising alternating metal and dielectric layers surrounding a metal or dielectric core (FIG. 1A). The multishell sphere can be considered to a spherically symmetric class of nano-layered alternating metal-dielectric probes, referred to herein as "nano-LAMPs." In one embodiment, a nano-LAMP comprises a dielectric core and two or more surrounding shells of alternating metal and dielectric layers, with the innermost shell being metal. In another embodiment, a nano-LAMP comprises a metal core and two or more surrounding shells of alternating metal and dielectric layers, with the innermost shell comprising a dielectric material. The nano-LAMP's spherical symmetry provides enhancement uniformity with respect to the direction of illuminating radiation and facilitates fabrication.

In some embodiments, the metal layers comprise a transition metal, e.g., gold, silver, copper, chromium, zinc, nickel, cadmium, or iron. In certain embodiments, the transition metal is silver, gold, or copper. Suitable dielectric materials include silica, polymers, and metal oxides.

In some embodiments, a nano-LAMP has a diameter from 10 nm to 500 nm, such as from 20 nm to 400 nm, 20 nm to 100 nm, 50 nm to 100 nm, 50 nm, 100 nm, or less than or equal to 100 nm. In certain embodiments, the core has a diameter of at least 10 nm, such as 10 nm to 80 nm, 15 nm to 70 nm, or 20 nm to 50 nm. In some embodiments, each metal layer has a thickness of at least 2 nm, at least 5 nm, at least 10 nm, 2 nm to 50 nm, 5 nm to 30 nm, 10 nm to 25 nm, 10 nm to 15 nm, 10 nm, 15 nm, 20 nm, or 25 nm. In certain embodiments, each dielectric layer has a thickness of at least 1 nm, at least 5 nm, at least 10 nm, 1 nm to 50 nm, 5 nm to 30 nm, 5 nm to 25 nm, 10 nm to 20 nm, 5 nm to 10 nm, 5 nm, 10 nm, 15 nm, or 20 nm. In some embodiments, a nano-LAMP comprises from 2 to 15 layers (including the core), such as from 3 to 11 layers, 2 to 10 layers, 3 to 5 layers, or 3 to 6 layers.

In some embodiments, reporter molecules are embedded in one or more dielectric layers surrounding the core. Embedding the reporter molecules in a dielectric layer eliminates the need for surface attachment and permits almost any molecule to be used as a reporter. In one embodiment, the reporter molecules are resonant at one or more frequencies typically used for Raman spectroscopy. In another embodiment, the reporter molecules are non-resonant at one or more frequencies typically used for Raman spectroscopy. Typically, reporter molecules are organic molecules, such as organic dyes, or may be inorganic molecules such as quantum dots. Suitable organic dyes include isothiocyanate dyes, thiacyanine dyes, dithiacyanine dyes, thiacarbocyanine dyes, dithiacarbocyanine dyes, multi-sulfur organic dyes, multi-heterosulfur organic dyes, and benzotriazole dyes.

In some embodiments, the reporter molecules have a molecular volume of at least 0.3 nm³, or at least 0.5 nm³, such as 0.3-0.7 nm³, 0.4-0.6 nm³, or 0.5 nm³. In some embodiments, the reporter molecules are present at a concentration of 0.5-1.5% by volume in at least one dielectric layer. In some examples, the reporter molecules have a concentration of at least 0.6%, at least 0.7%, at least 0.8%, or at least 1%, such as 0.6-1.4%, 0.7-1.3%, 0.8-1.2%, 0.9-1.1%, or 1% by volume. Maintaining a relatively low concentration of reporter molecules within the dielectric layer minimizes surface contact between reporter molecules and an adjacent metal layer.

In some embodiments, reporter molecules are included in a plurality of dielectric layers other than the outer silica shell. In one embodiment, the reporter molecules in each of the plurality of dielectric layers have the same chemical composition. In another embodiment, the reporter molecules in one dielectric layer do not have the same chemical composition as the reporter molecules in another dielectric layer.

Some embodiments of the SERS probes have a protective outer silica shell. The outer silica shell provides biocompatibility and shields biological materials from the potentially toxic effects of the probe materials (e.g., the metal and reporter molecules). In certain embodiments, the outer shell also shields molecules outside the probe from enhancement. Since the spectra of the surroundings are not enhanced and/or altered, the analyte is detected via probe transduction alone. Because the outer shell has a fixed composition and is dielectric, nano-LAMPs with an odd number of layers have a dielectric core while nano-LAMPs with an even number of layers have a metal core. In particular embodiments, the outer shell is devoid of reporter molecules.

B. Electromagnetic, Chemical, and Numerical Enhancement

Embodiments of the disclosed SERS probes have controlled enhancement and exceptional multiplexing capability. The spherical nano-LAMPs advantageously produce a directionally invariant response. The overall size of the nano-LAMPs, the number of layers surrounding the core, and/or thicknesses of individual layers are variables affecting the magnitude of SERS enhancement.

In modeling probes to tailor SERS enhancement, two mechanisms—electromagnetic and chemical—are generally invoked. Electromagnetic enhancement (EE) is well understood, and is usually larger than chemical enhancement (CE). CE mechanisms continue to be a subject of much research. Since the EE is larger, it is beneficial to focus on it in designing SERS probes.

In general, high EE is observed for reporter molecules confined between metal domains, i.e., reporters embedded in a dielectric layer. The dielectric embedment shields reporter molecules from direct contact with the metal surfaces and reduces CE to negligible levels. Consequently, signal enhancements are determined by electromagnetic effects alone. Without being bound by any particular theory of operation, it is believed that alternating dielectric and metal shells around a metal sphere may produce a high EE effect at the core surface, and alternating metal and dielectric shells around a dielectric core may lead to high EE effect at the shell surfaces.

Even if there were no SERS enhancement within the probe, a simple numerical enhancement (NE) would still result as a large number of reporter molecules could be placed within the probe for every analyte molecule. The enhancement observed with embodiments of the disclosed nano-LAMPs, however, arises from the sum of the surface enhanced signal arising from every reporter molecule in the probe. To quantify signal enhancement, a net enhancement factor (NEF) can be utilized, where the NEF is the ratio of a probe's total Raman signal to that of a single analyte molecule. Without loss of generality, we can assume that the analyte and unenhanced reporter have equivalent spectra and do not consider resonance Raman enhancement (RRE). Assuming that the reporter is uniformly distributed in the dielectric layers at low concentration, the NEF is defined by the volumetric integral as:

$$NEF=\iiint |E_{Raman}(\omega_S)|^2 |E_{loc}(\omega_o)|^2 c_r dV, \quad (1)$$

where $E_{Raman}$ is the electric field at the shifted frequency $\omega_s$, $E_{loc}$ is the field at the incident laser frequency $\omega_o$, $c_r$ is the concentration of reporter, and V is the volume of the dielectric-reporter. A low concentration of the reporter reduces the NEF, but is minimizes or prevents variability arising from surface adsorption of reporter molecules.

The EE for each reporter molecule scales as $G=|E_{Raman}(\omega_S)|^2|E_{loc}(\omega_o)|^2 \approx |E_{loc}|^4$. Hence, the task is reduced to determining the local electric field at all locations within the probe, which is calculated using Mie theory for multilayered spheres as detailed below in section IIIA.

For a given nano-LAMP size, thinner metal shells allow larger dielectric shells (and higher reporter loading). Thin metal shells, however, result in a smaller mean free path for electrons that dampens and broadens the surface plasmon resonances, producing a smaller EE. Thicker metal shells result in higher fields (larger EE) but smaller dielectric volumes (lower reporter loading) and higher metal absorption losses. The ultimate constraints on shell sizes further are determined by fabrication limits of nanostructures. The problem of determining enhancement for any LAMP structure is, thus, bounded. In some embodiments, genetic algorithms (GA) are utilized to systematically maximize and minimize the enhancement of probes of different diameters and at different excitation wavelengths as detailed below in section IIIB.

Each LAMP size can have even or odd layers. The thickness of any given layer in an optimized structure depends on the overall configuration of the LAMP and is selected to maximize the counteracting effects arising from coupled plasmonic interactions and reporter loading. NEFs depend on both the total probe size (R) and the number of layers (L) for odd or even-layered nano-LAMPs, as shown in FIGS. 1B and 1D. The contribution of reporter loading, or numerical enhancement (NE), is linear as shown in FIGS. 1C and 1E, and is much lower than the overall NEF. Hence, the enhanced probe signal arises primarily from the EE and not simply from more reporters per analyte. From FIGS. 1B and 1D, it can be seen that the enhancement in signal achieves a plateau (for 785 nm excitation) when a silver-silica nano-LAMP has a diameter of ~100 nm.

C. Enhancement Distribution and Dynamic Range

Figure 2:
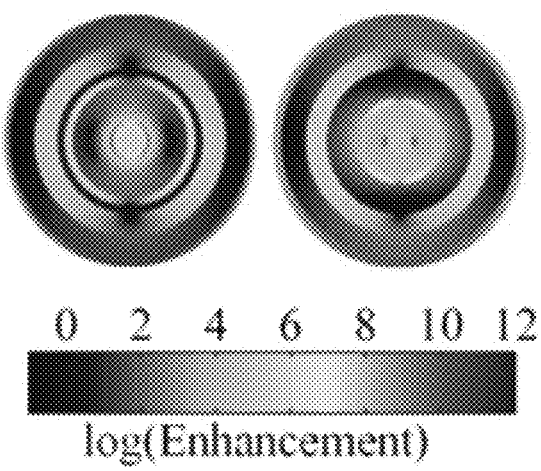
FIG. 2 is two images illustrating enhancement distributions in the incident plane of illumination for an even-layered silica-silver nano-LAMP and an odd-layered silica-silver nano-LAMP.
Figure 3:
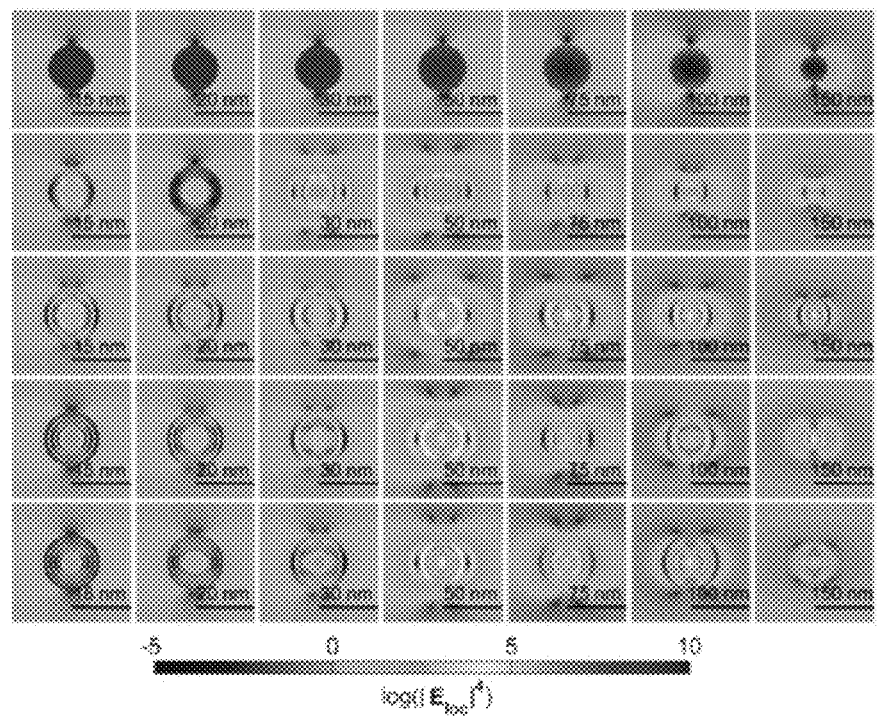
FIG. 3 is a series of images illustrating enhancement distributions in the incident plane of illumination for even-layered silica-silver nano-LAMPs of various configurations that are designed to maximize enhancements at an excitation wavelength of 785 nm. From top to bottom, the number of layers increases from 2 to 10; from left to right, the total size increases as shown.
Figure 4:
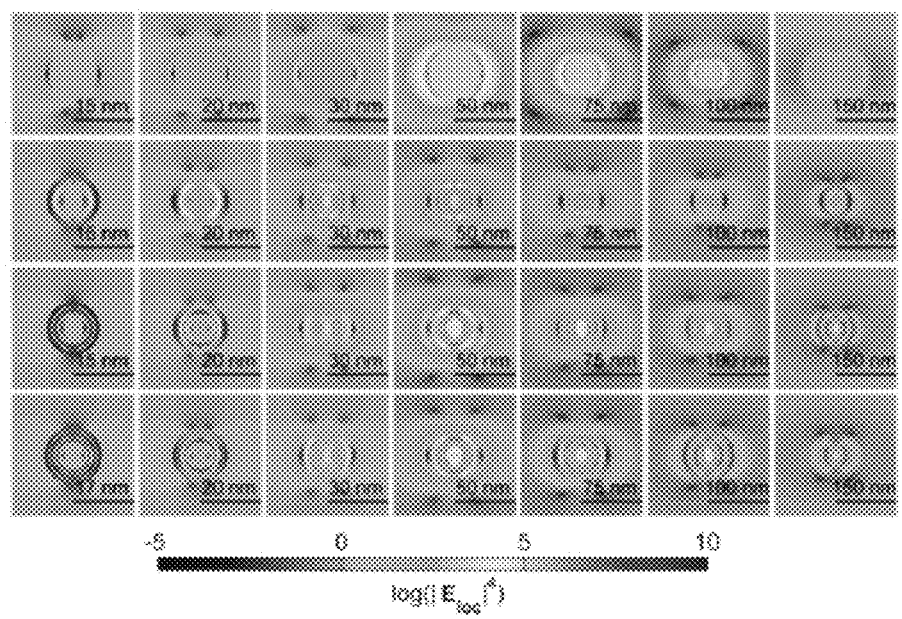
FIG. 4 is a series of images illustrating enhancement distributions in the incident plane of illumination for odd-layered silver-silica nano-LAMPs of various configurations that are designed to maximize enhancements at an excitation wavelength of 785 nm. From top to bottom, the number of layers increases from 3 to 9; from left to right, the total size increases as shown.

The enhancement distribution within nano-LAMPs (FIGS. 2-4) indicates that the structure reorganizes the surface plasmons to create local hot spots with a high NEF density at the core and appreciable contributions from elsewhere. While there is some contribution from the increased loading of reporter molecules (FIGS. 1C and 1E), it is the interplay of molecular and plasmon density that determines the NEF. Interestingly, enhancement beyond this critical size is not predicted to improve by the complexity of additional layers or loading. The desired probe size, however, may depend at least in part on the application and may be determined by considerations of fabrication, toxicity and/or uptake. For example, in human cervical cancer cells, 50-nm sized gold spheres were found to be taken up more quickly compared to other sizes in 10-100 nm range.[2]

Some embodiments of the disclosed nano-LAMPs comprising non-resonant organic reporters are capable of producing NEFs of up to $10^{12}$. This availability is substantially higher than that encountered in using SAMs (self-assembled monolayers) for consistent CE or resonant dyes in simple geometries. The elimination of CE is counter-intuitive and would likely have been detrimental to enhancement, but the inventors surprisingly discovered that structuring the probe as disclosed herein balances the loss in CE by enabling higher EE. Advantageously, the disclosed nano-LAMPs produce a consistent probe response without the constraints of using reporter molecules capable of forming SAMs and/or reporter molecules that are resonant at the excitation frequency. Removing these two constraints considerably enhances the multiplexing capability of SERS probes as almost any organic molecule is enabled to be used as a reporter and can be used to provide desired enhancements, subject only to the constraints in FIGS. 1B-1F.

Further increases beyond the upper limits of FIGS. 1B-1F can be achieved using resonant reporter molecules. For example, a NEF of ~$10^8$ is attained at 785 nm excitation for a silver-silica probe of 50-nm diameter by using 4 layers and a non-resonant reporter. However, when a dye that is resonant at the same excitation frequency is used as a reporter molecule, NEFs of ~$10^{14}$-$10^{15}$ are achieved. These are levels that allow for assaying analytes at a single molecule level. Hence, certain embodiments of the disclosed nano-LAMPs provide single-molecule sensitivity for analytes. Some embodiments of the disclosed nano-LAMPs have an NEF of up to $10^{16}$, such as up to $10^{15}$, up to $10^{14}$, up to $10^{12}$, up to $10^{10}$, up to $10^6$, or up to $10^3$.

Measuring multiple epitopes in biological samples often includes measuring analytes over a large concentration range. Hence, it is advantageous to devise a large dynamic range, i.e., a set of nano-LAMPs suitable for detecting analytes of widely differing concentrations in a single assay. When detecting abundant analytes, it may be desirable to quench or minimize the Raman signal to attenuate the probe response. Thus, the response of a particularly abundant analyte can be reduced while the response of a sparse analyte can be enhanced to measure both on the same platform and during the same experiment.

For example, it may be desirable to detect a first analyte having a concentration in the range of mg/mL in the same assay as a second analyte having a concentration in the range of pg/mL. The two analytes differ in concentration by a magnitude of $10^9$. To detect both analytes in the same assay, nano-LAMPs may be designed for each analyte to produce signals of comparable intensity. Thus, a nano-LAMP for the first analyte may have a NEF of 1, whereas a nano-LAMP for the second analyte may have a NEF of $10^8$-$10^{10}$. Alternatively, a nano-LAMP may be designed to minimize the signal from the first analyte relative to the signal from the second analyte. Thus, a nano-LAMP for detecting the first analyte may have a NEF of $10^{-3}$, whereas a nano-LAMP for the second analyte may have a NEF of $10^6$. In another embodiment, a single nano-LAMP demonstrating signal quenching at a first excitation wavelength and signal enhancement at a second excitation wavelength may be suitable for detecting both analytes. In another embodiment, a nano-LAMP comprising a plurality of first reporter molecules in a first dielectric layer and a plurality of second reporter molecules in a second dielectric layer, wherein the first and second reporter molecules have different chemical compositions and produce spectra with different characteristic wavelengths when illuminated by different excitation wavelengths, also may be suitable. In such an embodiment, the nano-LAMP may be designed to have a specified signal enhancement in the first dielectric layer and a different level of signal enhancement in the second dielectric layer. In such an embodiment, the nano-LAMP also may be designed to have a region of signal enhancement in the first dielectric layer and a region of signal quenching in the second dielectric layer, or vice versa.

A person of ordinary skill in the art of Raman spectroscopy will understand that the foregoing examples are merely illustrative, and any combination of nano-LAMPs capable of producing signals from both analytes that can be detected in a single assay within the capabilities of the instrumentation utilized may be suitable. A person of ordinary skill in the art in the art of analyte detection will also understand that selective detection of each analyte may be performed by conjugating a specific binding moiety to the nano-LAMP, wherein the specific binding moiety is capable of recognizing and binding to only one of the analytes present in the assay.

Examining quenching as a function of size using GAs, it was determined that quenching can be achieved using three-layered LAMPs by designing the structure to enhance E-fields in the reporter-less, outer protective silica shell. Here, neither the reporter in the inner layers nor the medium outside the probe is enhanced. Embodiments of 3-layered LAMPs were found to be optimal because it becomes progressively more difficult to reorganize plasmonic interactions from several layers into the outer silica layer. In some embodiments, LAMPs may be constructed with only a very low reporter concentration in one of the inner layers to produce a minimally enhanced response.

Figure 5:
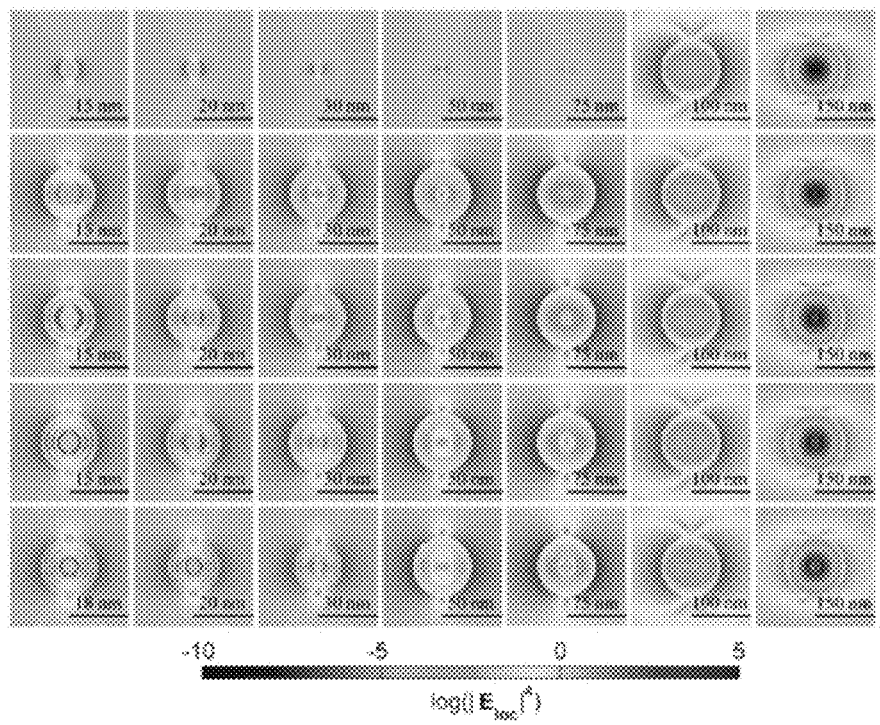
FIG. 5 is a series of images illustrating enhancement distributions in the incident plane of illumination for even-layered silica-silver nano-LAMPs of various configurations that are designed to quench internal enhancements at an excitation wavelength of 785 nm. From top to bottom, the number of layers increases from 2 to 10; from left to right, the total size increases as shown.
Figure 6:
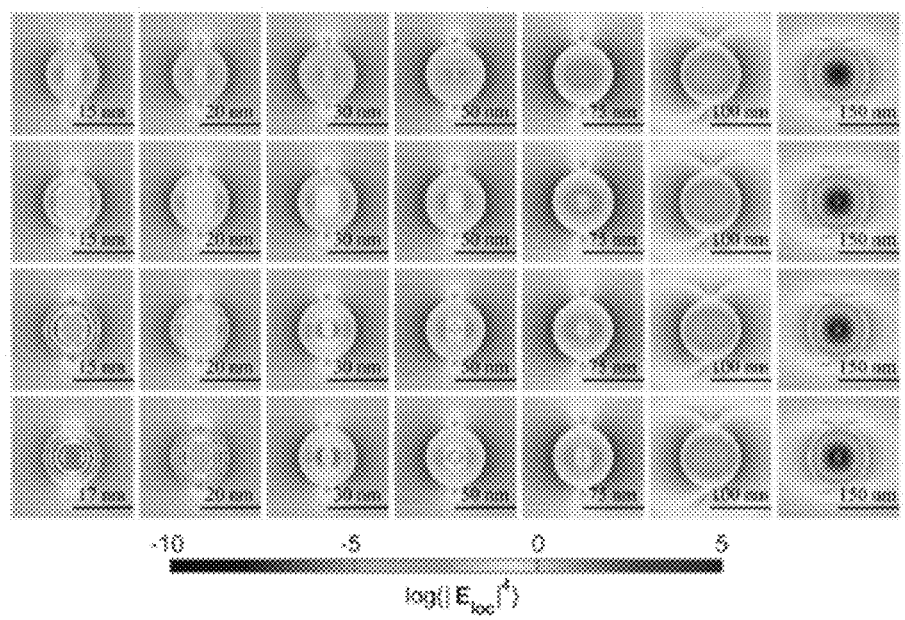
FIG. 6 is a series of images illustrating enhancement distributions in the incident plane of illumination for odd-layered silica-silver nano-LAMPs of various configurations that are designed to quench internal enhancements at an excitation wavelength of 785 nm. From top to bottom, the number of layers increases from 3 to 9; from left to right, the total size increases as shown.
Figure 7:
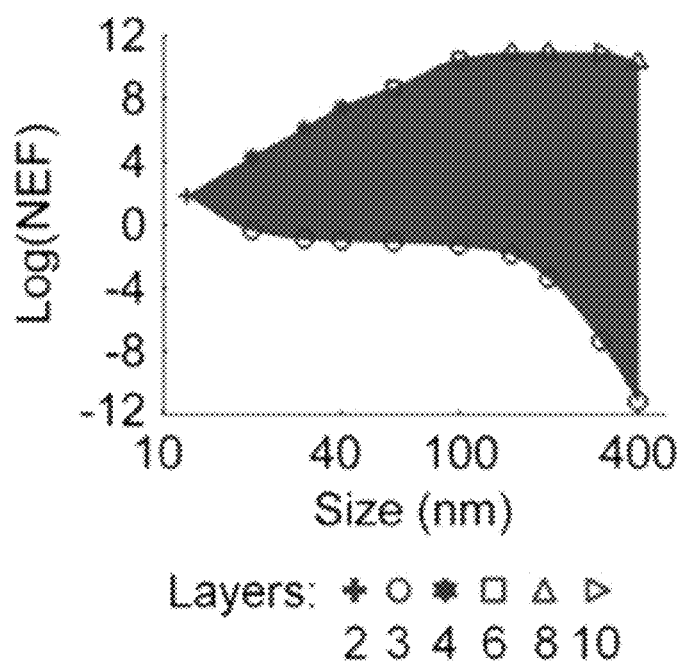
FIG. 7 is a graph illustrating the range of net enhancement factors (NEF) attainable via various silver-silica nano-LAMP configurations at 785-nm excitation as a function of probe size.
Figure 8:
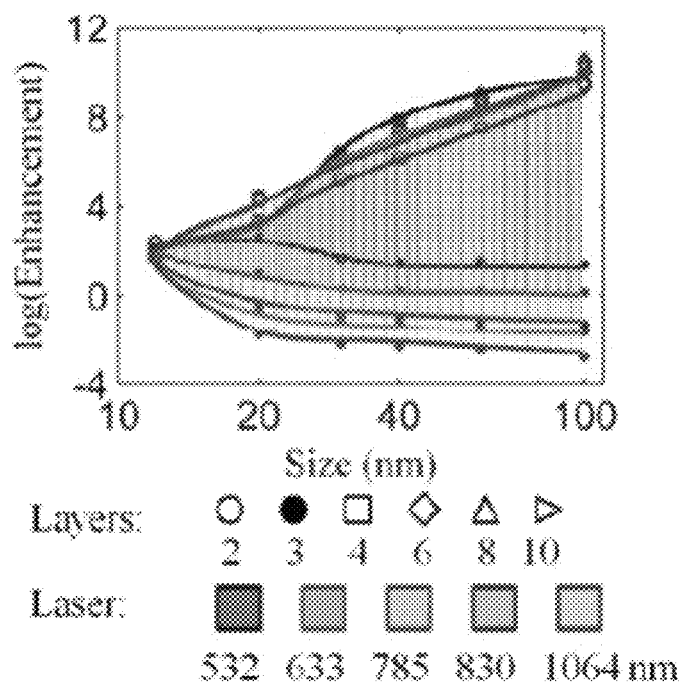
FIG. 8 is a graph illustrating the range of NEF attainable via various silver-silica nano-LAMP configurations as a function of probe size at excitation wavelengths of 532 nm, 633 nm, 785 nm, 830 nm, and 1064 nm.
Figures 9A, 9B, 9C, 9D:
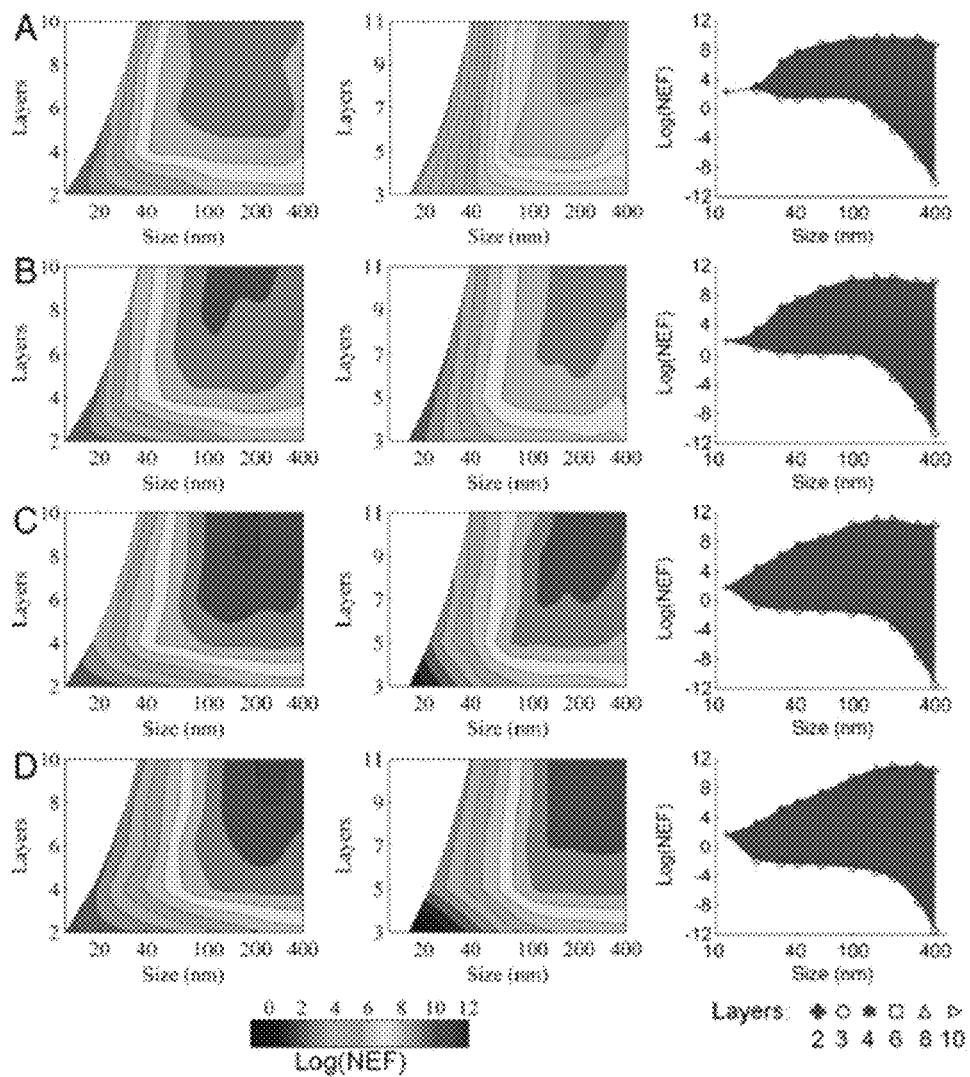
FIGS. 9A-9D illustrate the enhancement and dynamic range of silver-silica nano-LAMPs having different numbers of layers for laser excitations at 532 nm (9A), 633 nm (9B), 830 nm (9C), and 1064 nm (9D). The images in the left column correspond to even-layered LAMPs; the images in the center column correspond to odd-layered LAMPs, and the graphs in the right column illustrate the dynamic range realizable with the nano-LAMPs. The color bar code for the net enhancement factors is shown below the left and middle rows.

Quenching is illustrated in FIGS. 5 and 6, where field distributions in minimized configurations are depicted in the plane of incident illumination. Quenching is enabled by designing the nano-LAMP to distribute the electric field such that total enhancement of signal from the probe is measurable but minimized. An enhanced and quenched probe pair for a given size and excitation wavelength provides the allowable dynamic range as shown in FIGS. 7, 8, 9A-9D, and 10. The shaded regions represent the viable tuning space of probe signals for any common organic compound used as a reporter. A lower concentration or weaker Raman-scattering reporter can be used to further reduce the total signal. Similarly, a resonant dye reporter molecule can be used to further increase the upper limit. For example, by choosing silver-silica LAMPs having non-resonant reporter molecules and a diameter of 100 nm, a maximum NEF of ~$10^{11}$ and quenched NEF of ~$10^{-2}$ at 785 nm excitation (by laser) can be achieved. By using resonant molecules and/or lowering dye concentrations, analytes varying by over 20 orders of magnitude in concentration can be measured in a single assay. Thus, embodiments of the disclosed nano-LAMPs have NEFs ranging from $10^{-6}$ to $10^{16}$, such as $10^{-3}$ to $10^{15}$, $10^{-2}$ to $10^{12}$, or $10^1$ to $10^{11}$.

The response of the nano-LAMP probes may also be tuned to reduce, minimize, or eliminate out-of-probe enhancement (i.e., enhancement of molecules proximal to the probe). Alternatively, the probe can be structured to increase enhancement of analytes in a region proximal to the probe.

An interesting consequence of the interacting plasmons arises in the spectral behavior of LAMPs. Certain embodiments of the disclosed nano-LAMPs demonstrate a spectrally flat response (FIG. 11) compared to simpler structures. The spectral uniformity indicates that the same LAMPs can be excited by multiple laser wavelengths without an enhancement drop-off at shifted frequencies that differ from the excitation laser frequency that coincides with the spectral plasmon resonance peak of SERS probes. Hence, embodiments of the disclosed nano-LAMPs may provide sensitive, tailored, reporter-independent and spectrally consistent responses while being amenable to fabrication.

D. Optical Tunability

Conventional metal nanoparticles possess size-dependent optical and electronic properties. While their scattering, absorption and photoluminescence spectra can directly be detected, it is also possible to achieve enhanced spectra for organic/dye molecules proximal to their surfaces (for example in Raman, infrared, and fluorescence spectroscopy). The photoluminescence of semiconductor crystal emitters can also be enhanced when in the vicinity of nanoparticles. Metal nanoparticles, however, have relatively wide resonance peaks and their size tunability is limited. It is possible to achieve higher optical tunability using asymmetric nanoparticles, but at the expense of polarization effects and variability.

The interplasmon coupling of the metal shells in LAMPs governs their optical properties. Interplasmonic coupling within embodiments of the disclosed nano-LAMPs and hence their spectral responses can be tuned by a rational selection of layer thicknesses. Embodiments of the disclosed nano-LAMPs comprising alternating metal and reporter-filled dielectric layers can be optically tuned to produce application-specific (e.g., excitation wavelength-specific) probes of different sizes. The tunability further increases with the number layers and within a particular probe size, thereby providing structures with distinct resonances at longer wavelengths.

Figure 12:
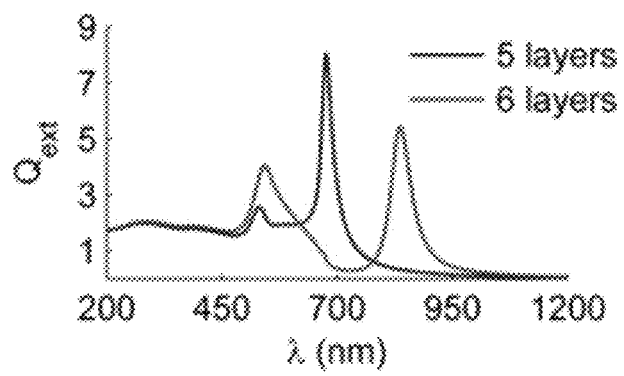
FIG. 12 is a graph illustrating the extinction spectra of 5-layered and 6-layered gold-silica nano-LAMPs (diameter=50 nm).
Figure 13:
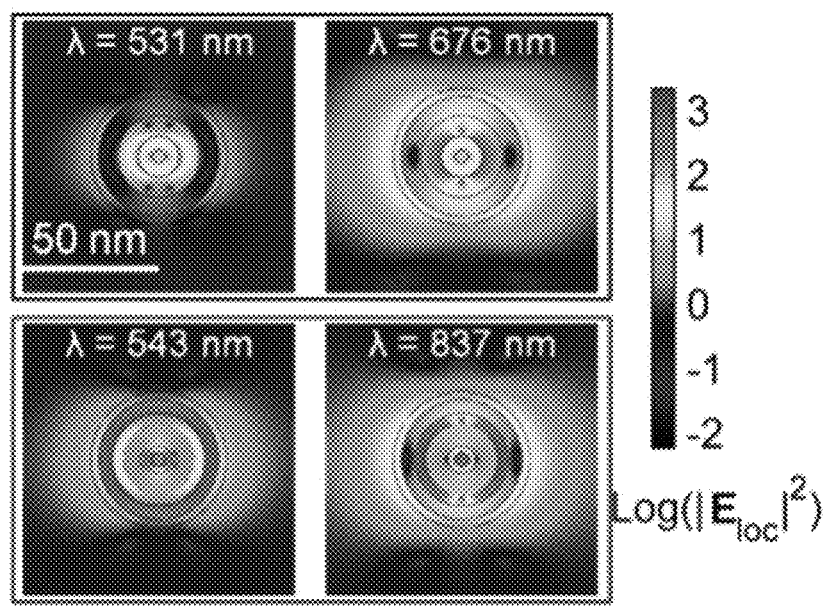
FIG. 13 is a series of images illustrating the internal intensity distribution in the incident plane for the 5-layered (top) and 6-layered (bottom) gold-silica nano-LAMPs of FIG. 12 when illuminated by plane waves at resonant wavelengths.

The mixing of dipolar contributions due to the metal shells typically results in stronger resonances at longer wavelengths while the higher order multipole contributions and their interactions result in weaker resonances at shorter wavelengths. The relative strength of interaction and their manifestation in far-field characteristics is strongly dependent on the overall size of the particle, the relative thicknesses and compositions of each layer. For example, extinction spectra are shown in FIG. 12 for a 5-layered gold-silica LAMP ($r_1=5$, $r_2=15$, $r_3=30$, $r_4=44$ and $r_5=50$ nm) and a 6-layered gold-silica LAMP ($r_1=5$, $r_2=10$, $r_3=26$, $r_4=34$, $r_4=44$ and $r_6=50$ nm). In the spectra shown, there exist two distinct peaks at wavelengths of 531 and 676 nm for 5-layered LAMP and at 543 and 837 nm for the six-layered structure. The peaks at shorter wavelengths are observed to be a combination of resonances, which are due to higher order multipole modes. In addition, the contributions from different metal shells can be understood by examining the local reorganization of electric field within and in the vicinity of LAMPs when illuminated at resonant wavelengths. In FIG. 13, this reorganization can be seen in the intensity distributions in the incident plane. For the 5-layered structure, a relatively stronger resonance at 676 nm illumination results in the fields being enhanced up to 3 orders of magnitude in the outer dielectric layer. At 531 nm, the field is enhanced only up to 1-2 orders of magnitude indicating a weaker resonance. For the 6-layered structure, the contributions due to plasmonic interaction of different metal layers are more apparent. At 543 nm illumination, the coupling between the core and the first metal layer is dominant, resulting in enhanced fields of higher magnitudes in the innermost dielectric layer. At 837 nm illumination, the coupling of the first and second outer metal layers is stronger resulting in enhanced fields of higher magnitudes for the second dielectric layer. The ability to reorganize the enhanced and depleted regions into different dielectric layers can be employed to design probe structures with different enhancement characteristics for reporter molecules localized in different layers.

The resonances in far-field spectra can be directly related to the strength of the local field, $E_{loc}$, within specific dielectric layers, and modeling this relationship facilitates the construction and use of LAMPs. In some embodiments, Mie theory calculations, as described in section IIIA below, are used to predict the fields and far field spectra while employing optimization strategies to precisely tune the structure to the desired response.

By varying layer thicknesses in a LAMP, different higher order multipole modes can be excited resulting in resonances at different wavelengths. The optical tunability can be employed to design nano-LAMPs as probes in a multiplexing application. The tunability can be further extended by preparing probes of different compositions and total sizes. In some embodiments, however, probes of a specific size and composition are prepared. A constant total size confers similar diffusion characteristics and similar availability to the analyte sites, while a single composition facilitates fabrication.

In certain embodiments, nano-LAMPs have a diameter of less than or equal to 100 nm to facilitate biological imaging. The number and thicknesses of the individual layers within the nano-LAMPs are varied to provide resonances at different wavelengths. For example, silver-silica nano-LAMPs with a 100-nm diameter can be designed with spectral peaks in the 200-1200 nm range of excitation as shown in FIGS. 14A-14B and 15A-15B, thereby providing a palette of probes for multiplexing.

Figure 14A:
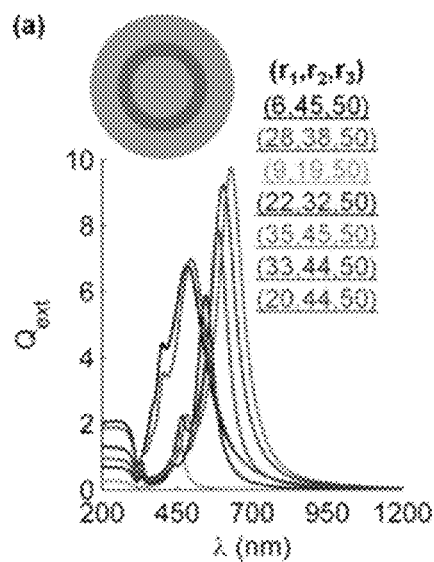
FIGS. 14A-14B illustrate distinct extinction spectra in the 200-1200 nm excitation range for 3-layered silver-silica nano-LAMPs (14A) and 5-layered silver-silica nano-LAMPs (14B) having a 100-nm diameter and varying layer thicknesses.

FIG. 14A shows the radii and extinction efficiency spectra of 3-layered silver-silica LAMPs obtained using a genetic algorithm to select optimal layer thicknesses by maximizing the cost function; in this case, the cost function was a contrast ratio, i.e., the ratio of cumulative extinction in the desired illumination wavelength region/cumulative extinction in the rest of the range. To facilitate fabrication of continuous, uniform layers, the metal layers and dielectric layers were constrained to be at least 10 nm and 5 nm in thickness, respectively. Changing layer thickness results in a change of the probes' spectral features due to a change in plasmonic coupling. Several characteristics are apparent. In structures with thinner metal layers, with the radii denoted in short as a set of numbers—({35, 45, 50}, {33, 44, 50}, {28, 38, 50}, {22, 32, 50}, and {9, 19, 50}), stronger interaction of plasmons results in stronger and narrower resonances. The resulting thicker outer silica layer, however, lowers the strength of this resonance. In contrast, the structures with thicker metal layers ({6, 45, 50}, {20, 44, 50}) possess broader peaks. While the thicker layer can effectively isolate the plasmons of two surfaces, the size available for separation is not large enough to result in two well separated peaks.

Figure 14B:
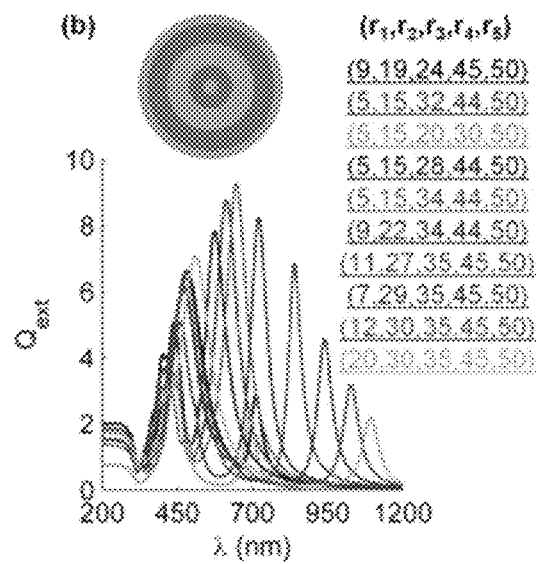

FIG. 14B depicts the radii and distinct extinction spectra of 5-layered silver-silica LAMPs. The presence of two metal layers and the interaction of multipole contributions due to these layers can be utilized to achieve multiple resonances. It can also be observed that the resonances at longer wavelengths can be shifted further into near-infrared for the 5-layered LAMPs. Moreover, the resonances for the 5-layered LAMPs are better separated in comparison to those for 3-layered LAMPs due to increased spectral range. A notable characteristic of the optimization determined by the genetic algorithm was that it predicted structures with the thinnest possible metal layers. The presence of a thin outer metal layer ensures the existence of a resonance at longer wavelengths. Using the thinnest outer metal layer (e.g., 10 nm) further maximizes this resonance. However, if desired, a different cost function could be chosen to select for the width of the peak and/or achieving a higher number of peaks. More complicated cost functions and constraints can also be visualized; for example, a cost function to control peak width can be optimized subject to the constraint of a specific contrast ratio.

Figure 15A:
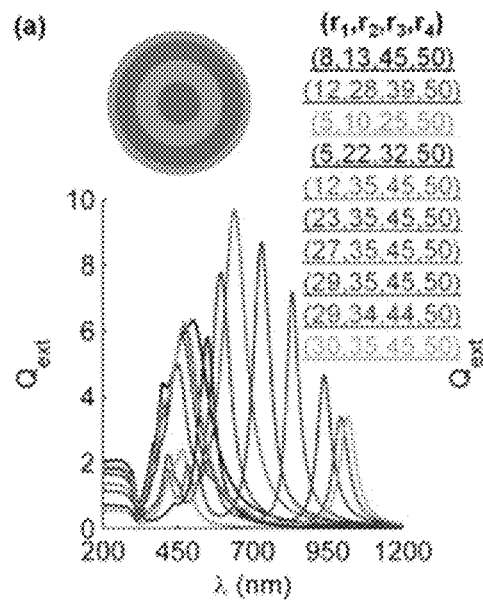
FIGS. 15A-15B illustrate distinct extinction spectra in the 200-1200 nm excitation range for 4-layered silver-silica nano-LAMPs (15A) and 6-layered silver-silica nano-LAMPs (15B) having a 100-nm diameter and varying layer thicknesses.
Figure 15B:
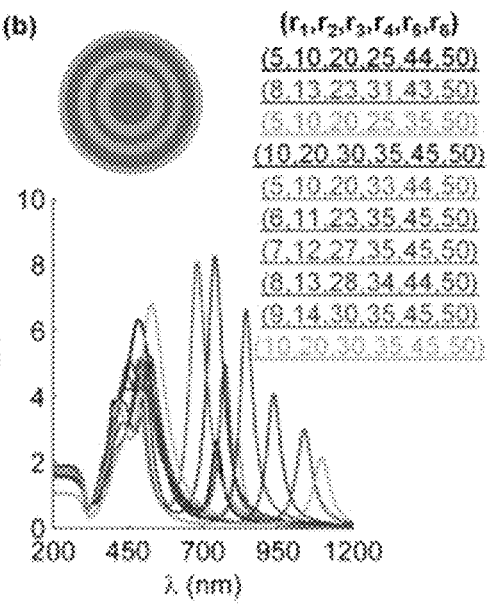
Figure 16:
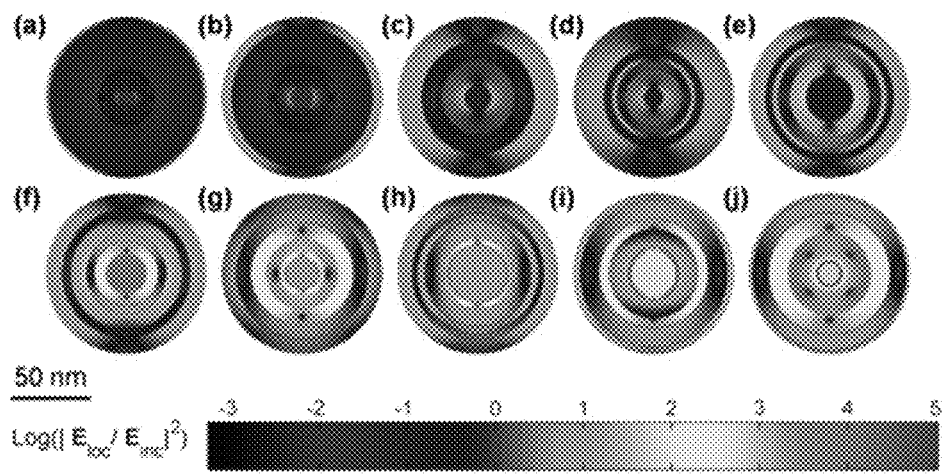
FIGS. 16A-16J are a series of images illustrating enhancement in the internal fields in dielectric layers of 100-nm diameter, six-layered gold-silica nano-LAMPs of varying layer thicknesses when illuminated by a plane wave of wavelength 785 nm. The distributions are shown in the incident plane with incident field polarized horizontally. The structures shown have radii 5, 14, 16, 17, 48, 50 nm (16A); 7, 17, 20, 21, 44, 50 nm (16B); 8, 23, 25, 26, 35, 50 nm (16C); 6, 18, 23, 26, 31, 50 nm (16D); 15, 25, 32, 36, 40, 50 nm (16E); 13, 20, 25, 35, 40, 50 nm (16F); 10, 14, 22, 32, 41, 50 nm (16G); 18, 22, 33, 38, 41, 50 nm (16H); 14, 16, 28, 34, 46, 50 nm (16I); 7, 8, 26, 38, 48, 50 nm (16J). The boundaries of different layers are depicted using black lines.

The extinction spectra of 4-layered and 6-layered silver-silica LAMPs (FIGS. 15A-15B) indicate that similar results occur with even-layered structures. For the 4-layered silver-silica LAMPs with near-infrared resonances, the thickness obtained for the silica layer between the two metal layers is minimal, which is consistent with the scaling law for plasmon resonance shift proposed in case of gold-silica-gold spheres. The presence of the extra (protective) silica layer further red-shifts the resonances. As in the case of 3-layered and 5-layered LAMPs, the outermost metal layer is the thinnest possible for achieving resonances in the near-infrared wavelengths, but the core is larger. As the core size becomes smaller and the outer metal layer becomes thicker, the resonances at shorter wavelengths become stronger and broader. The presence of additional metal and silica layers in the designed six-layered LAMPs result in distinguishable peaks at the shorter wavelengths as shown in FIG. 15B. As in the case of odd layered LAMPs, the additional layers increase the optical tunability and structures with resonances further into near-infrared can be made.

For both odd-layered and even-layered LAMPs, the multiple peaks achieved are easily distinguishable. With a multivariate curve resolution algorithm, for example, embodiments of the disclosed nano-LAMPs could be easily employed for multiplexed analyses. Several other interesting aspects of the design are apparent. The plasmonic interaction between metal layers in smaller particles (sizes below 100 nm) may be relatively weaker and all the plasmon modes might not be resonant. For a given total size, LAMPs with a larger number of layers can produce resonances at longer wavelengths. The extinction characteristics of LAMPs are due to contributions from both scattering and absorption; scattering is dominant for the LAMPs considered here. In certain embodiments, the ratio of scattering to absorption may be varied and multiplexing probes may be prepared for various spectroscopic modalities.

E. Scalable Responses

Embodiments of the disclosed nano-LAMPs can be designed such that their signal arises not directly from the overall scattering and absorption of the probe but from the emission or inelastic scattering characteristics of reporter molecules in the dielectric layers. In some embodiments, reporter signals are tuned at a particular wavelength through the electric fields induced in the dielectric layers. In certain embodiments, the interaction between the reporter molecules and the metal is reduced through the separation offered by the dielectric material. This ensures the reliability of enhancement in the signal by basing it purely on the composition and structure of the probe and not on the specifics of metal-reporter interactions. Embodiments of the disclosed nano-LAMPs with embedded reporters provide advantages over conventional SERS probes. For example, stronger enhancements can be achieved with multilayer particles that are difficult to achieve with simpler geometries. Second, nano-LAMPs can be designed to possess a specified amplification of response and/or can be designed for enhancement at specific wavelengths.

FIGS. 16A-16J are a series of images illustrating amplifications in the internal field distributions for 6-layered gold-silica nano-LAMPs (diameter=100 nm) at 785 nm excitation. As shown in FIGS. 16A-16J, by varying the layer thicknesses, the nano-LAMPs can be designed such that the maximal field achieved within the particle can be tuned to be 1-5 orders of magnitude larger than the incident field. A very thick outermost metal shell is observed to dampen fields inside the nano-LAMP compared to fields outside the nano-LAMP, e.g., FIGS. 16A and 16B. In contrast, when the inner metal and silica layers and the outer most silica layers are chosen to be thicker, the enhancement within the nano-LAMP is higher, e.g., FIGS. 16F-16J. For structures with greater enhancements, the metal layers are typically separated by thin dielectric layers and one of the inner metal layers (core or the first outer metal layer) is large, e.g., FIGS. 16H-16J. The stronger enhancement regions achieved within nano-LAMPs extend over a large part of the dielectric layer; hence, a uniform reporter distribution is likely beneficial. The strongest enhancements are much higher than what could be achieved with the single nanoparticles and the extent of enhanced regions is much larger compared to simple nanoparticle aggregates.[3] For example, the strongest enhancements from nanoshells are approximately $10^6$ while nano-LAMP enhancements can be much larger. Similarly, gaps between nanoparticle aggregates may be approx. 1-100 $nm^3$ but the dielectric volume in nano-LAMPS can be much larger.

Figure 17:
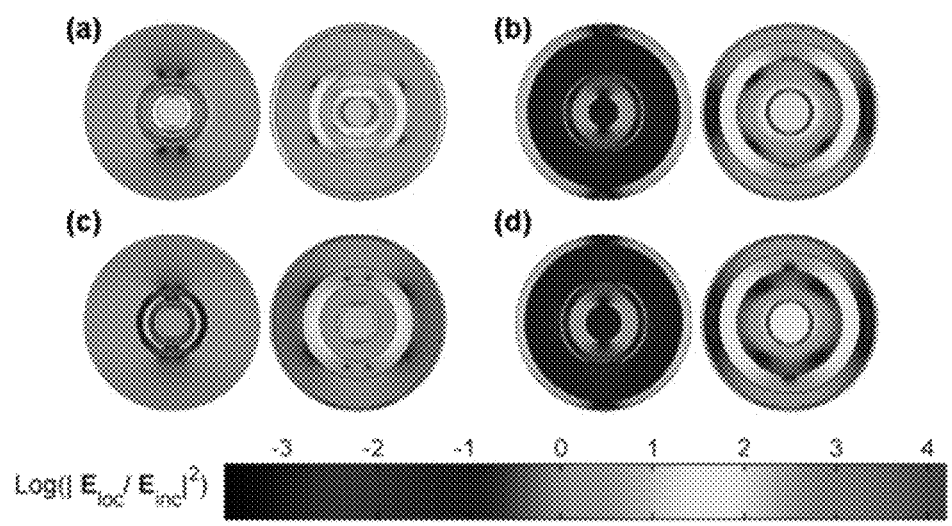
FIGS. 17A-17D are a series of images illustrating the internal field distributions in 60-nm diameter six-layered gold-silica nano-LAMPs (17A, 17B) and copper-silica nano-LAMPs (17C, 17D) designed for minimal and maximal enhancements at excitation wavelengths 532 nm (17A, 17C) and 785 nm (17B, 17D). The distributions are shown in the incident plane with incident field polarized horizontally. The structures shown have layers with radii selected to produce minimal or maximal enhancement: (17A) minimal-left: {5, 7, 9, 10, 12, 30 nm}, maximal-right: {5, 9, 13, 17, 28, 30 nm}; (17B) minimal-left: {5, 11, 13, 14, 26, 30 nm}, maximal-right: {7, 8, 18, 24, 29, 30 nm}; (17C) minimal-left: {5, 6, 8, 10, 12, 30 nm}, maximal-right: {6, 7, 13, 19, 29, 30 nm}; (17D) minimal-left: {6, 12, 14, 15, 27, 30 nm}, maximal-right: {7, 8, 18, 24, 29, 30 nm}. The boundaries of different layers are depicted using black circles.

FIGS. 17A-D are a series of images illustrating the internal field distributions in 60-nm diameter, 6-layered gold-silica nano-LAMPs (17A, 17B) and copper-silica nano-LAMPs (17C, 17D). In FIGS. 17A and 17C, the excitation wavelength is 532 nm; in FIGS. 17B and 17D, the excitation wavelength is 785 nm. In each pair of images, the left image is a nano-LAMP designed to have minimal enhancement in the innermost dielectric layer, and the right image is a nano-LAMP designed to have maximal enhancement in the innermost dielectric layer. The structures with minimal enhancements can provide quenching of the response, and together with structures of maximal enhancements can be used to probe analytes of widely varying abundances in a multiplexed fashion. At 785 nm excitation, the structures designed for maximal enhancement utilizing copper-silica and gold-silica are the same. The structures for minimal enhancements derived are also similar. Moreover, the achieved maximal and minimal enhancements are of similar magnitude at longer wavelengths of excitation. Thus, either copper or gold can be employed to design probes with equal effectiveness. At 532 nm excitation, however, the maximal and minimal enhancements are higher for gold-silica LAMPs because plasmon modes for gold layer sizes shown in FIG. 17*a* (i.e., 5, 9, 12 nm) are resonant at wavelengths closer to 532 nm compared to plasmon modes for the copper layers shown in FIG. 17*c* (i.e., 5, 8, 12 nm). In all cases shown, the structures for minimal enhancements possess a thicker outermost metal or silica layer and the structures for maximal enhancements possess thinner dielectric layers, which is consistent with observations made in FIGS. 16A-16J.

Figure 18:
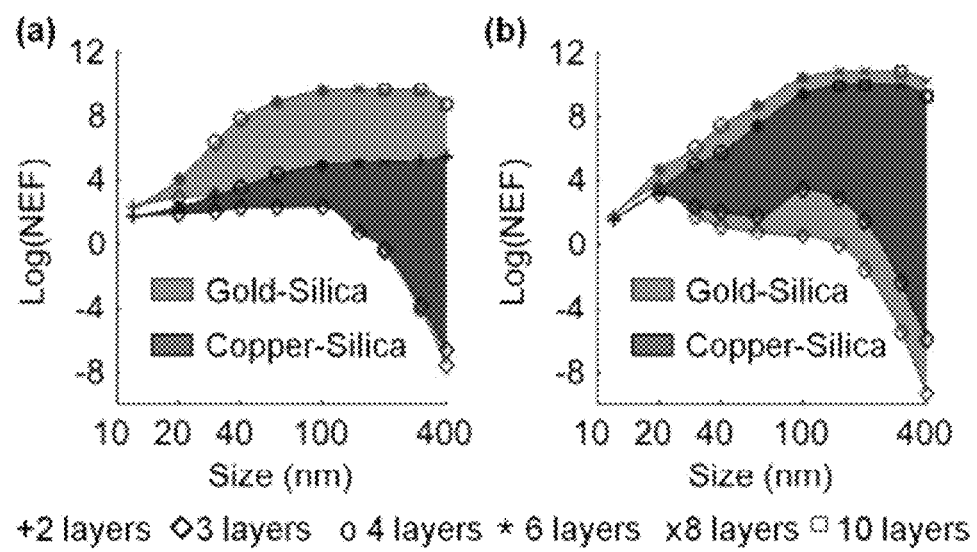
FIGS. 18A-18B are graphs illustrating the dynamic range of achievable Raman net enhancement factors using gold-silica and copper-silica nano-LAMPs of different sizes and different numbers of layers at an excitation wavelength of 532 nm (18A) and 785 nm (18B). The data points are connected by smooth, piecewise cubic interpolation.

The utility of nano-LAMPs for multiplexed probing of analytes with different concentrations is dependent at least in part on the range within which the magnitudes of their responses can be scaled. The NEF (equation (1)) is useful for evaluating nano-LAMPs as Raman probes. In the calculations, $|E_{loc}(\lambda)|^4$ is utilized as an approximation for $|E_{loc}(\lambda+\delta\lambda)|^2|E_{loc}(\lambda)|^2$. Without loss of generality, reporters are assumed to have a molecular volume of 0.5 $nm^3$ and to be uniformly embedded in dielectric layers at a very low concentration (1% in volume). The dynamic range provided by LAMPs for use in multiplexed assays is then equivalent to the range over which the NEF can be tuned. FIGS. 18A-18B are graphs illustrating the dynamic range of achievable net enhancement factors using gold-silica and copper-silica nano-LAMPs of different sizes and with different numbers of layers at an excitation wavelength of 532 nm (18A) or 785 nm (18B). The NEFs in LAMPs are a cumulative contribution of the dielectric volume (and reporter loading) and coupled electromagnetic enhancement (i.e., measure of the reorganized fields). As the total size increases, the numerical contribution to the NEF increases while the electromagnetic enhancement decreases. The size at which the combined effect of both contributions is maximized typically occurs around 100 nm. At smaller sizes, the maximal NEFs are achievable with nano-LAMPs having a smaller number of layers, while a larger number of layers is beneficial for nano-LAMPs with larger sizes. The 3-layered nano-LAMPs further offer a unique capability to reorganize the fields into the protective silica layer or outside the nano-LAMP. Hence, 3-layered nano-LAMPs are very effective in quenching the fields inside the silica core. At larger particle sizes, this could lead to nano- LAMPs with greatly quenched Raman responses as shown in the data points with minimal NEFs in FIGS. 18A-18B. As size increases, the dynamic ranges achieved through maximal and minimal NEFs increases. In some embodiments, the fields are further reorganized into different dielectric layers and/or the multiplexing capabilities of the probes are further enhanced by choosing reporters of different (resonant and non-resonant) scattering properties.

III. METHODS OF DESIGNING AND MAKING NANO-LAMPS

In spherical nano-LAMPs, alternating metal and dielectric shells are designed such that inter-plasmonic coupling of metal shells produces modified electric fields in the dielectric shells and/or outside the particle when illuminated. As described infra, the internal fields within multilayered spheres, such as nano-LAMPs, can be calculated using layered Mie theory, and the structure can further be refined using a genetic algorithm.

The incident excitation wavelength is assumed to be much larger than the LAMPs, hence, only responses to plane wave excitations are evaluated. The electromagnetic field in each layer of the sphere is represented in terms of standard vector spherical harmonics (VSH). Utilizing the field continuity between different layers along with the outermost layer and incident field, a set of equations in terms of coefficients of expansion for each layer is obtained.[4,5] By using an appropriate cutoff[6] for the maximum order of VSH and stable recursive formulations of logarithmic derivative and ratio functions involved, expansion coefficients and internal fields within each layer are calculated. The far-field characteristics are dependent on the coefficients of the scattered field outside LAMP and are evaluated using asymptotic expansions. Both far-field and internal field characteristics are dependent on thicknesses as well as refractive indices of individual layers. For metal layers of thickness greater than 10 nm, it is typically acceptable to use the bulk values.[7] In nano-LAMPs including metal shells thinner than 10 nm, a correction[8] is implemented to the imaginary part of refractive index to account for the reduced mean free path available for the electrons and the resulting effects.

For applications in which the response of organic (dye) molecules in silica shells is detected, chemical enhancement (for example, due to charge transfer in case of Raman scattering) is ignored. Although this approximation might underestimate enhancements, it provides a minimum value for the reliable enhancement in Raman/IR/photoluminescence signals. A further assumption is made that the reporter molecules are dispersed uniformly in the dielectric layer, rather than being attached as a self-assembled monolayer (SAM) to metal surfaces. SAMs form a subset of the results since the present method seeks to optimize fields as an average over the entire dielectric layer. The distribution of reporter in the entire dielectric volume instead of being at the surface of the metal also makes the CE lower as the number of surface active sites is small (Fang et al., *Science*, (2008) 321:388-392). While enhancement in infrared absorption, fluorescence and photoluminescence scales with local field intensity ($|E_{loc}(\lambda_{inc})|^2$), Raman enhancement scales with square of local field enhancement ($|E_{loc}(\lambda_{inc})|^2$) multiplied with the square of shifted Raman field ($|E_{loc}(\lambda_{inc}+\delta\lambda)|^2$).[9] Here, $E_{loc}$ is the field at incident wavelength $\lambda$ shifted by a wavelength $\delta\lambda$. Typically, the scattered fields at incident and Raman shifted frequencies are of similar magnitudes; hence, the local enhancement near a reporter can be approximated as $|E_{loc}(\lambda_{inc})|^4$.[10]

Figure 19:
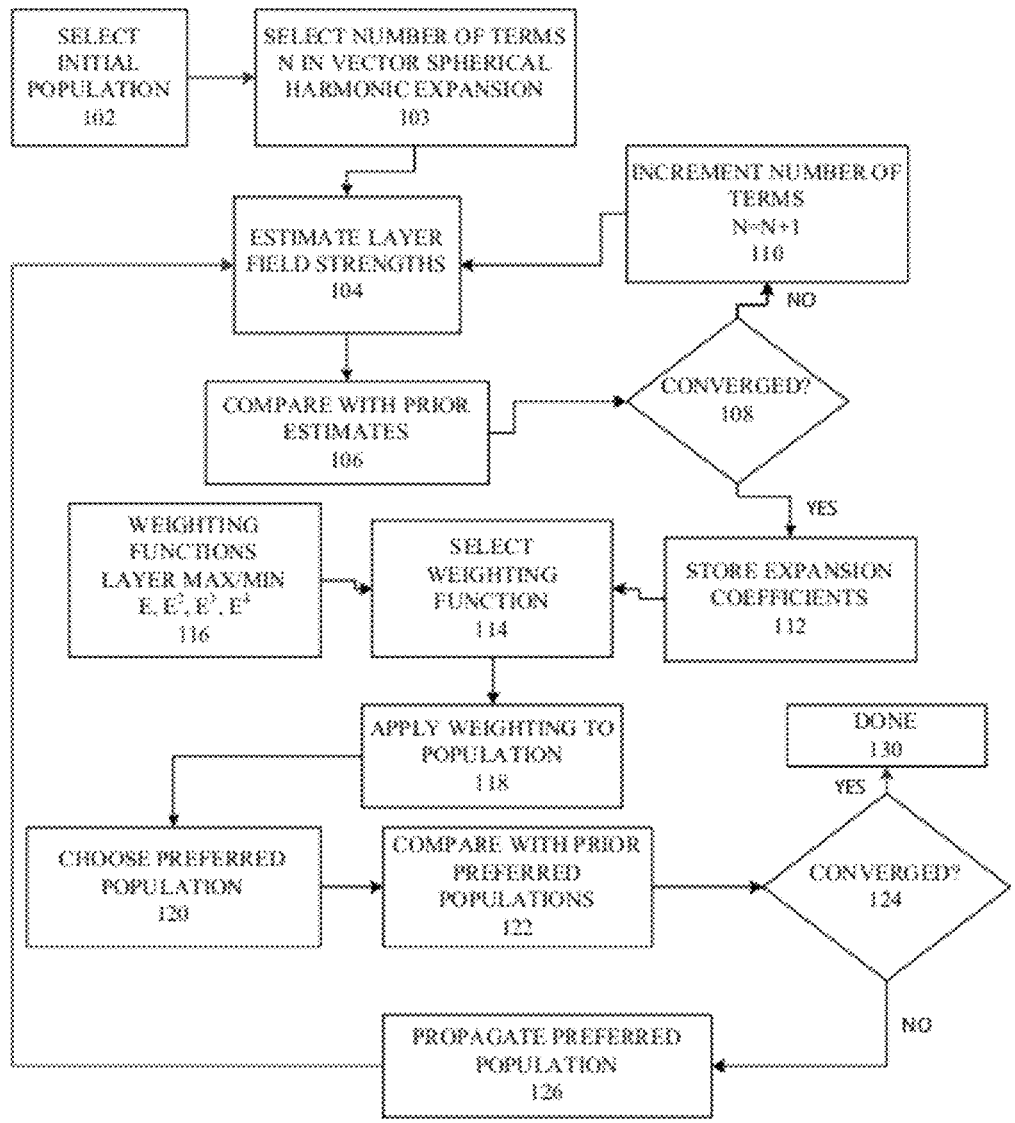
FIG. 19 is a flowchart illustrating a representative method of selecting a nano-LAMP structure.

An overview of a representative method of selecting nanoshell structures is illustrated in FIG. 19. At 102, an initial population of nanoshells is selected. For example, a total thickness range, layer thickness ranges for metallic and dielectric layers, reporter concentration ranges, and/or numbers of layers including preference for odd or even numbers of layers can be selected. At 103, a number of terms N in a vector spherical harmonic field representation is selected, and at 104, fields are estimated using such a representation. Calculated field estimates are compared with prior estimates at 106, and if changes from prior estimates are not sufficiently small, the value of N is increased at 110 and fields are estimated again. If the field estimates are satisfactory, the expansion coefficients are stored at 112. At 114 a weighting function is selected from a database 116. Typically weighting functions are based on a power of an electric field strength, with an objective of maximizing or minimizing a volume or other average of a particular power in selected layers. At 118 the weighting is applied, and at 120, a preferred population of nanoshell structures is selected based on the weightings. The preferred population is compared with prior estimates at 122, and if further refinements in structures are to be requested at 124, the preferred population is propagated at 126 using a genetic algorithm as described infra, and the calculation of field strengths is repeated at 104. If the resulting structures are deemed satisfactory at 124, structure determination halts at 130.

In one embodiment, the method of FIG. 19 is performed by a computer. A computer-readable medium is provided, wherein the computer-readable medium includes instructions that, when executed by a computer, cause the computer to (a) receive and store in a database input from a user, the input comprising parameters for a multilayered nanoparticle, the parameters comprising an overall diameter, a core diameter, a number of layers, a metal, a dielectric, thickness ranges for metal layers, thickness ranges for dielectric layers, and, optionally, a reporter molecule and a reporter molecule concentration, (b) estimate, based upon the parameters, field strengths for each layer, (c) compare estimated field strengths with prior estimated field strengths to provide a comparison, (d) store in the database expansion coefficients, (e) select a weighting function from a database, wherein the weighting function is based on a power of an electric field strength, (f) apply the weighting function, (g) select at least one nanoshell structure, and (h) generate an output comprising a multilayered nanoparticle design based upon steps (a)-(g).

A. Layered Mie Theory

Since the Raman enhancements observed so far are greatest for silver, it is chosen as the metal and silica is chosen as both the dielectric and protective layer in the following calculations. The core of the nano-LAMPs is constrained to be larger than 10 nm in diameter and shells to be thicker than 2 nm and 1 nm for the metal and dielectric material, respectively. A 1% loading and a molecular volume of 0.5 nm³ for the reporter are considered. Numerical integration of electromagnetic enhancement is performed with a weighted sum of integrand values using weights derived appropriate for spherical shells.[11] The probe structure is optimized for maximal/minimal NEF using genetic algorithms.[12] Whole number shell sizes subject to size constraints are encoded using floating point numbers in [0, 1] interval. Simulations are run until the error function does not decrease further with additional time steps and the convergence is apparent.

Figure 20:
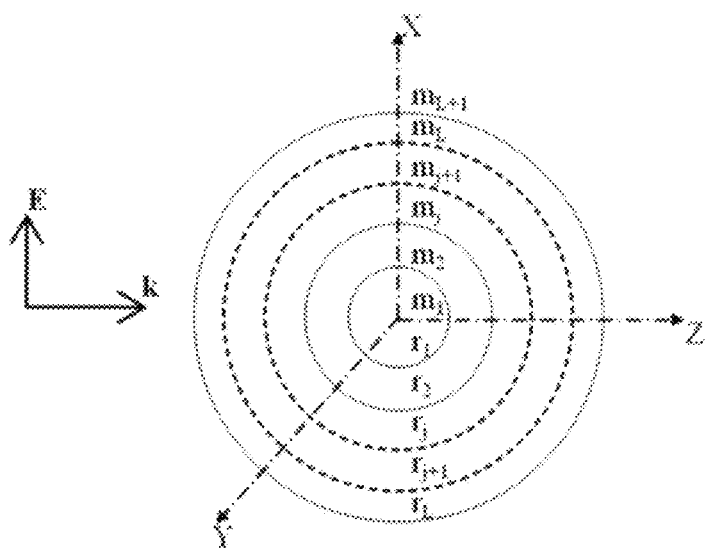
FIG. 20 is a diagram illustrating a multilayered nanosphere configuration used for computation.

Due to the symmetry of LAMPs (FIG. 20), the response due to a laser excitation can be simulated by evaluating the fields within the sphere when a plane wave is incident, without the loss of generality, by extending Mie theory. We consider here an L-layered nanosphere with embedding medium denoted by L+1, the field in $j^{th}$ layer can be represented in terms of vector spherical harmonics as:

$$E_j = \sum_{n=1}^{N} E_n \begin{bmatrix} \frac{-in(n+1)}{(\kappa_j r)^2} \pi_n(\cos\theta)\sin\theta\cos\phi U_n^j(\kappa_j r)e_r + \\ \frac{\cos\phi}{(\kappa_j r)}\{\pi_n(\cos\theta)V_n^j(\kappa_j r) - i\tau_n(\cos\theta)(U_n^j(\kappa_j r))'\}e_\theta - \\ \frac{\sin\phi}{(\kappa_j r)}\{\tau_n(\cos\theta)V_n^j(\kappa_j r) - i\pi_n(\cos\theta)(U_n^j(\kappa_j r))'\}e_\phi \end{bmatrix} \quad (2)$$

$$H_j = -\frac{\kappa_j}{\omega}\sum_{n=1}^{N} E_n \begin{bmatrix} \frac{in(n+1)}{(\kappa_j r)^2}\pi_n(\cos\theta)\sin\theta\sin\phi V_n^j(\kappa_j r)e_r - \\ \frac{\sin\phi}{(\kappa_j r)}\{\pi_n(\cos\theta)U_n^j(\kappa_j r) - i\tau_n(\cos\theta)(V_n^j(\kappa_j r))'\}e_\theta - \\ \frac{\cos\phi}{(\kappa_j r)}\{\tau_n(\cos\theta)U_n^j(\kappa_j r) - i\pi_n(\cos\theta)(V_n^j(\kappa_j r))'\}e_\phi \end{bmatrix} \quad (3)$$

where the functions $U_n$ and $V_n$ are given in terms of Ricatti-Bessel functions $\psi$ and $\xi$ as follows:

$$U_n(\kappa_j r) = d_n^j \{\psi_n(\kappa_j r) - A_n^j \xi_n(\kappa_j r)\}, \quad (4)$$

$$V_n(\kappa_j r) = c_n^j \{\psi_n(\kappa_j r) - B_n^j \xi_n(\kappa_j r)\}, \quad (5)$$

For the field in the core and the incident field, to be well defined at origin: $a_n^1 = b_n^1 = 0$ and for the field in the embedding medium to be well defined at infinity: $c_n^{L+1} = d_n^{L+1} = 1$. The other coefficients of expansion can be obtained using the following continuity conditions between j and $(j+1)^{th}$ layer, for j=1, ... L.

$$(E_{j+1} - E_j) \times e_r = 0, \quad (6)$$

$$(H_{j+1} - H_j) \times e_r = 0 \quad (7)$$

Applying these boundary conditions and using orthogonality of the functions involved, a recursive formulation can be obtained. In the following, logarithmic Bessel functions $D_n^{(1)}(=\psi_n'/\psi_n)$, $D_n^{(3)}(=\xi_n'/\xi_n)$ and ratio function $R_n(=\psi_n/\xi_n)$ are used for stability and accuracy of calculating higher order coefficients.

The coefficients $A_n$ and $B_n$ are obtained by upward recursion and the coefficients as follows.

$$A_n^1 = 0,\ B_n^1 = 0 \text{ and for } j = 2, ... L \quad (8)$$

$$G_n^j = \frac{1}{m_j}\left\{\frac{R_n(\kappa_j r_j)D_n^{(1)}(\kappa_j r_j) - A_n^j D_n^{(3)}(\kappa_j r_j)}{R_n(\kappa_j r_j) - A_n^j}\right\}, \quad (9)$$

$$H_n^j = m_j\left\{\frac{R_n(\kappa_j r_j)D_n^{(1)}(\kappa_j r_j) - B_n^j D_n^{(3)}(\kappa_j r_j)}{R_n(\kappa_j r_j) - B_n^j}\right\}, \quad (10)$$

$$A_n^{j+1} = -R_n(\kappa_{j+1} r_j)\frac{m_{j+1}G_n^j - D_n^{(1)}(\kappa_{j+1} r_j)}{m_{j+1}G_n^j - D_n^{(3)}(\kappa_{j+1} r_j)}, \quad (11)$$

$$B_n^{j+1} = -R_n(\kappa_{j+1} r_j)\frac{H_n^j - m_{j+1}D_n^{(1)}(\kappa_{j+1} r_j)}{H_n^j - m_{j+1}D_n^{(3)}(\kappa_{j+1} r_j)}, \quad (12)$$

The coefficients $c_n$ and $d_n$ are obtained by proceeding in a downward recursion as follows:

$$c_n^{L+1} = 1,\ d_n^{L+1} = 1 \text{ and for } j = L, ... 1 \quad (13)$$

$$U_n^j = d_n^{j+1}\xi_n(\kappa_{j+1} r_j)\{R_n(\kappa_{j+1} r_j) + A_n^{j+1}\}, \quad (14)$$

$$V_n^j = c_n^{j+1}\frac{m_j}{m_{j+1}}\xi_n(\kappa_{j+1} r_j)\{R_n(\kappa_{j+1} r_j) + B_n^{j+1}\}, \quad (15)$$

$$d_n^j = \frac{U_n^j(\kappa_j r_j)}{\xi_n(\kappa_j r_j)\{R_n(\kappa_j r_j) + A_n^j\}}, \quad (16)$$

$$c_n^j = \frac{V_n^j(\kappa_j r_j)}{\xi_n(\kappa_j r_j)\{R_n(\kappa_j r_j) + B_n^j\}} \quad (17)$$

Using the above formulation, the coefficients of expansion can be evaluated, and hence the internal as well as external E-fields and intensities of the nanosphere at a given excitation frequency. The evaluation of Ricatti-Bessel functions and the number of terms chosen is done using standard approaches.[13,14] The refractive index values for silver are chosen from standard bulk values[7] whenever the size of the shell is greater than 10 nm. For small sizes, a size-based correction method[8] is adopted that accounts for reduced mean free path of electrons in case of isotropic scattering.

B. Genetic Algorithm and Parameters

With respect to nano-LAMPs comprising alternating silver-silica layers, the adapted operators for the algorithm are: tournament selection without replacement (s=4)[15], simulated binary crossover (SBX)[16,17] with $\eta c=10$, crossover probability pc=0.9, a polynomial mutation[18] with $\eta=20$, and mutation probability p=0.1. In some embodiments, the GA was run for about 30-50 iterations after which all cases converged. In tournament selection without replacement and with tournament size s, s chromosomes (probe structures) are chosen at random without replacement and entered into a tournament against each other. The best (low error) individual in the group of s wins the tournament and is selected into a mating pool for evolving new solutions. In SBX, individuals in the mating pool are divided into random pairs and each pair undergoes recombination with a probability pc. For each pair participating in the crossover, each gene (or shell size) undergoes a contracting or expanding crossover operation with a probability 0.5. Therefore, for each pair of chromosomes undergoing recombination, on average half of the genes are modified using either contracting or expanding crossover operations. The operations are designed to mimic crossover operator behavior on binary domains. The polynomial mutation is similar to SBX, and the only difference is in the computation of the polynomial probability. Instead of using genotypic distance between two parents as in SBX, the distance between a gene and its corresponding upper or lower bound, whichever is closer, is considered in computing the contracting and expanding probability distributions. In polynomial mutation, each gene (or variable) undergoes contracting or expanding operation with a probability p.

With respect to gold-silica and copper-silica nano-LAMPs, whenever required an optimization of peak wavelength and height for far-field spectra and internal fields for Raman/fluorescence and photoluminescence spectra of reporter molecules is employed. A set of 1000 probe structures is chosen at random and tournaments are conducted on sets of 4 probe structures to evaluate the best configuration (with maximal/minimal internal field in dielectric layers or minimal difference with requisite ratio of far-field spectral peak wavelength to peak width). These "fit" structures are entered into a mating pool and undergo a simulated binary cross over recombination with a probability of 0.9 and polynomial mutation recombination with a probability of 0.1. For each pair of structures undergoing recombination in cross over, on average half of the shell sizes are modified using either contracting or expanding crossover operations. The pairs of structures undergoing recombination in polynomial mutation the shell sizes expand or contract based on the closeness to upper or lower bounds. The population is then updated by replacing the "least fit" individuals with the recombined structures. The updates are performed iteratively until the convergence of fitness of the best individual structure in the population is apparent. In some embodiments, about 30 to 50 iterations were required for convergence.

C. Designing the Analytical Volume in and Around the Nano-LAMP

The strength and extent of regions with amplified fields (hot-spots) in and around a nano-LAMP typically co-exist with other regions with depleted fields (quenched-spots). The spectral response of organic molecules in the vicinity of or within a nano-LAMP is determined at least in part by the local field strength. Accordingly, the specificity of an analytical volume in and/or around a nano-LAMP can be optimized by designing its structure. In some embodiments, Mie theory is used to evaluate electric fields induced by specific structures, followed by a genetic algorithm-based optimization to design nano-LAMPs that selectively enhance the response of molecules located either outside the nano-LAMP (e.g., an analyte) or in various dielectric layers (i.e., reporter molecules). The sensitivity enhancement is accompanied by an understanding of the quenching in other regions such as to localize the analytical signal from a desired region. Some embodiments of the disclosed nano-LAMPs have greatly enhanced sensitivity and enhanced control of background signal compared to other simpler geometries.

Illumination of a nanoparticle by light induces waves of surface-confined collective electron oscillations. The consequent redistribution of the space around the particle into enhanced electromagnetic (EM)-field regions (hot-spots) and depleted EM-field regions (quenched-spots) can be exploited to sense the presence of molecular species around the particle. An exponential decay in electric field that depends on the composition and/or size of the particle[22] provides a characteristic sensing volume around the particle. The strength, spatial extent and/or the wavelength-dependence of this electric field may be modified by proximity and/or orientation of other metallic particles or surfaces.

In some embodiments, a nano-LAMP is designed to enhance the signal arising from molecular species (i.e., reporter molecules) within the particle. In other embodiments, a nano-LAMP is designed to probe the environment, e.g., to enhance the signal arising from an analyte, outside the particle. In such embodiments, the nano-LAMP is designed so that the signal enhancement occurs in the environment surrounding the nano-LAMP.

Embodiments of the disclosed nano-LAMPs may be used with spectroscopic techniques based on luminescence, fluorescence, absorption, and/or scattering processes. EM effects typically are a dominant contributor to the signal attained in all of these techniques. Hence, in some embodiments, signal enhancement is engineered by designing the nano-LAMP to provide EM enhancement in the desired region(s). In certain embodiments, the nano-LAMP comprises reporter molecules embedded within one or more dielectric shells (although typically the outer silica shell is devoid, or substantially devoid, of reporter molecules). The embedded reporter molecules are shielded form chemical interactions with the metal layers, and the protective dielectric layer (i.e., the outer silica shell) shields external analyte molecules from direct contact with the outermost metal shell. Thus, in certain embodiments, chemical enhancement effects are excluded when designing the nano-LAMP structure. In embodiments of the disclosed nano-LAMPs, the electric-field distribution is designed to spatially confine the enhanced E-field to a particular region within and/or in the vicinity of the nano-LAMP particle. Trends can be determined by examining a set of calculated values as a function, e.g., size, composition, and/or excitation wavelength.

For surface-enhanced luminescence, fluorescence, or absorption, the electric field-induced change for a molecule located in the analytical volume scales as the square of local field while for surface-enhanced inelastic (Raman) scattering[9], the enhancement scales as the fourth power. The net enhancement or quenching factors can thus be evaluated as a volume integral of square or fourth power of local E-fields.

$$G_L = G_F = G_A = G = \iiint |E_{loc}(\omega_o)|^2 c_r dV \quad (18a)$$

or, $$G_R = \iiint |E_{loc}(\omega_o)|^4 c_r dV \quad (18b)$$

The concentration of analyte molecules in the volume of interest (V) is incorporated into the equation (18), by using a loading factor of concentration per unit volume, $c_r$. A uniform concentration is a simple scaling factor; hence, without loss of generality, $c_r$ is assumed to be 1%. An additional assumption is made that the molecules are uniformly dispersed in the dielectric layer(s) inside the particle or are uniformly dispersed outside the particle rather than being attached to the metal surfaces, for example as a self-assembled monolayer (SAM). While the case of SAMs is more complicated by the need to consider chemical coupling between the molecular species and metal, the EM mechanism dominates. Hence, the calculations can also be extended to SAMs as an approximation.

The parameters of significance for the model (FIG. 20) are the wavelength ($\lambda$) of incident EM wave, the number of layers in the sphere (L), radii of each layer ($r_1, r_2, \ldots r_L$) and relative refractive indices of each layer ($m_1, m_2, \ldots m_L$). The particle's environment can be considered to be the $(L+1)^{th}$ layer and the relative refractive index of an arbitrary $j^{th}$ layer is defined as $m_j = N_j/N_{L+1}$, where $N_j$ and $N_{L+1}$ are the refractive indices of $j^{th}$ layer and the embedding medium respectively. Since we are interested in the electric fields only, the sphere and surrounding medium are considered to have unity magnetic permeability. Without loss of generality, the incident field can then be represented by a plane wave propagating along z-axis and polarized along x-axis as:

$$E_{inc} = E_0 e^{i\kappa_{L+1} z} e_x \quad (19)$$

where $\kappa_{L+1} (= 2\pi N_{L+1} \omega_0)$ is the propagation constant of the surrounding medium.

The harmonic electromagnetic fields within different layers satisfy Maxwell's equations. To satisfy the continuity of fields at the spherical surfaces, the electric and magnetic fields are expanded using geometrically similar basis functions (vector spherical harmonics). Using such expansions, EM fields within each layer can be expanded in terms of spherical coordinates as:

$$E_j = \sum_{n=1}^{N} E_n \begin{bmatrix} \frac{-in(n+1)}{(\kappa_j r)^2} d_n^j \pi_n(\theta) \sin\theta \cos\phi \{\psi_n(\kappa_j r) - A_n^j \xi_n(\kappa_j r)\} e_r + \\ \frac{\cos\phi}{(\kappa_j r)} [c_n^j \pi_n(\theta)\{\psi_n(\kappa_j r) - B_n^j \xi_n(\kappa_j r)\} - \\ i d_n^j \tau_n(\theta)\{\psi'_n(\kappa_j r) - A_n^j \xi'_n(\kappa_j r)\}] e_\theta - \\ \frac{\sin\phi}{(\kappa_j r)} [c_n^j \tau_n(\theta)\{\psi_n(\kappa_j r) - B_n^j \xi_n(\kappa_j r)\} - \\ i d_n^j \pi_n(\theta)\{\psi'_n(\kappa_j r) - A_n^j \xi'_n(\kappa_j r)\}] e_\phi \end{bmatrix} \quad (20)$$

-continued $$H_j = (21)$$

$$-\frac{\kappa_j}{\omega}\sum_{n=1}^{N} E_n \begin{bmatrix} \frac{in(n+1)}{(\kappa_j r)^2} c_n^j \pi_n(\theta)\sin\theta\sin\phi\{\psi_n(\kappa_j r) - B_n^j \xi_n(\kappa_j r)\}e_r - \\ \frac{\sin\phi}{(\kappa_j r)}[d_n^j \pi_n(\theta)\{\psi_n(\kappa_j r) - A_n^j \xi_n(\kappa_j r)\} - \\ ic_n^j \tau_n(\theta)\{\psi_n'(\kappa_j r) - B_n^j \xi_n'(\kappa_j r)\}]e_\theta - \\ \frac{\cos\phi}{(\kappa_j r)}[d_n^j \tau_n(\theta)\{\psi_n(\kappa_j r) - B_n^j \xi_n(\kappa_j r)\} - \\ ic_n^j \pi_n(\theta)\{\psi_n'(\kappa_j r) - B_n^j \xi_n'(\kappa_j r)\}]e_\phi \end{bmatrix}$$

For the field in the core and incident field to be well defined at origin and at infinity:

$$a_n^1 = b_n^1 = 0, c_n^{L-1} = d_n^{L+1} = 1. \quad (22)$$

The other coefficients of expansion can be obtained enforcing continuity conditions between adjacent layers j and j+1 as:

$$(E_{j+1} - E_j) \times e_r = 0, (H_{j+1} - H_j) \times e_r = 0 \quad (23)$$

Thereafter, utilizing orthogonality of functions involved, a stable recursive formulation is implemented to obtain the coefficients $A_n^j$ and $B_n^j$ starting from the core and working outwards.

$$A_n^1 = 0, B_n^1 = 0 \text{ and for } j = 2, \ldots L \quad (24)$$

$$P_n^j = \frac{1}{m_j}\left\{\frac{R_n(\kappa_j r_j)D_n^{(1)}(\kappa_j r_j) - A_n^j D_n^{(3)}(\kappa_j r_j)}{R_n(\kappa_j r_j) - A_n^j}\right\} \quad (25)$$

$$Q_n^j = m_j\left\{\frac{R_n(\kappa_j r_j)D_n^{(1)}(\kappa_j r_j) - B_n^j D_n^{(3)}(\kappa_j r_j)}{R_n(\kappa_j r_n) - B_n^j}\right\} \quad (26)$$

$$A_n^{j+1} = -R_n(\kappa_{j+1} r_j)\left\{\frac{m_{j+1}P_n^j - D_n^{(1)}(\kappa_{j+1} r_j)}{m_{j+1}P_n^j - D_n^{(3)}(\kappa_{j+1} r_j)}\right\} \quad (27)$$

$$B_n^{j+1} = -R_n(\kappa_{j+1} r_j)\frac{Q_n^j - m_{j+1}D_n^{(1)}(\kappa_{j+1} r_j)}{Q_n^j - m_{j+1}D_n^{(3)}(\kappa_{j+1} r_j)}, \quad (28)$$

With available coefficients $A_n$ and $B_n$, the remaining coefficients $c_n$ and $d_n$ are obtained from $(L+1)^{th}$ layer and proceeding inwards in a recursive manner as:

$$c_n^{L+1} = 1, d_n^{L+1} = 1 \text{ and for } j = L, \ldots 1 \quad (29)$$

$$S_n^j = d_n^{j+1}\xi_n(\kappa_{j+1}r_j)\{R_n(\kappa_{j+1}r_n) + A_n^{j+1}\} \quad (30)$$

$$T_n^j = c_n^{j+1}\frac{m_j}{m_{j+1}}\xi_n(\kappa_{j+1}r_j)\{R_j(\kappa_{j+1}r_j) + B_n^{j+1}\} \quad (31)$$

$$d_n^j = \frac{S_n^j(\kappa_j r_j)}{\xi_n(\kappa_j r_j)\{R_n(\kappa_j r_j) + A_n^j\}} \quad (32)$$

$$c_n^j = \frac{T_n^j(\kappa_j r_j)}{\xi_n(\kappa_j r_j)\{R_n(\kappa_j r_j) + B_n^j\}} \quad (33)$$

By using an appropriate cutoff for the maximum order of VSH and stable recursive evaluations of logarithmic derivative and ratio functions involved[14], an accurate mathematical solution can be obtained for the coefficients and fields in each layer. For metal layers of thickness greater than 10 nm, it is typically acceptable to use the values obtained from bulk dielectric constants reported in literature. In nano-LAMPs including shells thinner than 10 nm, the imaginary part of the bulk dielectric constant is modified to account for restricted mean free path[8]:

$$\varepsilon = \varepsilon_{bulk} + ir_{j+1}\frac{\lambda_p}{L_{eff}}\left(\frac{v_F}{2\pi c}\right)\left(\frac{\lambda}{\lambda_p}\right)^3 \quad (34)$$

in which $\lambda_p$, $v_F$, c and $L_{eff}$ are respectively plasma wavelength, Fermi velocity, light velocity in vacuum and effective mean free path for electrons. The reduced mean free path for electrons is obtained using[8]:

$$L_{eff} = r_{j+1}\left\{\frac{1}{1+t^2} - \frac{t}{2} - \frac{(1-t)(1-t^2)}{4(1+t^2)}\ln\left(\frac{1-t}{1+t}\right)\right\}, \quad (35)$$

$$t = \frac{r_j}{r_{j+1}}$$

The Ricatti-Bessel functions, Bessel functions, and angular functions are calculated using recursion methods[14], integrals in the shells are evaluated using a numerical approach[11], and details of the GA-based optimization are discussed above. A minimum thickness constraint of 1 nm is imposed for the silica layers and of 2 nm on the metal layers. Similarly a size constraint of 10 nm is imposed for both metal and silica cores.

Figure 21:
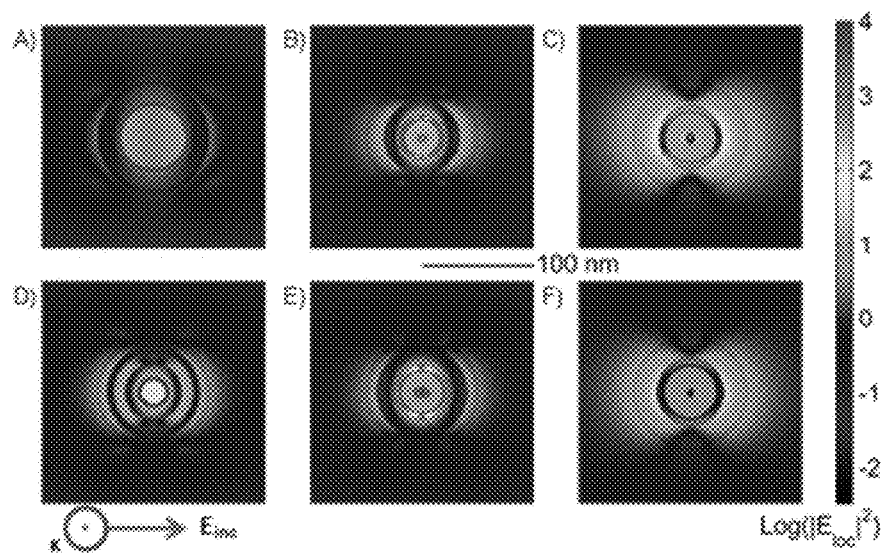
FIGS. 21A-21F illustrate optimization of local sensing ability for several embodiments of silver-silica nano-LAMPs when illuminated with an excitation wavelength of 785 nm. Hot spots are localized internally to innermost (21A, 21D), first outer (21B, 21E), and outermost (21C, 21F) silica layers by plotting E-field distributions in the xy-plane for 5-layered (21A, 21B, 21C) and 6-layered (21D, 21E, 21F) silver-silica nano-LAMPs. The radii for the nano-LAMPs are: 58, 62, 94, 99 and 100 nm (21A); 5, 32, 39, 67 and 100 nm (21B); 5, 7, 46, 56, and 100 nm (21C); 23, 27, 51, 72, 83 and 100 nm (21D); 5, 10, 39, 49, 81 and 100 nm (21E); and 5, 47, 49, 50, 60 and 100 nm (21F).

FIGS. 21A-21F illustrate the ability to localize the E-field, enhancement factor (G) and, hence, the sensitivity to different dielectric layers in 5-layered and 6-layered silver-silica nano-LAMPs (diameter=200 nm) at 785 nm excitation. The structures shown are designed such that ratio of total enhancement in a desired layer to that in other layers is maximized under the constraint of keeping the total size constant. For the 5-layered nano-LAMPs, the structure that maximizes the E-field to the silica layer between the first and second silver layers (FIG. 21B) possesses the largest G, as illustrated by the E-field distribution in the xy-plane. This structure has comparatively thicker metal shells. By increasing the dielectric core size and/or by reducing the thicknesses of metal layers, for example, it is possible to achieve the largest G values within core silica layer (FIG. 21A) or the outermost silica layer (FIG. 21C). Relatively similar structures, hence, can be tuned to provide spatially varied hot spots by adjusting the structure of the nanoparticle.

Similar results are observed for 6-layered silver-silica nano-LAMPs. When a larger silver core is chosen for the structure, the largest G is attained in the silica layer surrounding the core (FIG. 21D). The optimal structures to maximize G values in the outer silica layers (FIGS. 21E, 21F) comprise a smaller core and thicker outer metal shells. In some embodiments, however, the localization of the hot spots may diminish the absolute values of the maximum fields. For example, the absolute values of the maximum fields attained for the structures shown in FIGS. 21E and 21F are lower than the maximum field attainable in the silica layer surrounding the silver core. In terms of overall signal from the particle, the situation may be somewhat mitigated by the larger volume attained over the same radial distance from the core. Hence, a particular embodiment may utilize the inner or outer core amplification for a given size and structure of the particle depending on the particular conditions. The flexibility in tuning the position and strength of the EM localization as well as the interplay with the analytical test for which the particles are to be used represents an unprecedented opportunity to tailor the use of the disclosed nano-LAMPs as probes.

Figure 22:
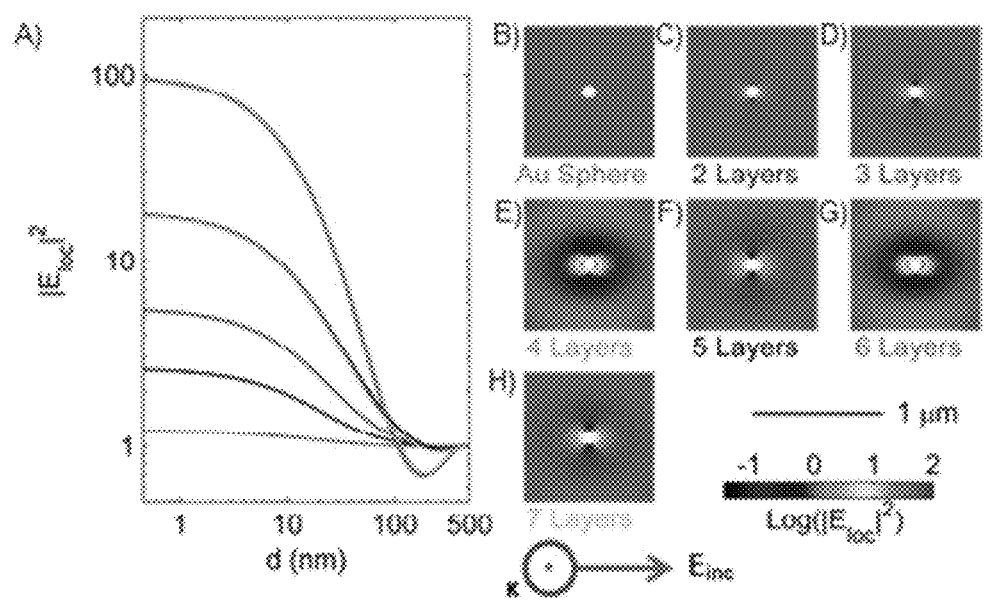
FIGS. 22A-22H illustrate embodiments of 100-nm gold-silica nano-LAMPs designed to localize a hot spot to the exterior of the structure. The electric field distributions in the xy-plane are shown for a bare gold sphere (22B) and nano-LAMPs comprising 2-7 layers (22C-22H, respectively) at 785 nm excitation. The E-field intensity along the x-axis with distance from the surface of each nano-LAMP is shown in 22A. The radii of layers in each structure are: 50 nm (22B); 27 and 50 nm (22C); 19, 35 and 50 nm (22D); 25, 38, 48 and 50 nm (22E); 7, 9, 10, 49 and 50 nm (22F); 5, 9, 25, 38, 48 and 50 nm (22G); and 16, 18, 19, 21, 32, 44 and 50 nm (22H). The nano-LAMP structures are shown in white for clarity in visualizing field distributions.

Embodiments of nano-LAMPs without reporter molecules can be designed to enhance the E-field and the response of exterior analyte molecules in their vicinity. For the purposes of calculation, a spherical analytical volume with the LAMP in the center is assumed. Ten times the probe size is chosen to approximate the entire analytical volume affected by a LAMP, as the EM fields decay exponentially away from its surface. FIG. 22A shows the electric field intensities along the x-axis for optimal 100 nm-sized gold-silica LAMPs comprising 2-7 layers at 785 nm excitation. Compared to a bare gold sphere, the attained enhancement can be much higher for nano-LAMPs. As the number of layers increase, the ability to extend the associated hot-spot further into the nano-LAMP environment increases. The hotspots attained with optimal embodiments of 4-layered and 6-layered gold nano-LAMPs (FIGS. 22E, 22G) are equally strong, as are the hot spots attained with the optimal embodiments of 5-layered and 7-layered gold-silica nano-LAMPs (FIGS. 22F, 22H). However, in certain embodiments, the odd-layered (dielectric core) structures provide a weaker electric field than the even-layered (metal core) structures.

As may be expected, there is an upper bound to the sensing volume around the particle. In an ideal case, the energy distribution outside the nano-LAMP can be made equal in magnitude to the energy distribution inside a nano-LAMP as it is simply a redistribution of the incident energy. The total enhancement of molecular signal, however, depends on the combined effect of the enhanced electric field and the volume over which it is distributed. Hence, direct comparisons of the enhancement capability inside and outside the LAMP are difficult.

From the results illustrated in FIGS. 22A-22H, for a 785-nm illumination and 100-nm nano-LAMP size, it was unexpectedly discovered that embodiments of nano-LAMPs with 4 layers provide maximal enhancement for this size. This finding is exceptionally relevant for the design and fabrication of such structures. Clearly, the fabrication complexity will increase as the number of layers increases. Hence, in certain embodiments, it will be advantageous to prepare a four-layer structure that can achieve a substantially similar response as a more complex structure with additional layers. Interestingly, the 4-layered and 6-layered structures exhibited a slight dip in the intensity between 100 nm and 500 nm (FIG. 22A). Without wishing to be bound by any particular theory, this dip may arise from the formation of a cold-spot due to the multipole interaction of the individual metal layers. The quenching indicates an alternative sensing strategy may be used in which the signal of the analyte is "bleached" in the sense of fluorescence photobleaching. As opposed to fluorescent photobleaching, however, there is no change in the sensed molecule, and its signal can be easily recovered as it exits the sensing volume defined by the nano-LAMP.

Figure 23:
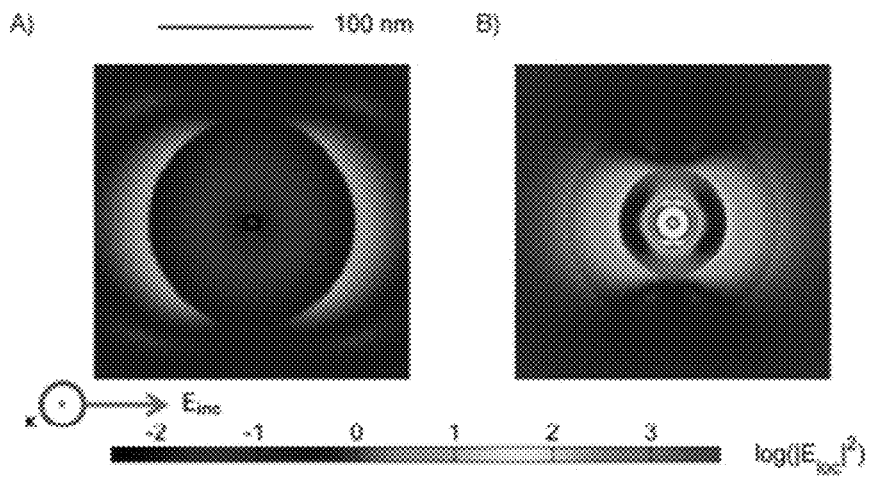
FIGS. 23A and 23B illustrate electric-field distributions in the xy-plane for two embodiments of 5-layered copper-silica nano-LAMP structures designed to have quenching (23A) or enhancing (23B) capabilities for embedded reporter molecules as an illumination wavelength of 633 nm. The geometric boundaries of the layers are depicted with black dotted circles and the radii of the nano-LAMPs are: 5, 7, 8, 98, and 100 nm (23A); and 5, 16, 23, 51 and 100 nm (23B).

The quenching behavior exhibited in FIG. 22A indicates that embodiments of nano-LAMPs with quenching capabilities may be prepared. A general strategy to design embodiments of quenching nano-LAMPs is to use thicker outer metal layers and design the structure to produce the smallest possible electric fields within the structure. For example, 5-layered copper-silica nano-LAMPs were designed to maximize or minimize the enhancement factor of contained reporter molecules at an excitation of 633 nm. FIGS. 23A and 23B illustrate the hot-spots and quenched cold-spots attained in the interior by plotting E-field distribution in the xy-plane. In both cases, the fields in the interior dielectric layers are enhanced (23B) or quenched (23A) up to three orders of magnitude compared to the exterior. Thus, a set of same sized probes having the same number of layers and chemical composition but having a range of responses can be created. In some embodiments, the combined use of enhanced and quenched nano-LAMPs produces a palette of probes with a designed sensitivity and a large dynamic range. Attaining high and low enhancements, the ability to adjust the analytical distance around the particle, and/or extending the dynamic range using the same particle size are advantages that cannot be attained using bare nanoparticles or simple structures.

Another facet of using the nano-LAMP framework is the ability to use materials that have not been previously utilized for sensing. For example, silver-silica structures have been used due to the large enhancements they offer in simple geometries and the desirable spectral location of their primary resonance peak(s). Similarly, gold-silica structures are very effective and preferable in biological detection purposes due to the inert nature of gold. However, copper-silica structures have not been thoroughly examined. The results demonstrated with copper-silica nano-LAMPs indicate that high enhancements and tunability of the sensitivity, sensing volume, and/or location of plasmonic peaks may be achievable with materials that have never been used for nanoparticle sensing, potentially leading to less costly and new routes of fabrication. In certain embodiments, the nano-LAMP design methods disclosed herein may enable incorporation of additional properties such as magnetic response without compromising the optical sensing capability.

In addition to the flexibility in use of materials, embodiments of the disclosed nano-LAMPs facilitate detection of analytes with varying concentrations by using multiple illumination wavelengths. As shown in FIG. 11, some embodiments of the disclosed nano-LAMPs produce a flat spectral response when illuminated with multiple excitation wavelengths, thereby allowing the same nano-LAMP structure to be used effectively at different wavelengths. In certain embodiments, however, a single nano-LAMP can act as either an amplifier or a quencher of the response at different wavelengths. For example, a single nano-LAMP can be designed to enhance the interior reporter signal at 532-nm illumination while quenching the interior reporter signal at 785-nm illumination, two wavelengths commonly used for excitation in Raman spectroscopy. Such nano-LAMPs are advantageous for use in multimodal detection, where the same structure can be used to detect the presence of highly abundant species (by selecting an excitation frequency that quenches, or minimizes, the response) and low concentration species (by selecting an excitation frequency that enhances the response) by employing two different wavelengths.

Figure 24:
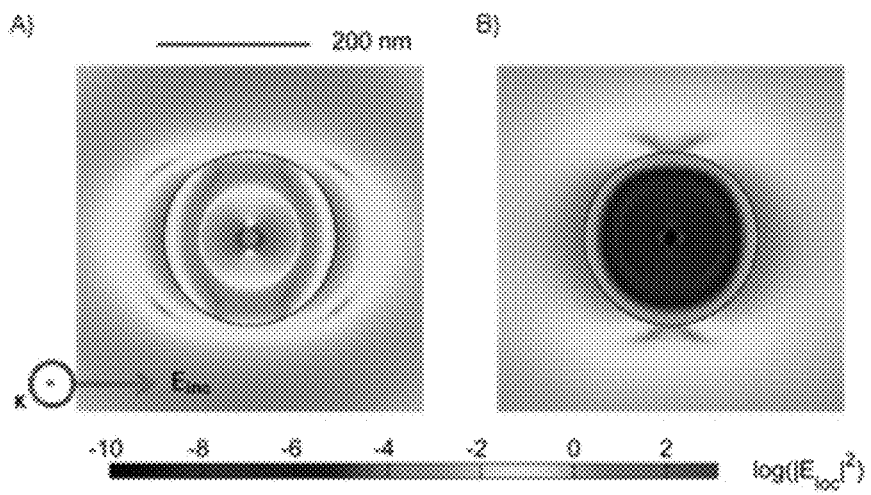
FIGS. 24A and 24B illustrate electric-field distributions in the xy-plane for one embodiment of 4-layered silver-silica nano-LAMP having an enhanced sensing capability in its interior at an excitation frequency of 532 nm (24A) and a quenched sensing capability at an excitation frequency of 1064 nm (24B). The radii of layers in the nano-LAMP are 23, 115, 199, and 200 nm.
Figure 25:
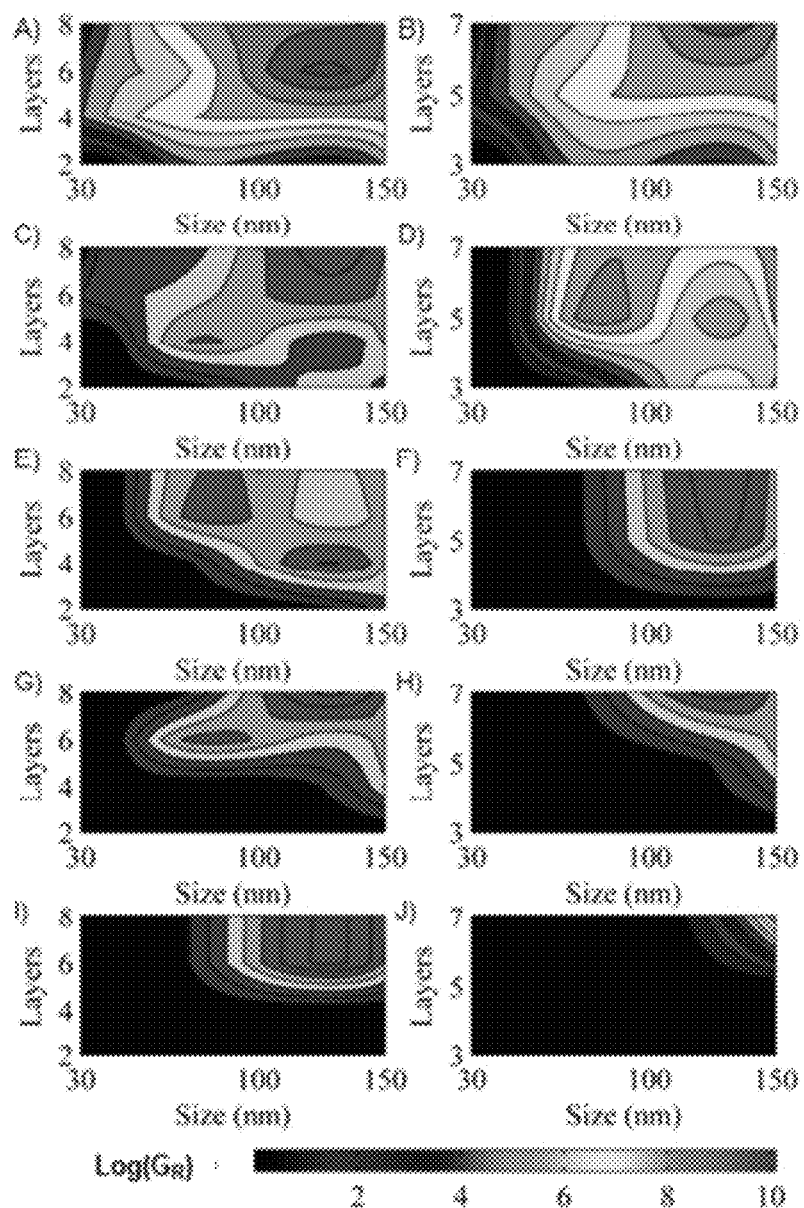
FIGS. 25A-25J are plots illustrating optimal Raman enhancement factors ($G_R$) attained for embodiments of gold-silica nano-LAMPs as a function of total particle size while maintaining a given contrast ratio (CR). The attainable GR is shown for even-layered nano-LAMPs having CR values of 0.1 (25A), 1 (25C), 10 (25E), 100 (25G), and 1000 (25I), and for odd-layered nano-LAMPs having CR values of 0.1 (25B), 1 (25D), 10 (25F), 100 (25H), and 1000 (25J).

In some embodiments, a dynamic sensing range of over 5 orders of magnitude, over 8 orders of magnitude, over 10 orders of magnitude, or even over 12 orders of magnitude is attainable by using two wavelengths with a single nano-LAMP. The ease of designing LAMPs with such multiple excitation capabilities is typically higher for LAMPs of larger sizes. In one embodiment, a larger size of 400 nm was selected to design an embodiment of a 4-layered silver-silica nano-LAMP having an enhanced interior sensing capability at 532-nm illumination and a quenched interior sensing capability at 1064 nm. The designed nano-LAMP has layers with radii of 23, 115, 199, and 200 nm. FIGS. 24A and 24B illustrate the electric field distributions in the xy-plane for the 4-layered silver-silica nano-LAMP. For applications where the nanoparticle size is constrained (e.g., in vivo applications), calculations can be performed to determine the configuration of an optimal enhanced-quenched pair for any given size and/or wavelengths.

When used for Raman sensing, the sensitivity of a nano-LAMP having a particular analytical volume can be quantified by the enhancement factor G, and the specificity (selectivity) can be quantified by using a contrast ratio defined as:

$$CR = \frac{G_R^{LAMP}}{G_R^{Vicinity}} \tag{36}$$

where $G_R^{LAMP}$ is the Raman enhancement achieved for the reporter volume in the nano-LAMP and $G_R^{Vicinity}$ is the Raman enhancement attained for the analyte volume in the relevant vicinity. The relevant vicinity is defined by a 1 μm sphere with the nano-LAMP at its center, as disused previously.

Designing labels with optimal sensitivity, while maintaining a particular contrast ratio (i.e., the ratio of the probe signal to the background "noise"), is of significance in biological imaging applications for accurate quantification of tagged molecules. For example, nano-LAMPs of various sizes with both high enhancement and high contrast ratios at 785 nm illumination (a commonly used excitation frequency for biological applications) can be designed for biomedical sensing. The genetic algorithm can be set to determine nano-LAMP structures having a contrast ratio that is equal to or greater than a selected value. FIGS. 25A-25J depict the optimal enhancement factors achieved for gold-silica nano-LAMPs of different sizes and different numbers of layers with different contrast ratios. The sizes considered ranged from 30 nm to 150 nm, which is a relevant size range for biological detection purposes. The results demonstrate that the optimal enhancement factor, $G_R$, and contrast ratio, CR are inter-related. The CR can be considered to be the ratio of the signal of the probe to the "noise" of the analytical background. This is the worst possible case as it assumes that the background and the reporter molecules have total spectral overlap. If there is no spectral overlap, the noise is dominated by measurement noise. Considering enhancement at several contrast ratios that may be expected or desired in experiments allows the preferred sizes and structures for a particular application to be determined. As the desired CR increases, some sizes and numbers of layers may be unable to meet the criterion for minimum CR. Embodiments of nano-LAMPs that are unable to produce the desired CR are depicted in black in the contour plots (25A-25J), indicating that there is no signal enhancement obtained. As the CR increases, embodiments of nano-LAMPs having a larger size may be utilized to achieve the desired result. This is a direct consequence of both confining the fields to within the particle physically, as well as structuring the numbers of layers such that the inner core is more enhanced relative to remainder of the nano-LAMP and/or the vicinity outside the nano-LAMP. The results also demonstrate that desired contrast ratios can be achieved with higher enhancements and smaller size using embodiments of nano-LAMPs including an even number of layers compared to embodiments of nano-LAMPs including an odd number of layers.

D. Effect of Non-Specificity in Shape, Size and/or Dielectric Properties

Fabrication approaches may introduce variability into the nano-LAMP structure. In particular, enhancement may be affected by variability in size, shape, and dielectric environment. As previously discussed, embodiments of the disclosed nano-LAMPs comprising non-resonant organic reporters are capable of producing NEFs of ~$10^3$-$10^{12}$, such as $10^3$-$10^{10}$, $10^5$-$10^{10}$, $10^5$-$10^{12}$, or $10^8$-$10^{12}$. When using a resonant organic reporter, NEFs of ~$10^{14}$ $10^{15}$ are achievable, such as NEFs from $10^6$-$10^{14}$, $10^8$-$10^{15}$, $10^{10}$-$10^{15}$, or $10^{12}$-$10^{15}$.

However, embodiments of the disclosed nano-LAMPs comprise extremely thin metal and silica shells stretching the limits of fabrication. As a consequence, determining the theoretical predictions of ideal and distorted structures can facilitate development of fabrication processes that produce multiple well-controlled nanolayers.

As described above, each nano-LAMP layer can be formed by attaching a plurality of nanoparticle seeds onto the core or the previous layer, and then growing the seed layer into a continuous shell. If the nanoparticle seeds are metal, additional metal can be reduced onto the structure to form a continuous metal shell. If the nanoparticle seeds are silica, or reporter-embedded silica, additional silica can be fused onto the structure to form a continuous dielectric or reporter-embedded dielectric layer. Although established techniques exist for each step[23], each step may introduce considerable variability into the final structure. For example, the variability in sizes of nanoparticle seeds can result in a slight variation in the final shape of structure. Also, variability in fusing silica or reducing metal shells can result in a slight variation in the thicknesses of the layers. While estimating size irregularities is possible either in design or electron microscopy measurements of the fabricated structures, care must also be taken to account for the sharp change in material properties with size at this length scale. The standard refractive index profiles available for bulk metal are not applicable for thin metal shells that are comparable in size to the mean free path of conduction for electrons.[8] Similarly the fabrication approach can introduce small voids within the layer that result in a change the dielectric properties of metal and silica. Predicting the effect of small various induced in size, shape, and/or dielectric properties of nano-LAMPs increases an understanding of the stability and variation of optical responses of nano-LAMPs with changes in different geometric and material parameters.

Although the actual response of reporter molecules within the dielectric shells can be influenced by enhancement due to chemical charge transfer effects, electromagnetic effects are dominant. Additionally, the uniform distribution of reporter molecules within the silica shells minimizes the surface-active sites and chemical enhancement effects. Thus, the variability analysis can focus solely on electromagnetic scattering by the nano-LAMPs. Analytical solutions for scattering and absorption characteristics of nano-LAMPs are obtained by layered Mie theory as described above. Since the particles considered are much smaller than the incident wavelength of excitation, it suffices to consider a single plane wave excitation instead of a focused incident beam. Electromagnetic fields within each layer are expanded in in vector spherical harmonics. Utilizing conditions of continuity at the layer interfaces, a recursive formulation is used to evaluate coefficients of expansion. The recursive formulation involves analytical functions such as logarithmic derivative and ratio functions. Using appropriate cutoffs for the maximum order of VSH and these analytical functions[14], the expansion coefficients and the internal fields can be evaluated. For metal layers of thickness greater than 5 nm, it bulk values are acceptable. In embodiments including metal shells thinner than 5 nm, a size-based correction[8] is implemented to account for the intrinsic size effects due to reduced mean free path of electrons.

The interaction between surface plasmons associated with different metal shells in nano-LAMPs determines their optical properties. The coupling of dipolar resonances results in stronger long-wavelength resonances, while higher order multipole coupling results in short-wavelength resonances. The contributions and interplasmonic coupling from different shells also lead to a local reorganization of electric field both within and in the vicinity of nano-LAMPs. The internal electromagnetic distributions contribute to the overall enhancement of dye molecules embedded and signal from the nano-LAMP. A convenient measure of signal enhancement is the signal delivered by the nano-LAMP compared to what would have been recorded directly from the analyte molecule in the absence of the nano-LAMP. The relative strength of interaction and manifestation of resonances is dependent on the overall size of the particle, relative thicknesses of the layers, and/or composition (refractive indices) of individual layers. Even a slight variation in these parameters could significantly affect the overall response of the particle recorded by far-field optical configurations and can cause a deviation from the predicted values by changing local field distributions.

The optical responses of metal nanoparticles are strongly dependent on the refractive indices of the chosen materials. The real part of the refractive index determines the energy scattered while the imaginary part determines the energy absorbed. For nano-LAMPs, the energy reaching each shell is dependent at least in part on the attenuation of the outer shells. The overall scattering and absorption is thus a cumulative superposition of the scattering and absorption due to individual shells. Any variability in refractive index values for any metal layer can affect both far-field and near-field characteristics. In the literature, the refractive index profiles of gold, copper and silver are usually taken from two sources.[24, 25] These experimental profiles differ to a small extent in some of the wavelength regions. To demonstrate the effect of refractive index variability, the differences in optical characteristics of a nano-LAMP are calculated using the two profiles. In all cases described herein, nano-LAMPs with silica shells of dielectric constant 2.04 are modeled; the nano-LAMPs are considered to be embedded in a water-like media with dielectric constant 1.77.[26]

Figure 26:
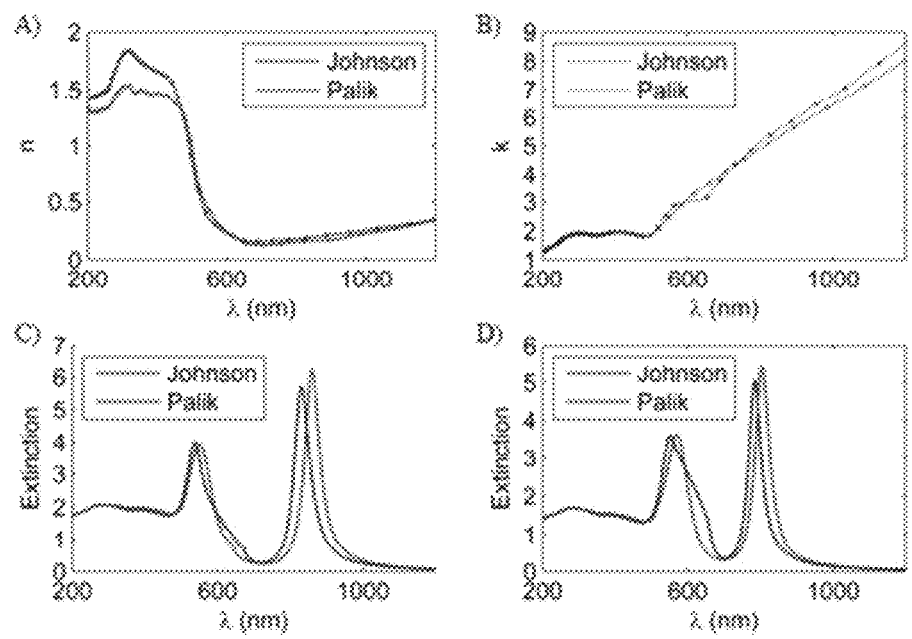
FIGS. 26A-26B are dispersion profiles for real (26A) and imaginary (26B) parts of the refractive index for gold-silica nano-LAMPs.
FIGS. 26C-26D are graphs of extinction efficiency versus wavelength illustrating extinction efficiencies for a 4-layered gold-silica nano-LAMP (26C) with radii: {26, 34, 44, 50 nm} and a 6-layered gold-silica nano-LAMP (26D) with radii: {5, 12, 22, 31, 41, 50 nm}.

FIGS. 26C-26D illustrate the influence of a slight change in refractive index on the extinction efficiencies of 50 nm-sized 4-layered and 6-layered gold-silica nano-LAMPs. The differences in refractive indices obtained from smooth interpolation from experimental values given in the two sources are shown in FIG. 26A and FIG. 26B, respectively. The real parts differ slightly, primarily in the ~200-500 nm spectral region; the imaginary parts differ slightly as well, primarily in the ~600-1000 nm region. The extinction of 4-layered (FIG. 25C) and 6-layered (FIG. 25D) nano-LAMPs have two dominant resonance peaks, one at long wavelength due to coupling of dipolar resonances and one at shorter wavelength due to coupling higher order multipole resonances. The locations of both dipolar and higher order multipole resonances shift slightly towards longer wavelengths when using data sets from Johnson et. al.[24] The shift to longer wavelength resonance is greater and significant, about 30 nm in case of 4-layered structures and about 20 nm in case of 6-layered structures. The cumulative contribution of different gold layers, thus, not only increases the signal but also amplifies the dependence of extinction on refractive index value chosen. Also it can be noticed that absorption plays a dominant role in these profiles, and shifts in resonances are consistent with shifts in the absorption index values. Given that the Johnson et al.[24] and Palik[25] values are largely used by those of ordinary skill in the art of calculating materials' responses, it may be fair to estimate that the fabrication uncertainty is of the same order. Though the resonance peaks are different, the peaks are broad enough that substantial enhancement may be obtained with narrowband excitation lasers within the peak resonance. Thus, embodiments of the disclosed nano-LAMPs can be used effectively, despite the potentially significant uncertainty in designing the structures.

Figure 27:
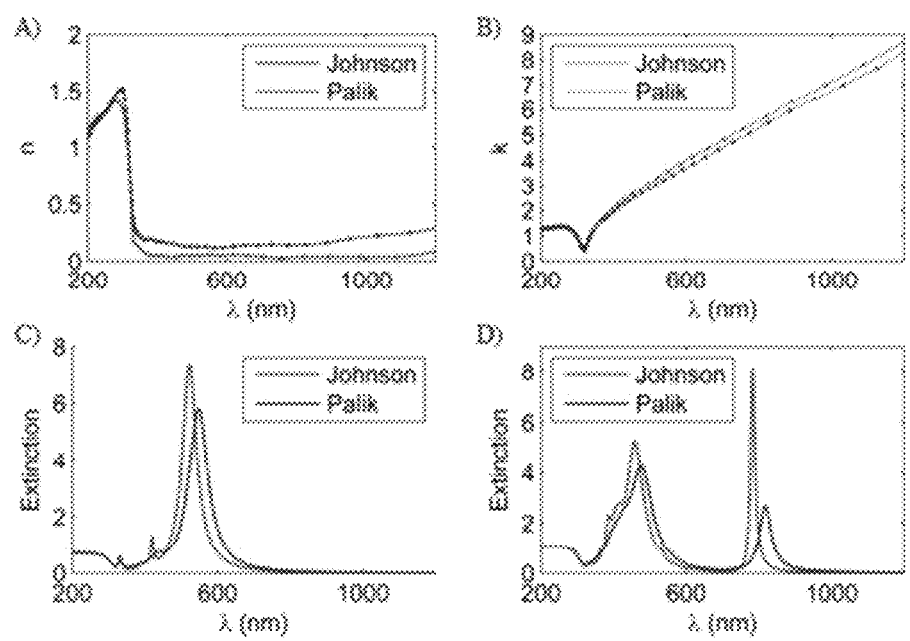
FIGS. 27A-27B are dispersion profiles for real (27A) and imaginary (27B) parts of the refractive index for silver-silica nano-LAMPs.
FIGS. 27C-27D are graphs of extinction efficiency versus wavelength illustrating extinction efficiencies for a 4-layered silver-silica nano-LAMP (27C) with radii: {5, 22, 32, 50 nm} and a 6-layered silver-silica nano-LAMP (27D) with radii: {5, 10, 20, 25, 35, 50 nm}.
Figure 28:
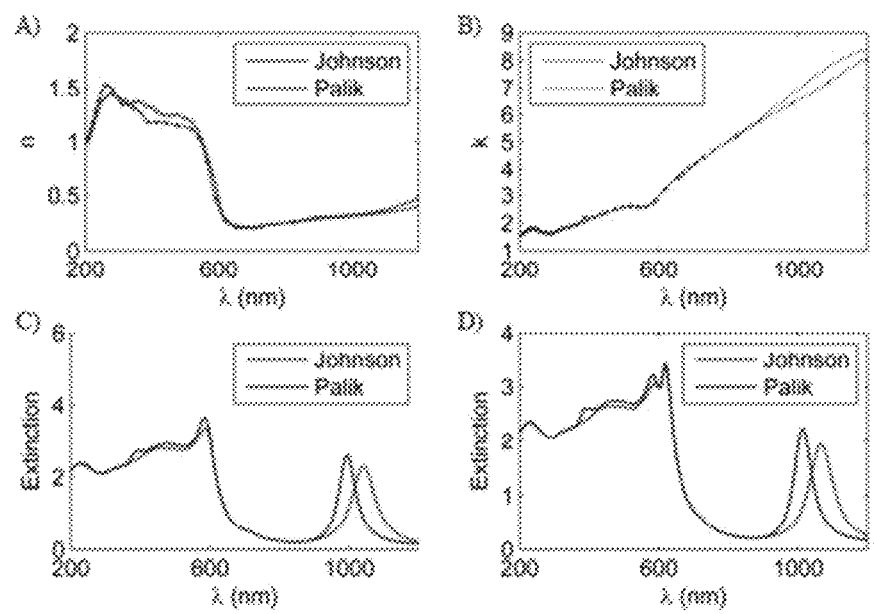
FIGS. 28A-28B are dispersion profiles for real (28A) and imaginary (28B) parts of the refractive index for copper-silica nano-LAMPs.
FIGS. 28C-28D are graphs of extinction efficiency versus wavelength illustrating extinction efficiencies for a 4-layered copper-silica nano-LAMP (28C) with radii: {30, 35, 45, 50 nm} and a 6-layered copper-silica nano-LAMP (28D) with radii: {10, 15, 30, 35, 45, 50 nm}.

In the visible and NIR spectral regions, broadband illumination is often chosen for analysis, and nanoparticles preferably have a distinct pattern of narrow lines for these applications. Embodiments of silver-silica LAMPs can be designed to have stronger and narrower resonances than other metals. However, with structures that possess such stronger interplasmonic coupling between the metal shells, the changes in extinction profiles with any slight changes in refractive index are also more obvious. For example, FIGS. 27C and 27D show extinction efficiencies of 4-layered and 6-layered silver-silica nano-LAMPs, respectively, along with the dispersion profiles of refractive index (FIGS. 27A, 27B) presented in both sources. The real (FIG. 27A) and imaginary (FIG. 27B) parts of refractive index differ considerably in the wavelength ~300-1200 nm. The extinction efficiencies obtained using calculations with refractive indices obtained from Palik[25] are much smaller, especially in case of 6-layered nano-LAMPs. The resonances are shifted towards right to about ~25 nm in case of both 4-layered and 6-layered LAMPs. The shifts in profiles in these cases are also in direct agreement with shifts in the absorption index. However, in the case of silver-silica nano-LAMPs, considerable differences exist in the real part of the refractive index as well leading to higher differences in the overall extinction. Hence, for broadband illumination applications, embodiments of silver-silica nano-LAMPs may be less tolerant of design and fabrication variations than gold-silica nano-LAMPs.

Similar calculations of extinction were made for 4-layered and 6-layered copper-silica nano-LAMPs (FIGS. 28A-28D). The plasmonic resonances of copper are smaller in comparison to gold and silver in the illumination band and for the sizes considered here. But it can be clearly observed that the slight change in absorption index values indicating a slight shift towards longer wavelengths in the absorption index directly result in a shift towards longer wavelengths in resonance peaks.

Figure 29:
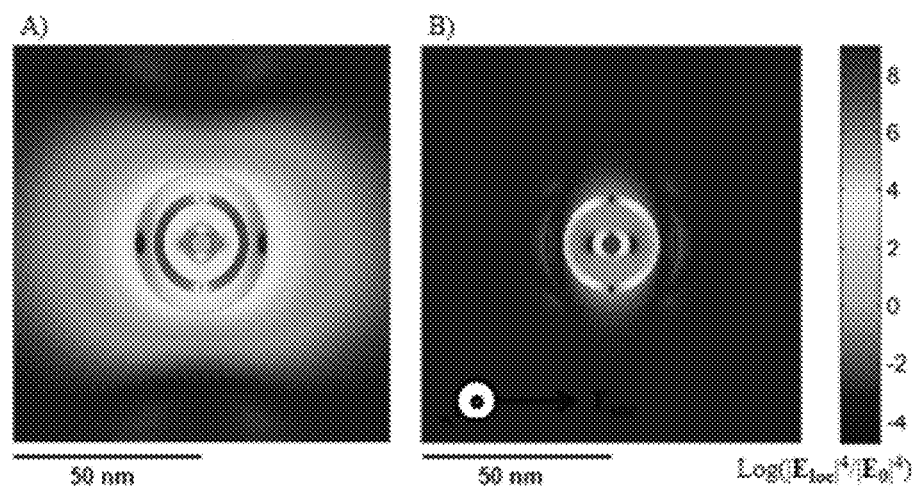
FIGS. 29A-29B illustrate the differences in internal field distribution present when a 6-layered silver-silica nano-LAMP with radii {5, 10, 20, 25, 35, 50 nm} is illuminated by a 785-nm plane wave using two refractive index profiles.

The results demonstrate that non-specificity in the choice of refractive index values when validating the LAMP structures may result in variability between theoretically predicted and experimentally obtained far-field characteristics. Typically, the refractive indices can be calculated by fitting experimental values with theoretical predictions from nanoparticles. However, the variability in size and shape within metal nanoparticles (and/or nano-LAMPs) may result in variability in the obtained refractive index profiles. To make accurate predictions, a range of refractive index values at each wavelength that could theoretically fit the extinction value based on the range of sizes for nanoparticles can be obtained. Such variability may also lead to pronounced effects in the internal hot-spots generated depending on the sizes of the layers. For example, FIGS. 29A and 29B show the differences in internal electromagnetic field distribution in a 6-layered silver-silica nano-LAMP at 785 nm excitation using refractive index profiles from Johnson et al.[24] (29A) and Palik[25] (29B). The calculations made using the refractive indices from both sources differ, and the highest Raman enhancement obtained may differ up to two orders of magnitude in the outer silica shell.

The differences in hot-spots generated may significantly lower the overall response of the nano-LAMP as well as the hot-spot generated in and around it. In case of refractive indices from Johnson et al.[24], the real part of the refractive index is lower and the absorption index is higher at 785 nm. In this case, the absorption from the outer metal shells is greater, resulting in higher energy reaching the internal metal surfaces and then scattered. The absorbed radiation from outside shells and scattered radiation result in stronger plasmonic coupling and generation of hot-spots of higher intensity and extent both internally and externally. An understanding of such variability can thus facilitate engineering a probe structure for desired hot-spots and validating the proposed structure. The LAMP geometry with its multiple layers provides more design flexibility than simple structures such as nanoshells. The layer spacings and dielectric properties provide additional parameters that can be optimized to provide properties closer to those desired.

Figure 30:
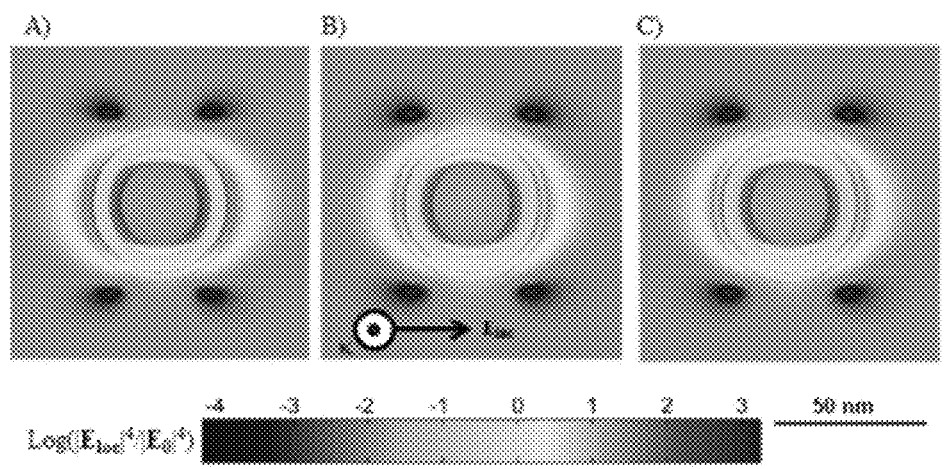
FIGS. 30A-30C illustrate the internal field distributions present when a 4-layered gold-silica nano-LAMP with radii {26, 34, 44, 50 nm} is illuminated by a 532-nm plane wave, considering silica refractive index dispersion (30A), silica-1% Rhodamine refractive index (30B), and silica-10% Rhodamine refractive index (30C).

The optical characteristics of LAMPs are also dependent on the dielectric properties of the silica shell. It is a common practice to use a dielectric constant of 2.04 for fused silica.[26] In the spectral regions being considered, however, silica has a slight dispersion profile. Also, embedded reporter molecules may make the silica shell slightly absorptive. To investigate this effect, the internal field distribution in a four-layered gold-silica nano-LAMP when illuminated by 532 nm plane wave is considered (FIGS. 30A-30C). The silica shells are considered to have a refractive index of 1.547[27] and are filled with rhodamine with a refractive index of $1.42+0.01i$.[28] The final refractive index has been calculated by using volumetric weightage. A comparison of calculations made for nano-LAMPs with silica of refractive index 1.43 (30A) with nano-LAMPs with silica with its actual refractive index value linearly combined with 1% Rhodamine (30B) and 10% Rhodamine (30C) are shown.

In the example considered above, the extent and intensity of hot-spots generated does not vary significantly, but a slight change in the fields generated just outside the LAMP can be noticed. Rhodamine has molecular resonance only in the case of wavelength of excitation interest 532 nm, and hence only this wavelength is considered. Notably, the effect of changing the properties of the metal layers is significantly different from changing properties of the dielectric. Hence, in some embodiments, fabrication efforts emphasize maintaining the properties of metal layers. Accurately measuring and modeling the properties as a function of layer thickness, crystal structure, and/or volumetric properties (e.g. voids) also affect nano-LAMP performance.

Spheroidal particles of higher aspect ratio have the capability to generate narrower resonances and/or shift the resonance to longer wavelengths compared to spherical particles. They can also generate higher intensity hot-spots at the tips of the structures in the long-axis. Use of non-spherical particles, however, can present a disadvantage in applications due to dependence of their optical response on the direction and polarization of the illuminating radiation. Spherical particles such as nano-LAMPs provide for ease in fabrication compared to spheroidal particles, as well as elimination of any non-isotropic illumination.

Figure 31:
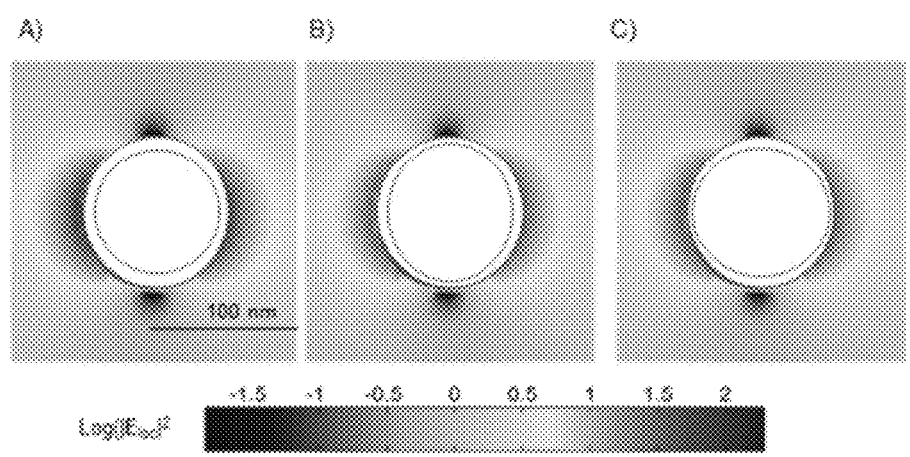
FIGS. 31A-31C illustrate the external field distribution of a gold-silica nanosphere {gold core—50 nm, silica shell—10 nm} when illuminated by 532 nm plane EM wave. Calculations are shown for spherical core (31A), prolate spheroidal core (long axis diameter—45 nm, short axis diameter—40 nm} (31B), and oblate spheroidal core (long axis diameter—45 nm, short axis diameter—40 nm} (31C). The outer shell surface is kept spherical and of constant size.
Figure 32:
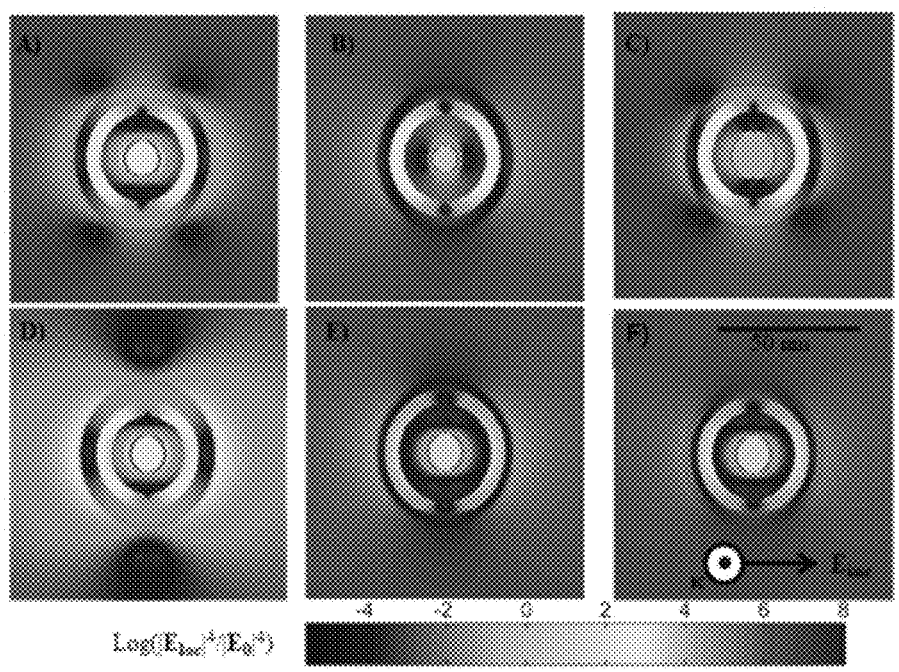
FIGS. 32A-32F illustrate the effect on the local field distribution of slight size variation in the metal layers of gold-silica nano-LAMPs when illuminated by a 532-nm plane EM wave: {7, 8, 16, 22, 29, 30 nm} (32A); {5, 6, 18, 24, 29, 30 nm} (31B); {9, 10, 18, 24, 29, 30 nm} (32C); {7, 8, 16, 22, 29, 30 nm} (31D); {7, 8, 20, 26, 29, 30 nm} (32E); {7, 8, 18, 24, 27, 30 nm} (32F).

During fabrication of nano-LAMPs, however, variation in the spherical shape of the shells could result. FIGS. 31A-31C show the external field distribution of a silica-gold nanoshell evaluated through discrete-dipole approximation.[29] The refractive index value used for gold is taken from Johnson et al.[24], and 1.43 is used as the refractive index for the silica. As the core is changed from spherical (FIG. 31A) to prolate (FIG. 31B) and then to an oblate spheroidal core (FIG. 31C), the extent and the intensity of the external hot-spot generated is not affected to any significant level. This example demonstrates a simple variability in shape, and many other effects like bumps and craters as well as a Gaussian shape to the surfaces can be considered. These effects are likely to change the maximal local field generated, and the low concentration loading of the reporter molecules decreases the likelihood of reporter molecules being at such hot-spots. Multiple layers having different shapes may affect the enhancement, but the above example shows that the hot-spot will not vary in simpler cases with small changes in the shape. In cases having multiple shells that vary in different ways, the overall effect is difficult to predict due to the coupling of resonances between layers. Nevertheless, small variations in shapes of the inner layers are not likely to have a dramatic effect on the performance of the nano-LAMP.

As set forth above, size-induced changes in refractive indices of metals may have a significant effect, and a correction is employed for nano-LAMPs including metal shells thinner than 10 nm. Additionally, some variation in size may occur during fabrication. The contributions from different metal shells in the overall response and plasmonic coupling may vary with changes in the sizes of the layers. When designing nano-LAMPs, layer sizes are varied to achieve a desired hot-spot or response. However, the fabricated structures could include slightly differing layer sizes due to variations in fabrication conditions. FIGS. 32A-32F show the internal field distributions of a 6-layered gold-silica LAMP when illuminated by a 532 nm plane EM wave. The standard refractive index of 1.43 for silica is used, and bulk values from Johnson et al.[24], have been used for the refractive indices of gold. The results are shown for the reference structure in FIG. 32A, and slight changes to the size of the metal core and outer metal layers have been made in the other sections. The intensity and extent of hot-spots generated in each case are similar to that of the reference (FIG. 32A), and since the dielectric spacing is kept constant the volumetric summing of enhancement for the reporter molecules is expected to remain the same. This example demonstrates that slight size variation of the metal shells does not result in any significant variation in the hot-spot and hence the overall response for the nano-LAMP structures for a given wavelength of excitation.

The properties of nano-LAMPs are primarily dependent on the sizes of the individual layers and the dielectric properties of these layers. As demonstrated above, the variation in dielectric properties can result in differences in the overall responses. However, slight changes in size and shape do not significantly affect the optical responses, and aggregate structures may be designed to eliminate any variability due to small changes in these parameters.

E. Methods of Making Nano-LAMPs

Figure 33:
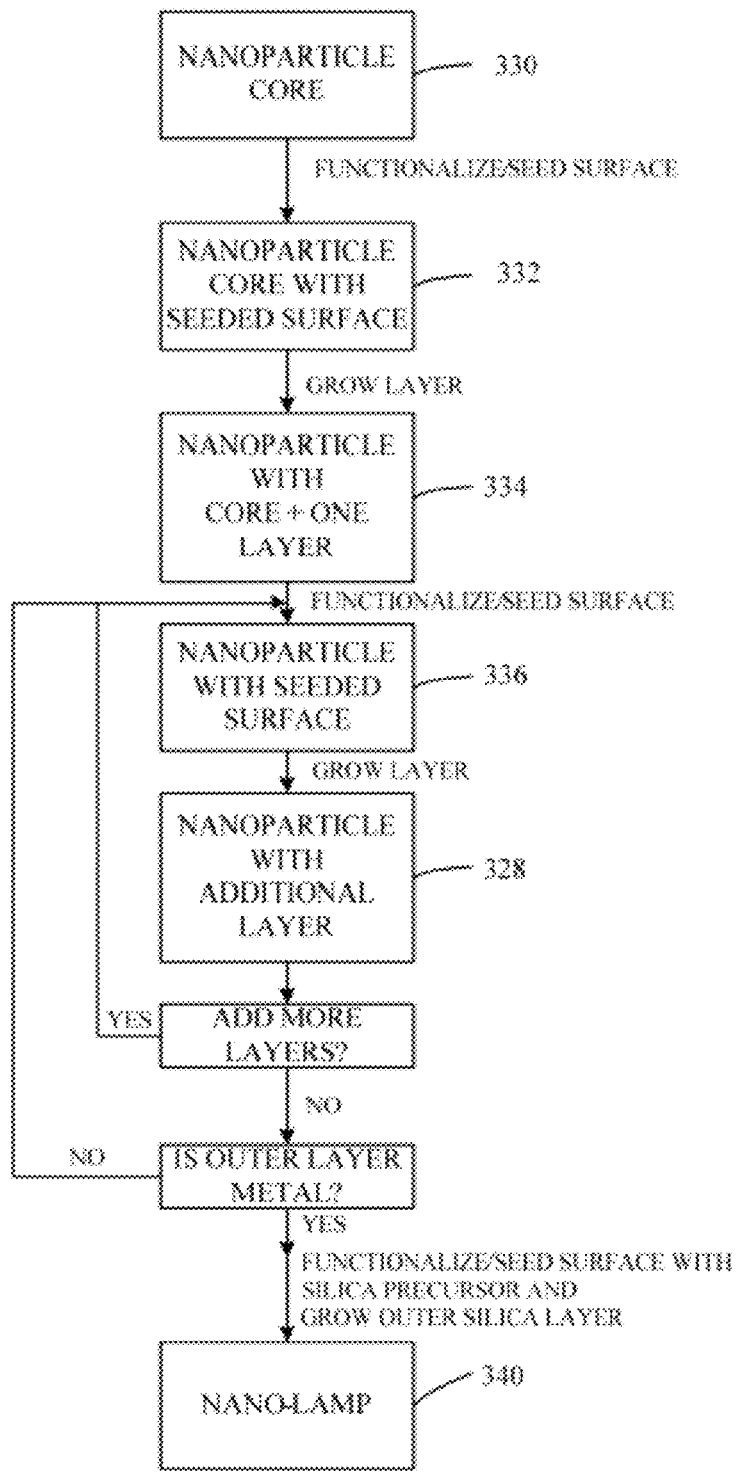
FIG. 33 is a flow diagram of one embodiment of a method for making the disclosed nano-LAMPs.

An overview of a representative method for making nano-LAMPs is illustrated in FIG. 33. A nano-LAMP is prepared by depositing alternating dielectric and metal layers onto a metal or dielectric nanoparticle core 330. If nanoparticle core 330 is metal, the first layer added will be dielectric. If nanoparticle core 330 is dielectric, the first layer added will be metal. In some embodiments, each concentric layer, or shell, in a nano-LAMP is produced in two steps.[19,20] The first step comprises functionalizing and seeding the nanoparticle surface with a plurality of metal or dielectric seeds that are attached to the previous layer or core, thereby producing a nanoparticle with a seeded surface 332. If the layer to be added is metal, metal seeds are used. If the layer to be added is dielectric, dielectric seeds are used. In one embodiment, the seeds include a functional group capable of reacting with the nanoparticle surface, thereby attaching the seeds to the surface. In this embodiment, functionalizing and seeding occur simultaneously. For example, methoxy-polyethylene glycol-thiol (mPEG-thiol) or methoxy-polyethylene glycol-amine (mPEG-amine) can used to both functionalize and seed a gold surface, wherein the thiol or amine group, respectively, binds to the gold surface and the polyethylene glycol chain acts as a dielectric seed. In another embodiment, the nanoparticle surface is functionalized with a molecular linker to provide a functional group useful for attaching the seeds. For example, silane linkers are capable of binding to silica surfaces, and linkers comprising amino and/or thiol groups are capable of binding to gold. Thus, in one embodiment, an amino silane (e.g., aminopropyltrimethoxy silane (APTMS)) is used to functionalize a silica layer with amino groups prior to attaching gold nanoseeds. In another embodiment, a cDNA may be used to functionalize the silica layer prior to attaching the gold nanoseeds. The second step comprises growing the seed layer into a continuous shell by reducing metal onto it in case of metal shells and fusing silica in case of silica layer, thereby producing a nanoparticle 334 comprising a core and one layer.[21] The outer surface of the layer then is functionalized and seeded to produce a nanoparticle with a seeded surface 336 in preparation for adding another layer. The next layer then is grown to produce a nanoparticle 338 with a core, a first layer, and at least one additional layer. If one or more additional layers are to be added, the steps of functionalizing/seeding the surface and then growing the next layer are repeated until the desired number of alternating dielectric and metal layers are achieved, with the final layer being metal. The outermost metal surface is functionalized and seeded, e.g., with m-PEG-thiol, and a protective outer silica shell is grown, e.g., by reducing TEOS onto the seeded surface. The final nano-LAMP 340 includes a core, alternating dielectric and metal layers, and an outer silica shell.

Reporter molecules can be included in at least one dielectric layer other than the outer silica layer. In one embodiment, the reporters are added during the steps of functionalizing/seeding the previous metal surface. In another embodiment, the reporters are added during the step of growing the dielectric layer. In one embodiment, reporters are added to a plurality of dielectric layers, and the reporters in each layer have the same chemical composition. In another embodiment, reporters are added to a plurality of dielectric layers, and the reporters in at least two of the dielectric layers have a different chemical composition.

Figure 34:
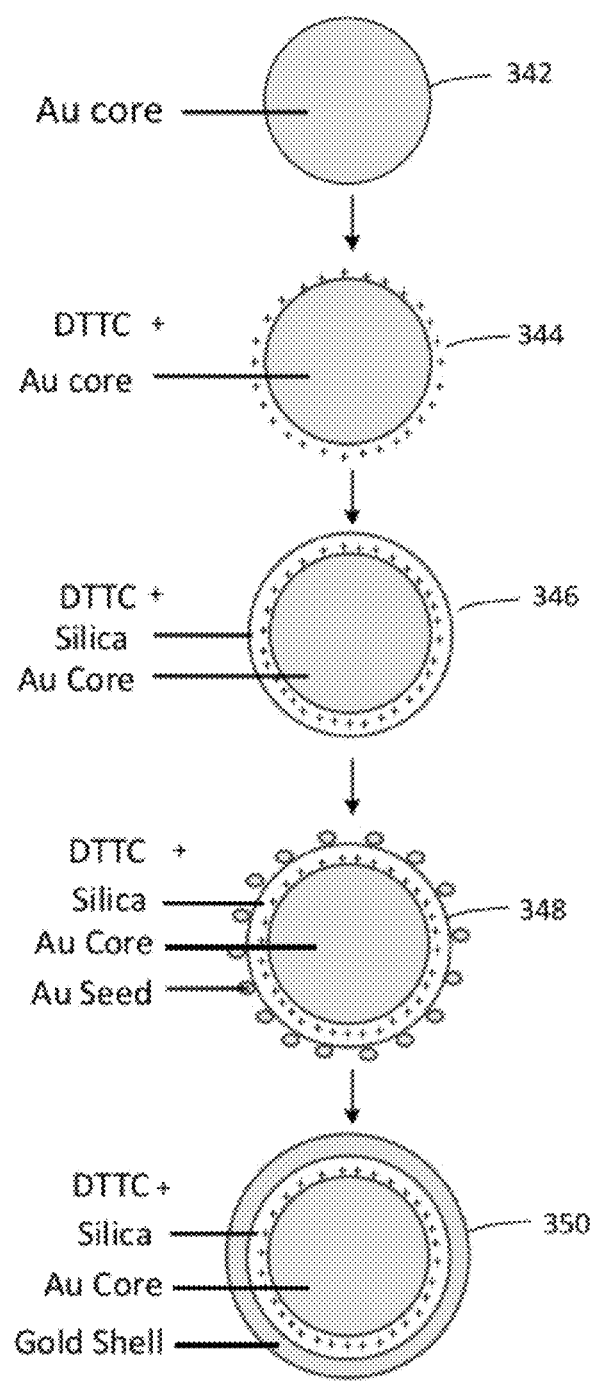
FIG. 34 is a schematic diagram illustrating one embodiment of making a gold-silica nano-LAMP with embedded reporter molecules.

A representative method for making one embodiment of a multilayered gold-silica nanoparticle is illustrated in FIG. 34. A citrate-capped gold nanoparticle core 342 is functionalized and seeded with dielectric seeds, e.g., mPEG-thiol (MW=5,000), and diethylthiatricarbocyanine iodide (DTTC, a reporter molecule) to produce a seeded nanoparticle 344. Because DTTC is a charged molecule and the polyethylene glycol groups are polar, it is believed that the vast majority of DTTC molecules will be positioned along the length of the polyethylene glycol chain. A first silica layer is formed on the gold core by reacting the seeded core with TEOS in a modified Stoller process to produce a nanoparticle 346 comprising a gold core and a silica layer including embedded DTCC molecules. The silica-coated nanoparticle is functionalized with (3-aminopropyl)trimethoxysilane (APTMS) and seeded with gold nanoseeds (e.g., 2-nm gold spheres) in the presence of a surfactant (e.g., tetrakis(hydroxymethyl)-phosphonium chloride) to produce a seeded nanoparticle 348. A gold layer is formed by reducing additional gold, e.g., using $HAuCl_4$, onto the gold nanoseeds, thereby forming a multilayered nanoparticle 350 comprising a gold core, a first silica layer comprising embedded DTTC molecules, and an outer gold layer. These steps can be repeated to add alternating silica (with or without reporter molecules) and gold layers onto the nanoparticle. The thickness of each silica and gold layer can be controlled by varying the concentrations of the TEOS and $HAuCl_4$, respectively. Embodiments of the disclosed nano-LAMPs terminate with formation of an outer silica layer devoid of reporter molecules.

IV. APPLICATIONS

A. Detection of Analytes

Figure 35:
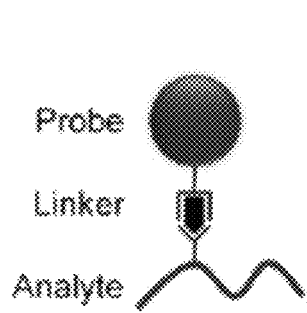
FIG. 35 is a schematic diagram of one embodiment of the disclosed nano-LAMPs conjugated to a linker and bound to an analyte molecule.
Figure 36:
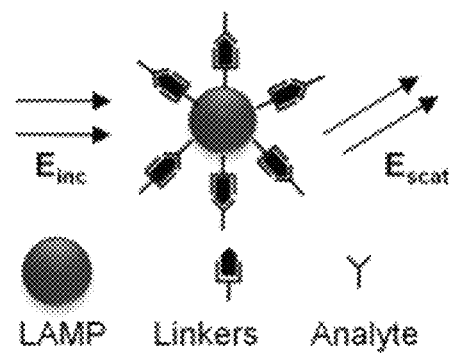
FIG. 36 is a schematic diagram of one embodiment of the disclosed nano-LAMPs conjugated to a plurality of linkers and bound to a plurality of analyte molecules.

One embodiment of a method for detecting an analyte using the disclosed nano-LAMPs is illustrated in FIG. 35. The SERS probe's "tail" is a specific binding moiety capable of recognizing and binding to a specific molecular analyte of biochemical interest (e.g., a target analyte). Molecular analytes that can be detected with the disclosed nano-LAMPs and methods provided herein include proteins (e.g., peptides, enzymes, antibodies, receptors, peptide hormones), nucleic acids (e.g., DNA sequences, RNA sequences, oligonucleotides), microbes (e.g., bacteria, viruses, fungi, parasites), carbohydrates, amino acids, toxins, and metals (e.g., heavy metals such as lead, mercury, arsenic, and cadmium). Suitable tails include, but are not limited to, antibodies capable of recognizing and binding to an analyte, oligonucleotides capable of hybridizing to an analyte, and proteins, peptides, or amino acids capable of binding to an analyte. In some embodiments, a plurality of tails, or binding moieties, is conjugated to a nano-LAMP (FIG. 36). The SERS probe's "head" is a nano-LAMP comprising nanostructured metal, dielectric and reporter components. In some embodiments, the probe head (see, e.g., FIG. 1A) comprises dielectric layers with embedded reporter molecules alternating with metal layers. The nano-LAMP is designed such that the enhancement region is localized within the nano-LAMP, thereby enhancing the spectral response of the reporter, which is detected and/or quantified. In some embodiments, the probe head (see, e.g., FIG. 1A) comprises dielectric layers with embedded reporter molecules alternating with metal layers. Thus, in one embodiment, a sample comprising an analyte is incubated with a probe comprising a nano-LAMP and a specific binding moiety capable of recognizing and binding to the analyte. The incubation is performed under conditions sufficient to detect the analyte. The sample then is illuminated with a suitable excitation wavelength, and the analyte is detected and/or quantified by visualizing and/or measuring one or more Raman scattering peaks characteristic of the reporter molecules.

In one embodiment, a nano-LAMP is designed such that the enhancement region is outside the nano-LAMP, thereby amplifying the signal of an analyte in the vicinity of the nano-LAMP, e.g., an analyte within 500 nm of the nano-LAMP, within 250 nm of the nano-LAMP, within 100 nm of the nano-LAMP, within 50 nm of the nano-LAMP, within 10 nm of the nano-LAMP, or within 5 nm of nano-LAMP. In one embodiment, a sample comprising an analyte (e.g., a liquid sample) is combined with a nano-LAMP designed such that the enhancement region is outside the nano-LAMP. The sample then is illuminated with an excitation wavelength, and the analyte is detected and/or quantified by visualizing and/or detecting one or more Raman scattering peaks characteristic of the analyte.

In another embodiment, a sample (such as one known or suspected of containing one or more target analytes) is combined (e.g., contacted) with a probe comprising a nano-LAMP designed such that the enhancement region is outside the nano-LAMP and a specific binding moiety capable of recognizing and binding to an analyte, thereby bringing the analyte in proximity to the nano-LAMP. The sample then is illuminated with an excitation wavelength, and the analyte is detected and/or quantified by visualizing and/or detecting one or more Raman scattering peaks characteristic of the analyte. Detecting one or more Raman scattering peaks characteristic of the target analyte indicates the presence of the target analyte in the sample. In one example, the nano-LAMP is administered (e.g., intravenously, intramuscularly, subcutaneously, transdermally, orally, intratumorally, and the like), to a subject (e.g., mammalian subject, such as a human), and then the subject or region of the subject is illuminated with an excitation wavelength, and the analyte is detected and/or quantified by visualizing and/or detecting one or more Raman scattering peaks characteristic of the analyte. Detecting one or more Raman scattering peaks characteristic of the target analyte indicates the presence of the target analyte in the subject.

B. Multiplexed Assays

Multiplexed assays allow the detection and/or quantitation of more than one target analyte in a single sample. As discussed above, nano-LAMPs can be contacted with a sample, or administered to a subject (e.g., mammalian subject, such as a human), to determine if the first target analyte and/or the subsequent target analyte are present in the sample/subject. In one embodiment, a sample is known or suspected of containing a first analyte and a subsequent analyte. The first analyte is detected and/or quantified using a first probe comprising a first nano-LAMP and a first specific binding moiety capable of recognizing and binding to the first analyte. The first nano-LAMP comprises a plurality of first reporter molecules embedded in one or more dielectric shells. The subsequent analyte is detected and/or quantified using a subsequent probe comprising a subsequent nano-LAMP and a subsequent specific binding moiety capable of recognizing and binding to the subsequent analyte. The subsequent nano-LAMP comprises a plurality of subsequent reporter molecules embedded in one or more dielectric shells. The first reporter molecule and the subsequent reporter molecule have different Raman spectra. In particular, the first reporter molecule and the subsequent reporter molecule each produce at least one unique Raman scattering peak when illuminated by an excitation signal. Thus, the first reporter molecule produces a first unique Raman scattering peak at a first wavelength, and the subsequent reporter molecules produces a subsequent unique Raman scattering peak at a subsequent wavelength, wherein the first wavelength and the subsequent wavelength are not the same. Preferably the first wavelength and the subsequent wavelength are at least 5 nm apart, at least 10 nm apart, at least 50 nm apart, or at least 100 nm apart. Typically, the first nano-LAMP and the subsequent nano-LAMP have substantially the same size to eliminate any differences due to size differences affecting the nano-LAMPs' interactions with the analytes. The first and subsequent nano-LAMPs also typically include the same metal and the same dielectric material to eliminate any differences due to the metal composition and/or dielectric material composition. Detecting the unique Raman scattering peak characteristic of first nano-LAMP indicates the presence of the first target analyte in the sample, and detecting the unique Raman scattering peak characteristic of the subsequent nano-LAMP indicates the presence of the subsequent target analyte in the sample. Thus, the sample is incubated with the first and subsequent probes under conditions sufficient to detect both analytes. The first analyte is detected and/or quantified by visualizing and/or measuring the first Raman scattering peak. The subsequent analyte is detected and/or quantified by visualizing and/or measuring the subsequent Raman scattering peak. The quantitation of the first and subsequent analytes may be relative to one another, e.g., by determining a ratio of the first Raman scattering peak to the subsequent Raman scattering peak. Alternatively, the quantitation of each analyte may be absolute, e.g., by first preparing a standard curve comparing the peak sizes to known concentrations of each analyte. Representative strategies to use spectroscopic signatures for quantitative analyses via efficient computer algorithms are available to analyze the data.[18]

In one embodiment, a sample includes a first target analyte and a subsequent target analyte. The first analyte is detected and/or quantified using a first probe comprising a first nano-LAMP and a first specific binding moiety capable of recognizing and binding to the first analyte. The subsequent analyte is detected and/or quantified using a subsequent probe comprising a subsequent nano-LAMP and a subsequent specific binding moiety capable of recognizing and binding to the subsequent analyte. The first and subsequent nano-LAMPs have the same overall size, the same chemical composition, and the same number of layers. The first nano-LAMP and the subsequent nano-LAMP each comprise a plurality of reporter molecules in at least one dielectric layer other than the outer silica shell. The reporter molecules in the first nano-LAMP and the subsequent nano-LAMP have the same chemical composition. However, the first and subsequent nano-LAMPs differ in the thicknesses of their individual layers, thereby producing at least a first unique Raman scattering peak from the first probe and a subsequent unique Raman scattering peak from the subsequent probe. Detecting the unique Raman scattering peak characteristic of the first nano-LAMP indicates the presence of the first target analyte in the sample, and detecting the unique Raman scattering peak characteristic of the subsequent nano-LAMP indicates the presence of the subsequent target analyte in the sample. Thus, the sample is incubated with the first and subsequent probes under conditions sufficient to detect both analytes. The first analyte is detected and/or quantified by visualizing and/or measuring the first unique Raman scattering peak, and the subsequent analyte is detected and/or quantified by visualizing and/or measuring the subsequent unique Raman scattering peak.

In another embodiment, a sample includes a first target analyte and a subsequent target analyte. The first analyte is detected and/or quantified using a first probe comprising a nano-LAMP and a first specific binding moiety capable of recognizing and binding to the first analyte. The subsequent analyte is detected and/or quantified using a subsequent probe comprising the nano-LAMP and a subsequent specific binding moiety capable of recognizing and binding to the subsequent analyte. The nano-LAMP comprises a plurality of first reporter molecules embedded in a first dielectric layer and a plurality of subsequent reporter molecules embedded in a subsequent dielectric layer, wherein the first reporter molecules and the subsequent reporter molecules have different chemical compositions. The first reporter molecules produce a first unique Raman scattering peak when exposed to a first excitation wavelength. The subsequent reporter molecules produce a subsequent unique Raman scattering peak when exposed to a subsequent excitation wavelength. Detecting the unique Raman scattering peaks characteristic of the first and subsequent reporter molecules indicates the presence of the first and subsequent target analytes, respectively, in the sample. Thus, the sample is incubated with the first and subsequent probes under conditions sufficient to detect both analytes. The first analyte is detected and/or quantified by exposing the sample to the first excitation wavelength, and visualizing and/or measuring the first unique Raman scattering peak. The subsequent analyte is detected and/or quantified by exposing the sample to the subsequent excitation wavelength, and visualizing and/or measuring the subsequent unique Raman scattering peak.

In another embodiment, a first target analyte and a subsequent target analyte are present in significantly differing concentrations in a sample. For example, the first analyte may be present at a low concentration whereas the subsequent analyte may be abundant. The first analyte and the subsequent analyte can be detected and/or quantified using a single nano-LAMP designed to produce an enhanced reporter signal at a first wavelength and a quenched reporter signal at a subsequent wavelength. Two probes are prepared. A first probe comprises the nano-LAMP and a first specific binding moiety capable of recognizing and binding to the first analyte. A subsequent probe comprises the nano-LAMP and a subsequent specific binding moiety capable of recognizing and binding to the subsequent analyte. The sample is incubated with the first probe under conditions sufficient to detect the first analyte. The first analyte is detected and/or quantified by illuminating the sample with a first excitation wavelength suitable to produce an enhanced reporter signal from the nano-LAMP. The subsequent analyte is not detected since the first probe is not capable of recognizing and binding to the subsequent analyte. The sample then is incubated with the subsequent probe under conditions sufficient to detect the subsequent analyte. The subsequent analyte is detected and/or quantified by illuminating the sample with a subsequent excitation wavelength suitable to produce a quenched, or minimized, signal from the nano-LAMP. Thus, detecting the enhanced reporter signal indicates the presence of the first target analyte in the sample, and detecting the quenched, or minimized, reporter signal indicates the presence of the subsequent target analyte in the sample. The first analyte typically is not detected under these conditions since it is not present in sufficient concentration to produce a measurable response using a quenched nano-LAMP. However, if the first analyte has a sufficient concentration to produce a measurable response under these conditions, the sample also may be illuminated with the subsequent excitation wavelength before incubating the sample with the subsequent probe, which will produce a quenched signal from the first analyte. The quenched signal attributable to the first analyte can then be subtracted from the combined quenched signal produced after incubation with the subsequent probe to provide a corrected signal attributable solely to the subsequent analyte.

In another embodiment, a sample includes a first target analyte that is present in a low concentration and a subsequent target analyte that is relatively abundant. The first analyte is detected and/or quantified using a probe comprising a specific binding moiety capable of recognizing and binding to the first analyte and a first nano-LAMP designed to have a first NEF at a given excitation wavelength. The subsequent analyte is detected and/or quantified using a probe comprising a specific binding moiety capable of recognizing and binding to the subsequent analyte and a subsequent nano-LAMP designed to have a subsequent NEF at the given excitation wavelength. The first and subsequent nano-LAMPs are selected to have a NEF ratio similar to the concentration ratio of the first and subsequent analytes. For instance, if the first and subsequent analytes differ in concentration by a factor of $10^6$, then nano-LAMPs that have a similar NEF ratio are selected, e.g., the nano-LAMPs may differ in NEF by $10^5$ to $10^7$. Typically, the first nano-LAMP and the subsequent nano-LAMP have substantially the same size to eliminate any differences due to size differences affecting the nano-LAMPs' interactions with the analytes. The first and subsequent nano-LAMPs may include the same metal and the same dielectric material to eliminate any differences due to the metal composition and/or dielectric material composition. Generally, the first and subsequent nano-LAMPs each include a plurality of reporter molecules in at least one dielectric layer. In some embodiments, the first nano-LAMP comprises resonant reporter molecules in one or more of its dielectric layers, and the subsequent nano-LAMP comprises non-resonant reporter molecules in one or more of its dielectric layers. In some embodiments, the first nano-LAMP may comprise reporter molecules at a higher concentration than the subsequent nano-LAMP. In some embodiments, the subsequent nano-LAMP may comprise different number of layers (e.g., 3 layers) than the first nano-LAMP, which may comprise, for example, 6 layers. In some embodiments, the first nano-LAMP is selected to provide an enhanced signal whereas the subsequent nano-LAMP is selected to provide a quenched or minimized signal. If the first nano-LAMP and the subsequent nano-LAMP each produce at least one unique Raman scattering peak (e.g., if the first and subsequent nano-LAMPs comprise different reporter molecules) when illuminated by the excitation wavelength, the two analytes can be detected and/or quantified simultaneously. Typically, the nano-LAMPs are selected so that the unique Raman scattering peaks are at least 5 nm apart, at least 10 nm apart, at least 50 nm apart, or at least 100 nm apart. In such instances, the sample is incubated with the first probe and the subsequent probe under conditions sufficient to detect the first analyte and the subsequent analyte. The sample then is illuminated at the excitation wavelength, and the first and subsequent analytes are detected and/or quantified by visualizing and/or measuring the unique Raman scattering peaks representative of each nano-LAMP. Detecting the unique Raman scattering peak characteristic of the first nano-LAMP indicates the presence of the first target analyte in the sample, and detecting the unique Raman scattering peak characteristic of the subsequent nano-LAMP indicates the presence of the subsequent target analyte in the sample.

If, however, the first nano-LAMP and the second nano-LAMP do not produce unique Raman scattering peaks (e.g., the reporter molecules are the same, and the nano-LAMPs instead differ in the reporter molecule concentration and/or the number of layers), then the first and subsequent target analytes are detected and/or quantified sequentially. In such cases, the sample is incubated with the first probe under conditions sufficient to detect the first analyte. The first analyte is detected and/or quantified by illuminating the sample with the excitation wavelength and then detecting and/or measuring the enhanced reporter signal from the first nano-LAMP. The subsequent analyte is not detected since the first probe is not capable of recognizing and binding to the subsequent analyte. The sample then is incubated with the subsequent probe under conditions sufficient to detect the subsequent analyte. The subsequent analyte is detected and/or quantified by illuminating the sample with the excitation wavelength and then detecting and/or measuring the quenched, or minimized, signal. The first analyte is also detected under these conditions since the first probe has previously been bound to the first analyte and will produce its enhanced signal; however, the signal attributable to the subsequent analyte may be determined by subtracting the signal attributable to the first analyte (as measured before incubation with the subsequent probe).

In one embodiment, a sample (e.g., a liquid sample) comprises a plurality of target analytes, wherein each analyte produces at least one unique Raman scattering peak. Preferably the first and subsequent unique Raman scattering peaks are at least 5 nm apart, at least 10 nm apart, at least 50 nm apart, or at least 100 nm apart. The sample is combined with a nano-LAMP designed such that the enhancement region is outside the nano-LAMP. The sample then is illuminated with an excitation wavelength, and each analyte is detected and/or quantified by visualizing and/or detecting the unique Raman scattering peak(s) characteristic of each analyte. Detecting the first unique Raman scattering peak indicates the presence of the first target analyte in the sample, and detecting the subsequent unique Raman scattering peak indicates the presence of the subsequent target analyte in the sample.

In another embodiment, a sample comprises a first target analyte and a subsequent target analyte, wherein the first analyte is capable of producing a first unique Raman scattering peak and the subsequent analyte is capable of producing a subsequent unique Raman scattering peak. Preferably the first and subsequent unique Raman scattering peaks are at least 5 nm apart, at least 10 nm apart, at least 50 nm apart, or at least 100 nm apart. A first probe and a subsequent probe comprising a nano-LAMP designed such that the enhancement region is outside the nano-LAMP are provided; the same nano-LAMP is utilized for the first probe and the subsequent probe. The first probe further comprises a first specific binding moiety capable of recognizing and binding to the first analyte, thereby bringing the first analyte into proximity of the nano-LAMP. The subsequent probe further comprises a subsequent specific binding moiety capable of recognizing and binding to the subsequent analyte, thereby bringing the subsequent analyte into proximity of the nano-LAMP. Detecting the first unique Raman scattering peak indicates the presence of the first target analyte in the sample, and detecting the subsequent unique Raman scattering peak indicates the presence of the subsequent target analyte in the sample. Thus, the sample is combined with the first probe and the subsequent probe under conditions sufficient to detect the first analyte and the subsequent analyte. The sample then is illuminated with an excitation wavelength. The first analyte is detected and/or quantified by visualizing and/or detecting the first unique Raman scattering peak, and the subsequent is detected and/or quantified by visualizing and/or detecting the subsequent unique Raman scattering peak.

V. KITS

Also disclosed herein are embodiments of kits for carrying out various embodiments of the disclosed methods. The kits include at least one multilayered nanoparticle, i.e., a nano-LAMP, as described herein. In some embodiments, the nano-LAMP comprises alternating layers of a metal and a dielectric, terminating in an outer dielectric shell. In one embodiment, the metal is a transition metal and the dielectric is silica. In one embodiment, the nano-LAMP further includes a plurality of reporter molecules embedded in at least one dielectric layer. In some examples, the kits include one or more different populations of nano-LAMPs, wherein each nano-LAMP population is in a separate container. For example, the kit can include one population of nano-LAMPs that are specific for a first target analyte and a second population of nano-LAMPs that are specific for a subsequent target analyte.

In some embodiments, the kit includes a conjugate comprising an embodiment of a nano-LAMP and a specific binding moiety capable of recognizing and binding directly or indirectly to at least one target analyte. In one embodiment, the specific binding moiety is an antibody capable of recognizing and binding directly to the analyte. In another embodiment, the specific binding moiety is an antibody capable of recognizing and binding indirectly to the analyte. For example, the specific binding moiety may be an antibody capable of recognizing and binding to a monoclonal antibody that specifically binds to the analyte. In another embodiment, the specific binding moiety is a nucleic acid capable of recognizing and binding to a target nucleic acid sequence. In another embodiment, the specific binding moiety is functional nucleic acid, such as an aptamer, DNAzyme, or RNAzyme. For example, the kit can include one population of nano-LAMP conjugates that are specific for a first target analyte and a second population of nano-LAMP conjugates that are specific for a subsequent target analyte.

In some embodiments, the kit additionally contains suitable reagents for detecting the analyte. For example, the kit may include one or buffers to facilitate binding the specific binding moiety to the analyte. In some embodiments, the kit further includes instructions for performing at least one embodiment of the disclosed methods for detecting an analyte.

In some embodiments, the kit includes a plurality of nano-LAMPs and/or nano-LAMP conjugates suitable for performing multiplexed assays.

VI. EXAMPLES

Example 1

Synthesis and Characterization of a 3-layer Gold-Silica Nano-LAMP

A nano-LAMP including a gold core, a silica layer comprising diethylthiatricarbocyanine dye (DTTC, a reporter molecule), and an outer gold layer was prepared.

Formation of 12-nm Gold Seeds:

A solution of 0.01 M $HAuCl_4$ was prepared one day ahead of time. The solution then was centrifuged for 1 hour at 18000 RCF and only the top ~70% of supernatant was used.

A 2.5-ml aliquot of the 0.01 M $HAuCl_4$ was added to 100 ml of water in a 250-ml conical flask. The solution was heated to boiling. Once boiling, 3 ml of 1 wt % sodium citrate was rapidly added to the mixture. The color changed to a deep red with a characteristic peak at around 520 nm (UV/Vis).

Formation of Gold Nanoparticle Cores:

The methods described in *J. Am. Chem. Soc.* (2009), 131, 17042-17043 were used. Briefly, to 97.25 ml of deionized water was added 1 ml lwt % $HAuCl_4$ (previously spun at 18000 RCF for 1 hr) and 0.75 ml of 12-nm seed as synthesized. While spinning vigorously, 022 ml of 1 wt % sodium citrate and 1 ml (0.03 g in 10 ml) hydroquinone were added simultaneously.

Addition of DTTC/m-PEG-Thiol:

The methods described in *Nature Biotech* (2008) 26, 1, 83-90 were used. Briefly, to 80 ml of the prepared gold spheres was added 20 ml of 15 µM DTTC dropwise (3 µM final concentration), followed by 20 ml ($5\times10^{-6}$ moles) mPEG-5000 thiol in deionized water. The solution was stirred overnight. The solution then was centrifuged at 400 RCF for 30 minutes. The nanoparticles were resuspended in ethanol (EtOH), and concentrated to 20 ml.

Growth of the Silica Layer:

The methods described in *Langmuir* (2009), 25(24), 13894-13899 were used. Briefly, to 20 ml of the DTTC mPEG thiol spheres in EtOH was added 17.98 ml of EtOH, then 6.08 ml water, then 1.384 ml of 0.2 M ammonia in EtOH and 0.576 ml TEOS. The solution was stirred for 2 hours. The nanoparticles were centrifuged at 300 RCF for 45 minutes and resuspended in EtOH.

APTMS-Functionalized Gold Seeding:

The methods described in *Langmuir* (1993), 9, 2301-2309 were used. Briefly, to 20 ml silica DTTC mPEG thiol spheres in EtOH was added 2 ml APTMS (3-aminopropyltrimethoxysilane) 1 mM in EtOH. The solution was stirred overnight and then centrifuged at 300 RCF for 45 minutes. The nanoparticles were resuspended in 20 ml water, followed by addition of 140 ml 2 nm THPC (tetrakis(hydroxymethyl)-phosphonium chloride) and 6 ml 1 M NaCl. The solution was stirred overnight, and then centrifuged at 400 RCF for 30 minutes. The nanoparticles were resuspended (concentration dependent) in 40 ml DI. The centrifugation and resuspension steps were repeated.

Growth of the Gold Layer:

The methods described *Langmuir* (2008), 24, 14166-14171 were used. Briefly, to 10 ml of gold-seeded silica mPEG thiol DTTC spheres was added 0.5 L of gold hydroxide growth solution (0.0625 g $K_2CO_3$ and 3.75 ml 1 wt % $HAuCl_4^-$ in 500 ml DI) and the solution was aged for about 4 hours. While spinning, CO gas was bubbled through the solution for 30 seconds. The solution then was centrifuged three times at 175 RCF for 30 minutes. After each centrifugation step, the supernatant was discarded, and the particles were resuspended in deionized water.

Figure 37A:
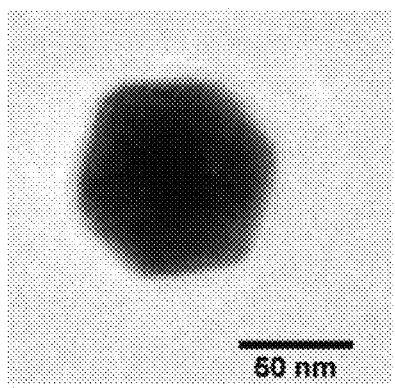
FIGS. 37A-37D are transmission electron microscopy photographs of one embodiment of a gold-silica nano-LAMP taken at each stage of the synthesis: gold core seeded with m-PEG-thiol and diethylthiatricarbocyanine (DTTC) (37A); gold core with silica layer containing embedded DTTC molecules (37B); gold core with silica layer containing embedded DTTC molecules and seeded with gold nanospheres (37C); gold core with silica layer containing embedded DTTC molecules and outer gold layer (37D).
Figure 37B:
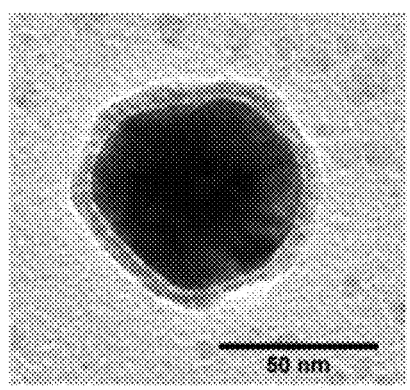
Figure 37C:
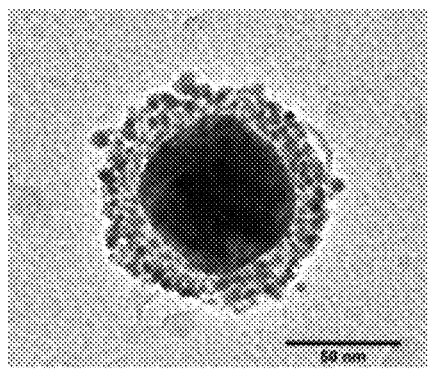
Figure 37D:
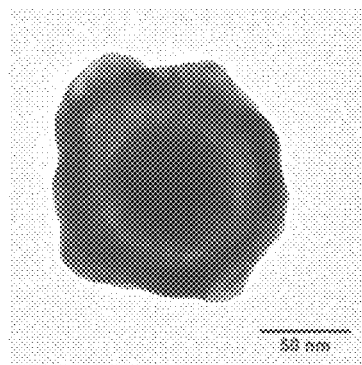

Characterization:

FIGS. 37A-37D are transmission electron microscopy photographs of the gold-silica nano-LAMP at various steps in the synthesis. FIG. 37A is a photograph of the gold nanoparticle core seeded with m-PEG-thiol and DTTC molecules. FIG. 37B is a photograph of the nanoparticle after growth of the silica layer, producing a nanoparticle having a gold core and a silica layer with embedded DTTC molecules. FIG. 37C is a photograph of the nanoparticle after being functionalized with APTMS and seeded with 2-nm gold spheres. FIG. 37D is a photograph of the nanoparticle after growth of the gold layer, producing a nanoparticle having a gold core, a silica layer with embedded DTTC molecules, and an outer gold layer.

At each stage of the synthesis, a UV-VIS absorbance spectrum of the particle was obtained (FIG. 38). As seen in FIG. 38, addition of the outer gold layer produced a marked change in the spectrum with a blue-shift of the original peak at about 575 nm and the appearance of a broad peak at about 800 nm, indicating growth of the gold layer.

Figure 39:
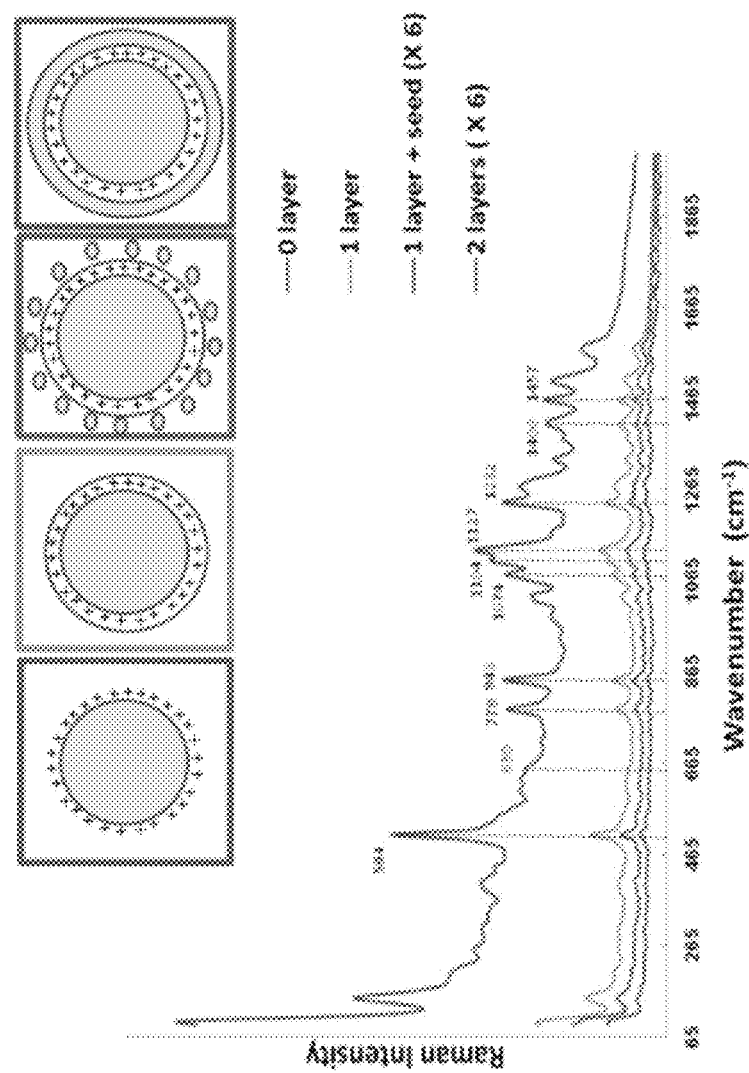
FIG. 39 is a series of Raman spectra obtained at each stage during the synthesis of a gold-silica nano-LAMP including a gold core with a silica layer containing embedded DTTC molecules and an outer gold layer.

After the initial seeding with m-PEG-thiol and DTTC, a Raman spectrum was obtained at each stage of the synthesis (FIG. 39).

Example 2

Synthesis of a 4-Layered Gold-Silica Nano-Lamp

An outer protective silica shell may be added to the 3-layered gold-silica nano-LAMP of Example 1. The outer gold surface may be seeded with mPEG-5000 thiol by suspending the gold nano-LAMPs in 100 ml of deionized water, and adding about 20 ml ($5\times10^{-6}$ moles) of mPEG-5000 thiol, followed by stirring overnight. The solution may then be centrifuged at 400 RCF for 30 minutes. The seeded nanoparticles may be resuspended in ethanol and concentrated to 20 ml. The silica shell may then be grown by adding 18 ml of EtOH, then 6 ml water, then 1.4 ml of 0.2 M ammonia in EtOH and 0.6 ml TEOS, followed by stirring the solution for 2 hours. The silica-coated nanoparticles may be collected by centrifugation at 300 RCF for 45 minutes and resuspended in EtOH.

In view of the many possible embodiments to which the principles of the disclosed disclosure may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

REFERENCES

1. Natan, *Faraday Discuss*, (2006) 132:321-238.
2. Chithrani et al., *Nano Lett.* (2006) 6:662-668.
3. Kodali et al., *Oxford handbook of nanoscience and technology*, A. V. Narlikar and Y. Y. Fu, eds., Oxford University Press (2010).
4. Kodali et al., *Proc. SPIE*, (2008) 7032, 7320V-1-10.
5. Johnson, *Appl. Opt.*, (1996) 35:3286-3296.
6. Wiscombe, *Appl. Opt.*, (1980) 19:1505-1509.
7. Palik, *Handbook of optical constants of solids III*, (1998) Academic Press, New York.
8. Khlebstov et al., *J. Biomed. Opt.*, (2006) 11:044002-1-5.
9. Xu et al., *Phys. Rev. Lett.*, (2004) 93, 243002-1-4.
10. Schatz et al., *Handbook of vibrational spectroscopy*, J. M. Chalmers and P. R. Griffiths, eds., (2002) John Wiley & Sons Ltd., Chichester, UK.
11. Pierce, *Mathematical tables and other aids to computation*, (1957) 11:244-249.
12. Goldberg, *Genetic algorithms in search, optimization, and machine learning reading*, (1989) Addison-Wesley, Massachusetts.
13. Johnson, *Appl. Opt.*, (1996) 35(18):3286-3296.
14. Wiscombe, *Appl. Opt.*, (1980) 19(9):1505-1509.
15. Sastry et al. *Intelligent Engineering Systems through Artifical Systems* (2001) 11:129-134.
16. Deb et al., *Complex systems* (1995) 9:115-148.
17. Deb et al., *Complex systems* (1995) 9:431-454.
18. Deb, *Multi-objective optimization using evolutionary algorithms* (2001) John Wiley and Sons, Chichester, UK.
19. Mullins et al., *Nanotechnology* (2005) 16:1950-1959.
20. Caruso et al., *Adv. Mater.* (2001) 13:1090-1094.
21. Liz-Marzan et al., *Handbook of Surfaces and Interfaces of Materials* (2001) 3:189-237
22. Kelly et al., *J. Phys. Chem. B*, (2003) 107:668-677.
23. Xia et al., *Nanotechnol.* (2006) 17:5435.
24. Johnson et al., *Phys. Rev. B.* (1972) 6:4370-4379.
25. Palik, *Handbook of Optical Constants of Solids* (1991) Academic Press.
26. Hu et al., *Opt. Exp.* (2008) 16:19579-19591.
27. Ghosh, *Opt. Comm.* (1999) 163:95-102.
28. Leupacher et al., *Appl. Opt.* (1984) 23:1554-1557.
29. Draine et al., *J. Opt. Soc. Am.* (1994) 4:1491-1499.

We claim:
1. A method of preparing a multilayered spherical nanoparticle, the method comprising:
   (1) providing a multilayered nanoparticle design by
      (a) selecting parameters for the multilayered spherical nanoparticle, the parameters comprising an overall diameter, a core diameter, a number of layers, a metal, a dielectric, thickness ranges for metal layers, thickness ranges for dielectric layers, a reporter molecule and a reporter molecule concentration;
      (b) storing the selected parameters in a database;
      (c) estimating, using a computer and based upon the selected parameters, field strengths for each layer;

(d) comparing, using the computer, estimated field strengths with prior estimated field strengths to provide a comparison;
(e) storing, using the computer, expansion coefficients;
(f) selecting, using the computer, a weighting function from a database, wherein the weighting function is based on a power of an electric field strength;
(g) applying, using the computer, the weighting function;
(h) selecting, using the computer, at least one nanoshell structure; and
(i) generating an output comprising a multilayered nanoparticle design based upon steps (a)-(h);
(2) providing a spherical metal or dielectric core;
(3) depositing a first layer onto the core by depositing a plurality of metal or dielectric seeds onto the core, wherein the seeds are (a) metal if the core is dielectric or (b) dielectric if the core is metal;
(4) growing the plurality of metal or dielectric seeds into a continuous metal layer or dielectric layer, respectively;
(5) depositing a plurality of alternating metal and dielectric layers onto the first layer by
depositing a plurality of metal or dielectric seeds onto the first layer or a subsequent layer, and
growing the plurality of metal or dielectric seeds into a continuous metal layer or dielectric layer, respectively;
(6) repeating step (5) to produce a number of layers determined by the multilayered nanoparticle design, wherein the layers terminate with an outer metal layer;
(7) adding a plurality of reporter molecules to at least one dielectric layer;
(8) depositing a plurality of dielectric seeds onto the outer metal layer; and
(9) growing the plurality of dielectric seeds into an outer dielectric shell, thereby producing a multilayered spherical nanoparticle comprising a spherical metal or dielectric core, a plurality of alternating metal and dielectric layers surrounding the core and terminating with an outer dielectric shell, and a plurality of embedded reporter molecules dispersed in at least one dielectric layer other than the outer dielectric shell, wherein the embedded reporter molecules are shielded by the at least one dielectric layer from direct contact with an adjacent metal layer.

2. The method of claim 1, further comprising functionalizing an outer surface of a dielectric core or a dielectric layer with a molecular linker comprising a first functional group capable of binding to the dielectric and a second functional group capable of binding to the metal before depositing the plurality of metal seeds.

3. The method of claim 2, wherein the metal is gold, the dielectric is silica, and the molecular linker comprises an alkoxy silane group and a thiol or amino group.

4. The method of claim 2, wherein the molecular linker is aminopropyl trimethoxy silane.

5. The method of claim 1, wherein the dielectric is silica and the dielectric seeds are methoxy-polyethylene glycol-thiol.

6. The method of claim 1, wherein the reporter molecules are added concurrently with the dielectric seeds.

7. The method of claim 1, wherein the at least one nanoshell structure is selected based at least in part on its ability to produce Raman signal enhancement in a region proximal to the multilayered nanoparticle when illuminated with an excitation wavelength.

8. The method of claim 1, wherein the at least one nanoshell structure is selected based at least in part on its ability to produce a region of Raman signal enhancement within the multilayered nanoparticle when illuminated with an excitation wavelength.

9. The method of claim 1, wherein the at least one nanoshell structure is selected based at least in part on its ability to produce a region of Raman signal quenching within the multilayered nanoparticle when illuminated with a first excitation wavelength.

10. The method of claim 9, wherein the at least one nanoshell structure is selected based at least in part on its further ability to produce a region of Raman signal enhancement within the multilayered nanoparticle when illuminated with a second excitation wavelength, wherein the first and second excitation wavelengths are not the same.

11. The method of claim 1, wherein the at least one nanoshell structure is selected based at least in part on its ability to exhibit a net enhancement factor of from $10^{-3}$ to $10^{15}$.

12. The method of claim 1, wherein the core diameter is at least 10 nm, each metal layer thickness is at least 2 nm, and each dielectric layer thickness is at least 1 nm.

* * * * *